US011590233B2

(12) United States Patent
Zannes et al.

(10) Patent No.: US 11,590,233 B2
(45) Date of Patent: Feb. 28, 2023

(54) PORPHYRIN COMPOUNDS AND COMPOSITIONS USEFUL FOR TREATING CANCER

(71) Applicant: OncoSelect Therapeutics, LLC, San Antonio, TX (US)

(72) Inventors: Maria Zannes, San Antonio, TX (US); Vivienne I. Rebel, San Antonio, TX (US); William E. Bauta, San Antonio, TX (US)

(73) Assignee: ONCOSELECT THERAPEUTICS, LLC, San Antonio, TX (US)

( * ) Notice: Subject to any disclaimer, the term of this patent is extended or adjusted under 35 U.S.C. 154(b) by 0 days.

(21) Appl. No.: 16/222,661

(22) Filed: Dec. 17, 2018

(65) Prior Publication Data
US 2019/0184021 A1  Jun. 20, 2019

Related U.S. Application Data

(63) Continuation of application No. PCT/US2017/037982, filed on Jun. 16, 2017.

(60) Provisional application No. 62/351,165, filed on Jun. 16, 2016.

(51) Int. Cl.
| C07D 487/22 | (2006.01) |
| A61K 47/55 | (2017.01) |
| A61K 47/54 | (2017.01) |
| A61P 35/00 | (2006.01) |
| A61K 9/00 | (2006.01) |
| A61K 45/06 | (2006.01) |
| A61K 47/34 | (2017.01) |
| A61K 47/10 | (2017.01) |
| A61K 47/26 | (2006.01) |

(52) U.S. Cl.
CPC ........... *A61K 47/55* (2017.08); *A61K 9/0021* (2013.01); *A61K 9/0024* (2013.01); *A61K 45/06* (2013.01); *A61K 47/34* (2013.01); *A61K 47/546* (2017.08); *A61P 35/00* (2018.01); *C07D 487/22* (2013.01); *A61K 47/10* (2013.01); *A61K 47/26* (2013.01)

(58) Field of Classification Search
CPC .................................................... C07D 487/22
See application file for complete search history.

(56) References Cited

U.S. PATENT DOCUMENTS

| 4,485,086 A | 11/1984 | Wong |
| 4,649,151 A | 3/1987 | Dougherty et al. |
| 4,783,529 A | 11/1988 | Lavallee et al. |
| 4,857,300 A | 8/1989 | Maksem |
| 4,889,120 A | 12/1989 | Gordon |
| 4,930,516 A | 6/1990 | Alfano |
| 5,004,811 A | 4/1991 | Bommer |
| 5,162,231 A | 11/1992 | Cole et al. |
| 5,238,940 A | 8/1993 | Liu et al. |
| 5,258,453 A | 11/1993 | Kopecek et al. |
| 5,391,547 A | 2/1995 | Cole et al. |
| 5,541,297 A | 7/1996 | Hansen et al. |
| 5,573,909 A | 11/1996 | Singer et al. |
| 5,601,825 A | 2/1997 | Hansen et al. |
| 5,906,977 A | 5/1999 | Sinn et al. |
| 6,091,843 A | 7/2000 | Horesh |
| 6,190,877 B1 | 2/2001 | Adair |
| 6,316,215 B1 | 11/2001 | Adair et al. |
| 6,643,041 B1 | 11/2003 | Ikeda et al. |
| 6,649,587 B1 | 11/2003 | Frydman et al. |
| 6,693,093 B2 | 2/2004 | Chowdhary et al. |
| 6,706,473 B1 | 3/2004 | Edman et al. |
| 6,838,248 B2 | 1/2005 | Garwin |
| 6,984,498 B2 | 1/2006 | Adair |
| 7,026,347 B2 | 4/2006 | Frydman et al. |
| 7,110,808 B2 | 9/2006 | Adair |
| 7,344,710 B2 | 3/2008 | Dang et al. |

(Continued)

FOREIGN PATENT DOCUMENTS

| CN | 102617610 | 8/2012 |
| EP | 2372361 | 10/2011 |

(Continued)

OTHER PUBLICATIONS

PubChem-CID 102126871, Dec. 24, 2015, 1-11.

(Continued)

*Primary Examiner* — Brian E McDowell
(74) *Attorney, Agent, or Firm* — Peacock Law P.C.; Janeen Vilven

(57) ABSTRACT

A porphyrin compound of Formula III

Formula III and composition made therefrom comprising a therapeutically effective dose of a porphyrin bound via a linker to an anti-cancer agent useful in treating cancer in a patient in need thereof or to treat cancer cells in-vitro. The compounds and compositions may be delivered by a drug delivery device as disclosed here and be part of a kit.

4 Claims, 15 Drawing Sheets

(56) References Cited

U.S. PATENT DOCUMENTS

| | | |
|---|---|---|
| 7,384,764 B2 | 6/2008 | Garwin |
| 7,670,799 B2 | 3/2010 | Garwin |
| 7,682,603 B2 | 3/2010 | Hammer et al. |
| 7,718,601 B2 | 5/2010 | Johannes et al. |
| 7,820,143 B2 | 10/2010 | Pandey et al. |
| 7,960,138 B2 | 6/2011 | Garwin |
| 8,148,335 B2 | 4/2012 | Moe et al. |
| 8,168,586 B1 | 5/2012 | Fang et al. |
| 8,180,436 B2 | 5/2012 | Boyden et al. |
| 8,188,239 B2 | 5/2012 | Hansen et al. |
| 8,198,246 B1 | 6/2012 | Sung et al. |
| 8,486,656 B2 | 7/2013 | Garwin |
| 8,877,509 B2 | 11/2014 | Dorian et al. |
| 8,975,038 B2 | 3/2015 | Garwin |
| 8,983,581 B2 | 3/2015 | Bawendi et al. |
| 9,155,471 B2 | 10/2015 | Lee et al. |
| 9,417,241 B2 | 8/2016 | Garwin |
| 2002/0115121 A1 | 8/2002 | Garwin |
| 2002/0155999 A1 | 10/2002 | Han |
| 2004/0192665 A1 | 9/2004 | Frydman et al. |
| 2004/0202612 A1 | 10/2004 | Adair |
| 2005/0079561 A1 | 4/2005 | Garwin |
| 2005/0233410 A1 | 10/2005 | Garwin |
| 2006/0058683 A1 | 3/2006 | Chance |
| 2006/0262301 A1 | 11/2006 | Watanabe et al. |
| 2006/0276444 A1 | 12/2006 | Frydman et al. |
| 2007/0172392 A1 | 7/2007 | Sen |
| 2007/0258986 A1 | 11/2007 | Qasba et al. |
| 2009/0004690 A1 | 1/2009 | Garwin |
| 2010/0216169 A1 | 8/2010 | Garwin |
| 2010/0329992 A1 | 12/2010 | Johannes et al. |
| 2011/0014647 A1 | 1/2011 | Dorian et al. |
| 2011/0243914 A1 | 10/2011 | Johannes et al. |
| 2012/0149057 A1 | 6/2012 | Garwin |
| 2013/0041307 A1 | 2/2013 | Aicher et al. |
| 2014/0011985 A1 | 1/2014 | Zannes et al. |
| 2014/0162287 A1 | 6/2014 | Garwin |
| 2014/0227188 A1 | 8/2014 | Tung et al. |
| 2015/0160197 A1 | 6/2015 | Dorian et al. |
| 2015/0177245 A1 | 6/2015 | Garwin |

FOREIGN PATENT DOCUMENTS

| | | |
|---|---|---|
| EP | 1364044 | 1/2012 |
| JP | S5587792 | 7/1980 |
| JP | 08-245480 | 9/1996 |
| JP | 1307070 | 5/2009 |
| KR | 1009622670000 | 6/2010 |
| RU | 1621720 | 9/1995 |
| WO | 91/19977 | 12/1991 |
| WO | 91/19978 | 12/1991 |
| WO | 92/06097 | 4/1992 |
| WO | 00/66528 | 11/2000 |
| WO | 02/42267 | 5/2002 |
| WO | 2004/012774 | 2/2004 |
| WO | 2011/009137 | 1/2011 |
| WO | 2017/218959 | 12/2017 |

OTHER PUBLICATIONS

Bartocci, C., et al., "A spectrosphotometric investigation on iron(III)protoporphyrin-IX in water/alcohol/pyridine solvent systems", Inorg. Chim. Acta. vol. 37, No. 1, 1979, L473-L476.

Berns, Michael W., et al., "In Vitro Cellular Effects of Hematoporphyrin Derivative", Cancer Research vol. 42, No. 6, 1982, 2325-2328.

Boring, Catherine C., "Cancer Statistics", CA Cancer J Clin vol. 43, No. 1, 1993, 7-26.

Bunseki, Kagaku, "Reversed-Phase Partition Chromatography for Trace Copper (II), Zinc (II), Manganese (II), and Cobalt (II) Using Tetrakis (4-Carboxyphenyl) Porphine", The Japan Society for Analytical Chemistry vol. 35, No. 9, 1986, 829-831.

Clarke, Suzanne E., et al., "Aqueous Complexation Equilibria of Meso Tetrakis(4-carboxyphenyl)porphyrine with Violgens", J of Physical Chemistry vol. 106, No. 13, 2002, 3235-3242.

Cole, D. A., et al., "Copper-67 Labeled Porphyrin Localization in Inflamed Tissue", Copper Bioavailability and Metabolism, 1990, 259-272.

Cole, D. A., et al., "The Biological Characteristics of a Water Soluble Porphyrin in Rat Lymph Nodes", Nucl. Med. Biol. Vole. 17, No. 5, 1990, 457-464.

Cortese, Denis A., et al., "Hematoporphyrin Derivative in the Detection and Localization of Radiographically Occult Lung Cancer", Am. Rev. Respir. Dis. vol. 126, No. 1, 1992, 1087-1088.

Dellinger, M., et al., "Cellular Uptake of Hydroxyethylvinyldeuteroporphyrin and Photoinactivation of Cultivated Human Leukemia (REH6) Cells", Biological Abstracts, 82:8, 1986, Philadelphia, PA, US; Abstract No. 75075, Abstract p. AB-679 of Photochem. Photobiol., 43:6, 1986, 639-648.

El-Far, M., et al., "A Comparative Study of 28 Porphyrins and Their Abilities to Localize in Mammary Mouse Carcinoma", Progress in Clinical and Biological Research, vol. 170, 1984, 661-672.

Ferguson, Mark K., "Diagnosing and Staging on Non-Small Cell Lung Cancer", Hematol Oncol Clin N AM vol. 4, No. 6, 1990, 1053-1068.

Firnau, G., et al., "Cu Labeling of Hematoporphyrin Derivative for Non-lnvasive In-Vivo Measurement of Tumor Uptake", Porphyrin Localization and Treatment of Tumors, 1984, 629-636.

Hambright, P., et al.," The Distribution of Various Water Soluble Radioactive Metalloporphyrins in Tumor Bearing Mice", Bioinorganic Chemistry vol. 5, 1975, 87-92.

Haroske, G., et al., "Frequency and Diagnostic Reliabilty of Subvisual Morphologic Markers for Malignancy in the Cervical Epithelium", Arch Geschwulstforsch vol. 58, No. 3, 1988, 159-168.

Hirsch, Fred R., et al., "Prevention and Early Detection of Lung Cancer-Clinical Aspects", Lung Cancer vol. 17, 1997, 163-174.

Hutchinson, Martha L., et al., "Measurement fo Subvisual Changes in Cervical Squamous Metaplastic Cells for Detecting Abnormality", Anal. Quant. Cytol. Estol. vol. 14, No. 4, 1992, 330-334.

Igarashi, Shukuro, et al., "Reversed phase-partition mode HPLC for small amounts of copper (II), zinc (II), manganese (II) and cobalt (II) with $\alpha$, $\beta$, $\gamma$, $\delta$-tetrakis (4-carboxyphenyl) porphine", Bunseki Kagaku (Analytical Chemistry) vol. 35, No. 9, 1986, 829-831.

Kancherla, K., et al., "Early Lung Cancer Detection using Nucleua Segmentation based Features", 2013 IEEE Symposium on Computational Intelligence in Bioinformatics and Computational Biology, 2013, 91-95.

Kancherla, K., et al., "Lung Cancer Detection Using Labeled Sputum Sample: Multi Spectrum Approach", Modern Approaches in Applied Intelligence, 2011, 446-458.

Kancherla, K., et al., "Non Intrusive and Extremely Early Detection of Lung Cancer Using TCPP", 2009 Fourth International Multi-Conference on Computing in the Global Information Technology, IEEE Computer Society, 2009, 104-108.

Kato, Harubumi, et al., "Early Detection of Lung Cancer by Means of Hematoporphyrin Derivative Fluorescence and Laser Photoradiation", Clinics in Chest Medicine vol. 6, No. 2, 1985, 237-253.

Mao, Li, et al., "Detection of Oncogene Mutations in Sputum Precedes Diagnosis of Lung Cancer", Cancer Research vol. 54, 1994, 1634-1637.

Mao, Li, et al., "Microsatellite Alterations as Clonal Markers for the Detection of Human Cancer", Proc. Natl. Acad. Sci. vol. 91, 1994, 9871-9875.

Mercer-Smith, Janet A., et al., "The Development of Copper-67-Labeled Porphyrin-Antibody Conjugates", Targeted Diagnosis and Therapy vol. 1, 1988, 317-352.

Moan, J., et al., "A Change is the Qauntum Yield of Photoinactivation of Cells Observed During Photodynamic Treatment", Biological Abstracts, 86:7, 1988, Philadelphia, PA, US; Abstract No. 72079; Abstract p. AB-772 of Lasers Med. Sci., 3:2, 1988, 93-98.

Moan, J., et al., "Photosensitizing Efficiencies, Tumor and Cellular Uptake of Different Photosensitizing Drugs Relevant for Photodynamic Therapy of Cancer", Biological Abstracts, 85:5, 1988, Philadelphia, PA, US; Abstract No. 49732; Abstract p. AB-723 of Photochem. Photobiol., 46:5, 1987, 713-722.

(56) References Cited

OTHER PUBLICATIONS

Moan, J., et al., "The Mechanism of Photodynamic Inactivation of Human Cells in Vitro in the Presence of Haematoporphyrin", Biological Abstracts, 68:10, 1979, Philadelphia, PA, US; Abstract No. 62117; Abstract p. 6230, Br J. Cancer, 39:4, 1979, 398-407.
Montag, Anthony G., et al., "Karyometric Features in Nuclei Near Colonic Adenocarcinoma", Anal. Quant. Cytol. Histol. vol. 13, 1991, 159-167.
Musser, David A., et al.,"The Binding of Tumor Localizing Porphyrins to a Fibrin Matrix and Their Effects Following Photoirradiation", Res. Comm. In Chem. Path. And Pharm. vol. 28, No. 3, 1980, 505-525.
Osaka, Tetsuya, et al., "Transmission Electron Microscopic Study on Electroless Plated Nickel-Molybdenum-Phosphorus Alloy Film", Jpn. J. Apple Phys Part 1, vol. 28, Suppl. 28-3, 1989, 229-233.
Patel, K. B., "Fluorescing Cells in Sputum After Parenteral HPD", Porphyrin Localization and Treatment of Tumors, 1984, 521-530.
Pegaz, B., et al., "Effect of the Lipophilicyt on the Phtothrombic Activity of Biodegradable Nanoparticles Loaded with Porphyrin Derivatives", TNT2004 Segovia Spain, 2004, 1-2.
Rao, Polisetti Dharma, et al., "Rational Syntheses of Porphyrins Bearing up to Four Different Meso Substituents", J. Org. Chem. vol. 65, No. 22, 2000, 7323-7334.
Roberts, Jeanette C., et al., "Preparation and Characterization of Copper-67 Porphyrin-Antibody Conjugates", Journal of Immun. Methods vol. 105, 1987, 153-164.
Roby, Tina J., et al., "Discriminant Analysis of Lower Respiratory Tract Components Associated with Cigarette Smoking, Based on Quantitative Sputum Cytology", Acta Cytol vol. 34, 1990, 147-154.
Roby, Tina J., et al., "Reliability of a Quantitative Interpretation of Sputum Cytology Slides", Acta Cytol vol. 34, 1990, 140-146.
Schumann, G. Berry, et al., "Quantitative Sputum Cytologic Findings in 109 Nonsmokers", Am Rev Respr Dis vol. 139, 1989, 601-603.
Shulok, Janine R., et al., "Subcellular Localization of Hematoporphyrin Derivative in Bladder Tumor Cells in Culture", Photochem and Photobiol vol. 51, No. 4, 1990, 451-457.
Sidransky, David, "Importance of Chromosome 9p Loss in Human Lung Cancer", J Natl Cancer Inst vol. 87, 1995, 1201-1202.
Tockman, Melvyn S., et al., "Sensitive and Specific Monoclonal Antibody Recognition of Human Lung Cancer Antigen on Preserved Sputum Cells: A New Approach to Early Lung Cancer Detection", J Clin Oncol vol. 11, 1988, 1685-1693.
Tockman, Melvyn S., "The Early Detection of Second Primary Lung Cancers by Sputum Immunostaining", Chest vol. 106, 1994, 385s-390s.
Wingo, Phyllis A., et al., "Cancer Statistics", CA Clinical J Clin vol. 45, 1995, 8-30.
Broughton, Laura J., et al., "Duramycin-porphyrin conjugates for targeting ot tumour cells using photodynamic therapy", Journal of Photochemistry & Photobiology, B: Biology 163, 2016, 374-384.
"MorEx Development Partners, LLP", 2018, 1.
Alliband, Amanda, "Synthesis and Characterization of Picket Porphyrin Receptors That Bind Phosphatidylglycerol, and Anionic Phospholipid Found in Bacterial Membranes", J. Org. Chem., vol. 78, 2013, 356-362.
Alonso, Cristina M. A., et al., "Site-Specific and Stoichiometric Conjugation of Cationic Porphyrins to Antiangiogenic Monoclonal Antibodies", Bioconjugate Chem., vol. 21, 2010, 302-313.
Anatelli, Florencia, et al., "Macrophage-Targeted Photosensitizer Conjugate Delivered by Intratumoral Injection", Molecular Pharmaceutics, vol. 3, No. 6, 2006, 654-664.
Avval, Farnaz Zahedi, et al., "Mechanism of inhibition of ribonucleotide reductase with motexafin gadolinium (MGd)", Biochemical and Biophysical Research Communications, vol. 379, 2009, 775-779.
Bakar, Mohd Bakri, et al., "Lead structures for applications in photodynamic therapy. Part 2: Synthetic studies for photo-triggered release systems of bioconjugate porphyrin photosensitizers", Tetrahedron, vol. 65, 2009, 7064-7078.

Banfi, Stefano, et al., "Synthesis of Porphyrin-Anthraquinone", Synthetic Communications, vol. 38, 2008, 1096-1109.
Battogtokh, Gantumur, et al., "Mitochondrial-targeted photosensitizer-loaded folate-albumin nanoparticle for photodynamic therapy of cancer", Nanomedicine: Nanothechnology, Biology, and Medicine, vol. 13, 2017, 733-743.
Bhupathiraju, N. V. S. Dinesh K., "Synthesis and in Vitro Evaluation of BBB Permeability, Tumor Cell Uptake, and Cytotoxicity of a Series of Carboranylporphyrin Conjugates", J. Med. Chem., vol. 57, 2014, 6718-6728.
Cernay, TH., et al., "Selective photosensitization of mitochondria by the lipophilic cationic porphryin POR10", Journal of Photochemistry and Photobiology B: Biology 34, 1996, 191-196.
Chaloin, Laurent, et al., "Improvement of Porphyrin Cellular Delivery and Activity by Conjugation to a Carrier Peptide", Bioconjugate Chem., vol. 12, 2001, 691-700.
Chung, Clive Yik-Sham, et al., "A multi-functional PEGylated gold(III) compound: potent anti-cancer properties and self-assembly into nanostructures for drug co-delivery", Chemical Science, Issue 3, 2017, 1942-1953.
Cloonan, Suzanne M., et al., "Detailed Biological Profiling of a Photoactivated and Apoptosis Inducing pdppz Ruthenium(II) Polypyridyl Complex in Cancer Cells", J. Med. Chem., vol. 58, 2015, 4494-4505.
Das, Tapas, et al., "A novel 177Lu-labeled porphyrin for possible use in targeted tumor therapy", Nuclear Medicine and Biology, vol. 37, 2010, 655-663.
Dondi, R., et al., "Flexible synthesis of cationic peptide-porphyrin derivatives for light-triggered drug delivery and photodynamic therapy", Org. Biomol. Chem., vol. 14, 2016, 11488-11501.
Garcia, Guillaume, et al., "DNA photocleavage by porphyrin-polyamine conjugates", Bioorganic & Medicinal Chemistry, vol. 17, 2009, 767-776.
Gianferrara, Teresa, et al., "Ruthenium-Porphyrin Conjugates with Cytotoxic and Phototoxic Antitumor Activity", J. Med. Chem., vol. 53, 2010, 4678-4690.
Gianferrara, Teresa, et al., "Synthetic strategies towards ruthenium-porphyrin conjugates for anticancer activity", Dalton Trans., Issue 48, 2009, 10742-10756.
Hahn, Frank, et al., "Conjugation of Spermine Facilitates Cellular Uptake and Enhances Antitumor and Antibiotic Properties of Highly Lipophilic Porphyrins", ChemMedChem, vol. 3, 2008, 1185-1188.
Hambin, Michael R., et al., "Photosensitizer targeting in photodynamic therapy I. Conjugates of haematoporphyrin with albumin and trasferrin", Journal of Photochemistry and Photobiology B: Biology, vol. 26, 1994, 45-56.
Hao, Erhong, et al., "Carborane functionalized pyrroles and porphyrins via the Suzuki crosscoupling reaction", Chem. Commun., 2006, 4900-4902.
Hao, Erhong, et al., "Synthesis and Cellular Studies of Porphyrin-Cobaltacarborane Conjugates", Bioconjugate Chem., vol. 16, 2005, 1495-1502.
Hao, Erhong, "Synthesis and Spectroelectrochemistry of N-Cobaltacarborane Porphyrin Conjugates", Bioconjugate Chem., vol. 19, 2008, 2171-2181.
Hao, Yongwei, et al., "Tumor acidity-activatable manganese phosphate nanoplatform for amplification of photodynamic cancer therapy and magnetic resonance imaging", Acta Biomaterialia, vol. 62, 2017, 293-305.
Hill, John S., et al., "Selective tumor uptake of a boronated porphyrin in an animal model of cerebral glioma", Proc. Nati. Acad. Sci. USA, vol. 89, 1992, 1785-1789.
Hirohara, Shiho, et al., "Sugar and Heavy Atom Effects of Glycoconjugated Chlorin Palladium Complex on Photocytotoxicity", Bioconjugate Chem., vol. 23, 2012, 1881-1890.
Hudson, R., et al., "The development and characterisation of porphyrin isothiocyanate-monoclonal antibody conjugates for photoimmunotherapy", British Journal of Cancer, vol. 92, 2005, 1442-1449.
Ibrahim, Hanadi, et al., "Meso-tetraphenyl porphyrin derivatives: The effect of structural modifications on binding to DMPC liposomes and albumin", Journal of Phtochemistry and Photobiology A: Chemistry, vol. 217, 2011, 10-21.

(56) References Cited

OTHER PUBLICATIONS

Keda, Atsushi, et al., "Photodynamic Activities of Porphyrin Derivative-Cyclodextrin Complexes by Photoirradiation", ACS Med. Chem. Lett., vol. 8, 2017, 555-559.

Jadhav, Satish, et al., "Solid-Supported Porphyrins Useful for the Synthesis of Conjugates with Oligomeric Biomolecules", Bioconjugate Chem., vol. 27, 2016, 1023-1029.

Jia, Zhiyun, "Synthesis and preliminary biological studies of the novel conjugate 188Re-labeled meso-tetrakis(4-sulfophenyl)porphyrin in mice", Nuclear Medicine and Biology, vol. 34, 2007, 643-649.

Josefsen, Leanne B., et al., "Unique Diagnostic and Therapeutic Roles of Porphyrins and Phthalocyanines in Photodynamic Therapy, Imaging and Theranostics", Theranostics, vol. 2, No. 9, 2012, 916-966.

Kang, Xinmei, et al., "Photothermal therapeutic application of gold nanorodsporphyrin-trastuzumab complexes in HER2-positive breast cancer", Scientific Reports, vol. 7, No. 42069, 2017, 1-13.

Kitagishi, Hiroaki, et al., "Cellular uptake of octaarginine-conjugated tetraarylporphyrin included by per-O-methylated B-cyclodextrin", Org. Biomol. Chem., vol. 11, 2013, 3203-3211.

Kobylianskii, Ilia J., et al., "Co—C Bond Energies in Adenosylcobinamide and Methylcobinamide in the Gas Phase and in Silico", J. Am. Chem. Soc., vol. 135, 2013, 13648-13651.

Kobylianskii, Ilia J., et al., "Co—C bond energies in adenosylcobinamide and methylcobinamide in the gas phase and in silico", Supporting Information, 2013, S1-S47.

Kralova, Jarmila, et al., "Glycol Porphyrin Derivatives as Potent Photodynamic Inducers of Apoptosis in Tumor Cells", J. Med. Chem., vol. 51, 2008, 5964-5973.

Kralova, Jarmila, et al., "Porphyrin-bile acid conjugates: from saccharide recognition in the solution to the selective cancer cell fluorescence detection", Org. Biomol. Chem., vol. 6, 2008, 1548-1552.

Li, Shi-Ying, et al., "Cancer cell membrane-coated biomimetic platform for tumor targeted photodynamic therapy and hypoxia-amplified bioreductive therapy", Biomaterials, vol. 142, 2017, 149-161.

Li, Donghong, "Design, synthesis and biological evaluation of folate-porphyrin: a new photosensitizer for targeted photodynamic therapy", Journal of Porphyrins and Phthalocyanines, vol. 14, No. 06, 2010, 547.

Li, Dong Hong, et al., "Synthesis and anticancer activities of porphyrin induced anticancer drugs", Chinese Chemical Letters, vol. 18, 2007, 1331-1334.

Liu, Yanan, et al., "DNA binding and photocleavage properties and apoptosis-inducing activities of a ruthenium porphyrin complex [(Py-3')TPP-Ru(phen)2Cl]Cl and its heterometallic derivatives", Chemico-Biological Interactions, vol. 183, 2010, 349-356.

Liu, Feng, et al., "Doxorubicin-loaded redox-responsive amphiphilic dendritic porphyrin conjugates for chemotherapy and photodynamic therapy", RSC Adv., vol. 6, 2016, 57552-57562.

Liu, Kai, et al., "Simple Peptide-Tuned Self-Assembly of Photosensitizers towards Anticancer Photodynamic Therapy", Angew. Chem. Int. Ed., vol. 55, 2016, 3036-3039.

Loska, Rafal, et al., "Design and synthesis of protoporphyrin IX/vitamin B12 molecular hybrids viaCuAAC reaction", Journal of Porphyrins and Phthalocyanines, vol. 17, No. 01n02, 2013, 104.

Lottner, Christian, et al., "Distribution and subcellular localization of a water-soluble hematoporphyrin-platinum (II) complex in human bladder cancer cells", Cancer Letters, vol. 215, 2004, 167-177.

Lottner, Christian, et al., "Hematoporphyrin-Derived Soluble Porphyrin-Platinum Conjugates with Combined Cytotoxic and Phototoxic Antitumor Activity", J Med. Chem., vol. 45, 2002, 2064-2078.

Lottner, Christian, et al., "Soluble Tetraarylporphyrin-Platinum Conjugates as Cytotoxic and Phototoxic Antitumor Agents", J. Med. Chem., vol. 45, 2002, 2079-2089.

Maillard, PH., et al., "In vitro phototoxicity of glycoconjugated porphyrins and chlorins in colorectal adenocarcinoma (HT29) and retinoblastoma (Y79) cell lines", Photodiagnosis and Photodynamic Therapy, vol. 4, 2007, 261-268.

Maiolino, Sara, et al., "Hyaluronan-decorated polymer nanoparticles targeting the CD44 receptor for the combined photo/chemo-therapy of cancer", Nanoscale, vol. 7, 2015, 5643-5653.

Zhang, Ran, et al., "Asymmetric Cationic Porphyrin as a New G-Quadruplex Probe with Wash-Free Cancer-Targeted Imaging Ability Under Acidic Microenvironments", ACS Appl. Mater. Interfaces, vol. 10, 2018, 13350-13360.

Zhang, Tao, et al., "In vivo selective cancer-tracking gadolinium eradicator as new-generation photodynamic therapy agent", PNAS www.pnas.org/cgi/doi/10.1073/pnas.1414499111, 2014, E5492-E5497.

Zheng, Xiaohua, et al., "Self-Assembly of Porphyrin-Paclitaxel Conjugates Into Nanomedicines: Enhanced Cytotoxicity due to Endosomal Escape", Chem. Asian J., vol. 11, 2016, 1780-1784.

Zhou, Yan, et al., "avb3-Isoform specific erbium complexes highly specific for bladder cancer imaging and photodynamic therapy", Chem. Commun., vol. 53, 2017, 557-560.

Zhou, Chunfang, et al., "Targeted Photodynamic Therapy with a Folate/Sensitizer Assembly Produced from Mesoporous Silica", Chem. Eur. J., vol. 23, 2017, 7672-7676.

Zhou, Hejiang, et al., "The inhibition of migration and invasion of cancer cells by graphene via the impairment of mitochondrial respiration", Biomaterials, vol. 35, 2014, 1597-1607.

Zou, Qianli, et al., "Biological Photothermal Nanodots Based on Self-Assembly of Peptide-Porphyrin Conjugates for Antitumor Therapy", J. Am. Chem. Soc., vol. 139, 2017, 1921-1927.

Maruani, Antoine, et al., "Site-selective multi-porphyrin attachment enables the formation of a next-generation antibody-based photodynamic therapeutic", Chem. Commun., vol. 51, 2015, 15304-15307.

Meng, Shuai, et al., "Synthesis, characterization and in vitro photodynamic antimicrobial activity of basic amino acid-porphyrin conjugates", European Journal of Medicinal Chemistry, vol. 92, 2015, 35-48.

Moon, Hyungwon, et al., "Multifunctional theranostic contrast agent for photoacoustics- and ultrasound-based tumor diagnosis and ultrasound-stimulated local tumor therapy", Journal of Controlled Release, vol. 218, 2015, 63-71.

Moylan, Claire, et al., "Lead structures for applications in photodynamic therapy 7. Efficient synthesis of amphiphilic glycosylated lipid porphyrin derivatives: refining linker conjugation for potential PDT applications", Tetrahedron, vol. 71, 2015, 4145-4153.

Muhanna, Nidal, et al., "Phototheranostic Porphyrin Nanoparticles Enable Visualization and Targeted Treatment of Head and Neck Cancer in Clinically Relevant Models", Theranostics, vol. 5, Issue 12, 2015, 1428-1443.

Mukai, Hidefumi, et al., "The synthesis of 64Cu-chelated porphyrin photosensitizers and their tumor-targeting peptide conjugates for the evaluation of target cell uptake and PET image-based pharmacokinetics of targeted Photodynamic therapy agents", Ann Nucl Med, vol. 27, 2013, 625-639.

Naik, Anu, et al., "Visible-Light-Induced Annihilation of Tumor Cells with Platinum-Porphyrin Conjugates", Angew. Chem. Int. Ed., vol. 53, 2014, 6938-6941.

Ngen, Ethel J., et al., "Evaluation of delocalized lipophilic cationic dyes as delivery vehicles for photosensitizers to mitochondria", Bioorganic & Medicinal Chemistry, vol. 17, 2009, 6631-6640.

Orosz, Adam, et al., "Binding of new cationic porphyrin-tetrapeptide conjugates to nucleoprotein complexes", Biophysical Chemistry, vol. 177-178, 2013, 14-23.

Osman, Safiye, et al., "Comparative Biodistribution and Metabolism of Carbon-11-labeled N-[2-(Dimethylamino) ethyl]acridine-4-carboxamide and DNA-intercalating Analogues", Cancer Research, vol. 61, 2001, 2935-2944.

Pan, Jie, et al., "Exitation energy transfer in ruthenium (II-)porphyrin conjugates led to enhanced emission quantum yield and 1O2 generation", Journal of Luminescence, vol. 184, 2017, 89-95.

Penon, Oriol, et al., "Water soluble, multifunctional antibody-porphyrin gold nanoparticles for targeted photodynamic therapy", Journal of Colloid and Interface Science, vol. 496, 2017, 100-110.

Pires, Sonia M.G., et al., "Porphyrin-rhodamine conjugates as new materials with sensing ability", Dyes and Pigments, vol. 135, 2016, 113-126.

(56) References Cited

OTHER PUBLICATIONS

Rajora, M. A., et al., "Tailored theranostic apolipoprotein E3 porphyrin-lipid nanoparticles target glioblastoma", Chem. Sci., vol. 8, 2017, 5371-5384.

Ramzy, Lydia, et al., "Cancer nanotheranostics: A review of the role of conjugated ligands for overexpressed receptors", European Journal of Pharmaceutical Sciences, vol. 104, 2017, 273-292.

Rani-Beeram, Sandya, et al., "A Fluorinated Ruthenium Porphyrin as a Potential Photodynamic Therapy Agent: Synthesis, Characterization, DNA Binding, and Melanoma Cell Studies", Inorg. Chem., vol. 47, 2008, 11278-11283.

Rogers, Luke, et al., "Lead Structures for Applications in Photodynamic Therapy. 6. Temoporfin Anti-Inflammatory Conjugates to Target the Tumor Microenvironment for In Vitro PDT", PLoS ONE, vol. 10, No. 5, 2015, 1-13.

Rogers, Luke, et al., "Synthesis and biological evaluation of Foscan bile acid conjugates to target esophageal cancer cells", Bioorganic & Medicinal Chemistry Letters, vol. 23, 2013, 2495-2499.

Rostami, Mahboubeh, et al., "Synthesis of some new porphyrins and their metalloderivatives as potential sensitizers in photodynamic therapy", Res Pharm Sci., vol. 10, No. 6, 2015, 504-513.

Sadler, Sara, et al., "Internalization of a C17a-alkynylestradiol-porphyrin conjugate into estrogen receptor positive MCF-7 breast cancer cells", Bioorganic & Medicinal Chemistry Letters, vol. 21, 2011, 4638-4641.

Schmidt-Erfurth, U., et al., "Photodynamic targeting of human retinoblastoma cells using covalent low-density lipoprotein conjugates", British Journal of Cancer, vol. 75, No. 1, 1997, 54-61.

Schmitt, Frederic, et al., "Combined arene ruthenium porphyrins as chemotherapeutics and photosensitizers for cancer therapy", J Biol Inorg Chem, vol. 14, 2009, 101-109.

Schmitt, Frederic, et al., "Sawhorse-type diruthenium tetracarbonyl complexes containing porphyrin-derived ligands as highly selective photosensitizers for female reproductive cancer cells", J Biol Inorg Chem, vol. 14, 2009, 693-701.

Schwach, Gert, et al., "A water soluble tri-cationic porphyrin-EDTA conjugate induces apoptosis in human neuroendocrine tumor cell lines", Bioorganic Chemistry, vol. 40, 2012, 108-113.

Sehgal, Inder, et al., "Photoinduced Cytotoxicity and Biodistribution of Prostate Cancer Cell-Targeted Porphyrins", J. Med. Chem., vol. 51, 2008, 6014-6020.

Shieh, Yen-An, et al., "Aptamer-Based Tumor-Targeted Drug Delivery for Photodynamic Therapy", ACS NANO, vol. 1, No. 3, 2010, 1433-1442.

Sibrian-Vazquez, Marth, et al., "Mitochondria Targeting by Guanidine- and Biguanidine-Porphyrin Photosensitizers", Bioconjugate Chem, vol. 19, 2008, 705-713.

Sibrian-Vazquez, Martha, et al., "Peptide-Mediated Cell Transport of Water Soluble Porphyrin Conjugates", J. Med. Chem., vol. 49, 2006, 1364-1372.

Sibrian-Vazquez, Martha, et al., "Porphyrin-Retinamides: Synthesis and Cellular Studies", Bioconjugate Chem., vol. 18, 2007, 1185-1193.

Sibrian-Vazquez, Martha, et al., "Synthesis and Characterization of Positively Charged Porphyrin-Peptide Conjugates", Bioconjugate Chem., vol. 16, 2005, 852-863.

Sibrian-Vazquez, Martha, et al., "Synthesis, Characterization, and Metabolic Stability of Porphyrin-Peptide Conjugates Bearing Bifunctional Signaling Sequences", J Med. Chem., vol. 51, 2008, 2915-2923.

Silva, Sandrina, et al., "Porphyrin and phthalocyanine glycodendritic conjugates: synthesis, photophysical and photochemical properties", Chem. Commun., vol. 48, 2012, 3608-3610.

Smith, Gregory S., et al., "Targeted and multifunctional arene ruthenium chemotherapeutics", Dalton Trans., vol. 40, 2011, 10793-10800.

Songca, Sandile P., et al., "In-vitro activity and tissue distribution of new fluorinated meso-tetrahydroxyphenylporphyrin photosensitizers", JPP, vol. 53, 2001, 1469-1476.

Stichelberger, Albert, et al., "Versatile synthetic approach to new bifunctional chelating agents tailor made for labeling with the fac-[M(CO)3]+ core (M=Tc, 99mTc, Re): synthesis, in vitro, and in vivo behavior of the model complex [M(APPA)(CO)3] (APPA=[(5-amino-pentyl)-pyridin-2-ylyl-methylamino]-acetic acid)", Nuclear Medicine and Biology, vol. 30, 2003, 465-470.

Sun, Raymond Wai-Yin, et al., "Stable Anticancer Gold(III)-Porphyrin Complexes: Effects of Porphyrin Structure", Chemistry—A European Journal, vol. 16, No. 10, 2010, 3097-3113.

Sutton, J. M., et al., "Porphyrin, Chlorin, and Bacteriochlorin Isothiocyanates: Useful Reagents for the Synthesis of Photoactive Bioconjugates", Bioconjugate Chem., vol. 13, 2002, 249-263.

Swamy, Narasimha, et al., "An Estradiol-Porphyrin Conjugate Selectively Localizes Into Estrogen Receptor-Positive Breast Cancer Cells", Bioorganic & Medicinal Chemistry, vol. 10, 2002, 3237-3243.

Swamy, Narasimha, et al., "Nuclear Estrogen Receptor Targeted Photodynamic Therapy: Selective Uptake and Killing of MCF-7 Breast Cancer Cells by a C17a-Alkynylestradiol-Porphyrin Conjugate", Journal of Cellular Biochemistry, vol. 99, 2006, 966-977.

Theodossiou, Theodossis A., et al., "Photochemical Internalization of Tamoxifens Transported by a Trojan-Horse Nanoconjugate into Breast-Cancer Cell Lines", Angew. Chem. Int. Ed., vol. 54, 2015, 4885-4889.

Thiabaud, Gregory, et al., "Activation of Platinum(IV) Prodrugs By Motexafin Gadolinium as a Redox Mediator", Angew. Chem. Int. Ed., vol. 55, 2016, 1-6.

Tomanova, Pavla, et al., "Konjugaty Porfyrinu", Chem. Listy, vol. 108, 2014, 843-852.

Tomanova, Pavla, et al., "Trilobolide-porphyrin conjugates: On synthesis and biological effects evaluation", Steroids, vol. 97, 2015, 8-12.

Tome, Joao P.C., et al., "Synthesis and anti-bacterial activity of new poly-S-lysine-porphyrin conjugates", J. Med. Chem., vol. 47, 2004, 6649-6652.

Wei, Guangcheng, et al., "Photothermal and photodynamic therapy reagents based on rGO-C6H4-COOH", RSC Adv., vol. 6, 2016, 3748-3755.

Yao, Ya-Hong, et al., "Novel porphyrin-Schiff base conjugates: synthesis, characterization and in vitro photodynamic activities", RSC Adv., vol. 6, 2016, 45681-45688.

Yao, Ya-Hong, et al., "Synthesis of Novel Porphyrin Derivatives and Their Cytotoxic Activities against A431 Cells", Helv. Chim. Acta, vol. 99, 2016, 24-29.

Zhai, LE, et al., "Porphyrin-vancomycin: A highly promising conjugate for the identification and photodynamic inactivation of antibiotic resistant Gram-positive pathogens", Dyes and Pigments, vol. 120, 2015, 228-238.

Zhang, Jing-Xiang, et al., "Comparative Studies of the Cellular Uptake, Subcellular Localization, and Cytotoxic and Phototoxic Antitumor Properties of Ruthenium(II)-Porphyrin Conjugates with Different Linkers", Bioconjugate Chem., vol. 23, 2012, 1623-1638.

Zhang, Jing-Xiang, et al., "Two-photon induced luminescence, singlet oxygen generation, cellular uptake and photocytotoxic properties of amphiphilic Ru(II) polypyridyl-porphyrin conjugates as potential bifunctional photodynamic therapeutic agents", Org. Biomol. Chem., vol. 9, 2011, 6004-6010.

Berenbaum, M. C., et al., "Selectivity of meso-Tetra(hydroxyphenyl)porphyrins and Chlorins and of Photofrin II in Causing Photodamage in Tumour, Skin, Muscle and Bladder. The Concept of Cost-benefit in Analysing the Results", Lasers in Medical Science, vol. 8, 1993, 235-243.

Biessen, Erik A. L., et al., "Synthesis of Cluster Galactosides with High Affinity for the Hepatic Asialoglycoprotein Receptor", J. Med. Chem., vol. 38, 1995, 1538-1546.

Bonnett, Raymond, et al., "Hydroporphyrins of the meso-tetra(hydroxyphenyl)porphyrin series as tumour photosensitizers", Biochem. J., vol. 261, 1989, 277-280.

Ivanenkov, Yan A., "Synthesis and biological evaluation of novel doxorubicin-containing ASGP-R-targeted drug-conjugates", Bioorganic & Medicinal Chemistry Letters, vol. 28, Issue 3, 2017, 503-508.

(56) References Cited

OTHER PUBLICATIONS

Lesniewska-Kowiel, Monika A., "Strategies in the designing of prodrugs, taking into account the antiviral and anticancer compounds", European Journal of Medicinal Chemistry, vol. 129, 2017, 53-71.

Zhao, Ping, et al., "Novel porphyrin-daunomycin hybrids: Synthesis and preferential binding to G-guadruplexes over i-motif", Spectrochimica Acta Part A: Molecular and Biomolecular Spectroscopy vol. 137, 2015, 227-235.

Brunner, Henri, et al., "Carboplatin-containing porphyrin-platinum complexes as cytotoxic and phototoxic antitumor agents", Inorganica Chimica Acta, vol. 357, 2004, 4423-4451.

Zhoufeng, Wang, et al., "Research on Synthesis of Porphyrins", Progress in Chemistry, vol. 19, No. 4, 2007, 520-526.

PORPHYRIN COMPOUNDS AND COMPOSITIONS USEFUL FOR TREATING CANCER

CROSS-REFERENCE TO RELATED APPLICATIONS

This application is a continuation of International Patent Application No. PCT/US2017/037982, entitled "Porphyrin Compounds and Compositions Useful for Treating Cancer", filed Jun. 16, 2017, which claims priority to and the benefit of the filing of U.S. Provisional Patent Application No. 62/351,165 entitled "Composition for Treating Cancer and Method of Use", filed on Jun. 16, 2016, and the specification and claims thereof are incorporated herein by reference.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

COPYRIGHTED MATERIAL

Not Applicable.

BACKGROUND OF THE INVENTION

Macrocyclic structures having multiple pyrrole rings joined in a macrocycle are dynamic molecules involved in many biological processes, including oxygen and electron transport. Porphyrins are natural pigments comprised of four pyrrole rings connected via four methine (=CH—) carbons to form an aromatic macrocycle. The IUPAC system is used in numbering positions in a porphyrin. There are a total of 24 positions in the porphyrin ring, including the nitrogen atoms. Carbon atoms are assigned numbers 1-20, starting at the a position, and going around the periphery of the entire heterocycle. α positions are assigned numbers 1, 4, 6, 9, 11, 14, 16 and 19, whereas β positions are assigned numbers 2, 3, 7, 8, 12, 13, 17 and 18. The meso positions (carbon atoms at the methine bridges) are numbered 5, 10, 15, and 20. The nitrogen atoms on the other hand are numbered 21, 22, 23 and 24.

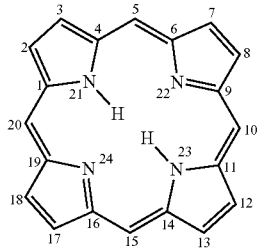

Formula I

Some porphyrins are isolated from natural sources, for example, protoporphyrin IX is the organic portion of iron-containing porphyrin hemin. Many other porphyrins are prepared synthetically. These include those made via the condensation of aldehydes and pyrroles, such as tetraphenylporphyrin, made from the condensation of benzaldehyde and pyrrole. Some porphyrins are useful in photodynamic therapy when activated at an excitation wavelength (for example, 415 nm) for the treatment of cancer. Some cationic porphyrins demonstrate non-covalent interactions with DNA. Aside from interacting strongly with DNA, cationic porphyrins can also cleave DNA, have high photonuclease and photodynamic therapy (PDT) application, and have been found to inhibit telomerase through G-quadruplex stabilization and or to inhibit translation via binding to G-quadruplex tetra-meso (N-methyl-4-pyridyl) porphine and C14-alkyl derivative tri-meso(N-methyl-4-pyridyl), meso(N-tetradecyl-4-pyridyl) porphine (called C14). Other porphyrins have been shown to be activated by ultrasound such as the compounds described in Cancer Sci. June 2007, vol. 98; no. 6 pgs. 916-920.

Porphyrins have been shown to be taken up by cancer cells preferentially over normal cells in tissue culture experiments, animal models as well as human patients. This cancer cell selectivity is in part responsible for the utility of porphyrins in photodynamic therapy. The mechanism of porphyrin localization in tumors is not well understood. Understanding this mechanism could have important implications for improved selective delivery of porphyrin compounds to tumors and the targeted delivery of cytotoxic drugs to tumors.

A variety of cancer therapies and treatments exist such as surgical resection of solid tumors, radiation, and chemotherapy. While surgical resection and radiation is used on localized tumors, chemotherapy is often delivered systemically and impacts both cancer and non-cancer cells because the traditional chemotherapy enters both cell types; there is no preference for entering cancer cells vs. non-cancer cells. Because of this, chemotherapy is often associated with unwanted toxicity, which can even lead to death. A cancer treatment using a compound or composition that preferentially enters a cancer cell as compared to a non-cancer cell is therefore desired.

Porphyrins show higher binding to and/or internalization in cancer cells as compared to non-cancer cells. The mechanism responsible for this is poorly understood. Literature data suggests that the endocytotic pathways may be a mechanism for preferential porphyrin internalization by cancer cells. In addition, previous studies have suggested that some porphyrins interact with the low-density lipoprotein receptor (LDLR) to preferentially enter cancer cells vs. non-cancer cells. Based upon this information, designing porphyrin compounds that take advantage of an LDLR interaction (or other to be identified endocytosis-related receptors) could improve the activity of porphyrin compounds used to treat cancer cells.

BRIEF DESCRIPTION OF THE PRESENT INVENTION

One embodiment of the present invention comprises a compound of formula III

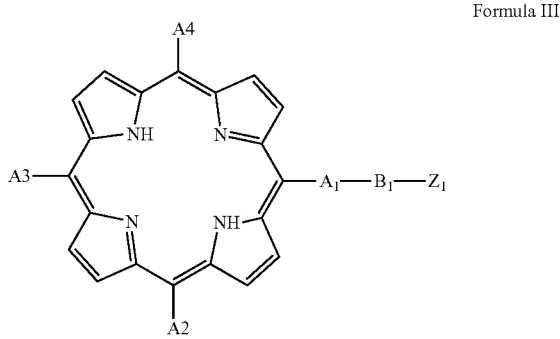

Formula III or a salt thereof, wherein an $A_1$, A2, A3 and A4 are each covalently attached to a porphyrin ring and $A_1$, A2, A3, and A4 are independently selected from a substituted aromatic ring or a six-membered heteroaromatic ring containing a single nitrogen atom at the 2, 3 or 4 position relative to the porphyrin ring;

$B_1$ is selected from the group consisting of L9-L16 wherein n is selected from 1-12; and $Z_1$ is a cytotoxic agent selected from the group consisting of T1b, T2b, T3b, T4b, 1, T1a, T3a, T4a, T8a, T10a, T14a, T15a, T18a, T19a, T21a, T27a, T31a, T32a, T33a, T4c, T5c, T9c, and T10c and derivatives thereof.

The substituted aromatic ring of the $A_1$ of the Formula III compound or a salt thereof may comprise a carboxylic amide functional group at either an ortho, meta, or para position with respect to the porphyrin ring and wherein A2, A3 and A4 are each a substituted aromatic ring wherein each A2, A3, and A4 substituted aromatic ring has a substituent at either a ortho, meta or para position with respect to the porphyrin ring and the substituent is either a carboxylic acid or carboxylic methyl ester. For example, the substituted aromatic ring of the A2, A3, and A4 of the Formula III compound or a salt thereof comprises a carboxylic methyl ester in a para position with respect to the porphyrin ring and the carboxylic amide of $A_1$ is in the para position with respect to the porphyrin ring.

In one embodiment of the present invention, the $B_1$ of the Formula III compound or a salt thereof is L11 or L13.

In one embodiment of the present invention, the $Z_1$ of the Formula III compound or a salt thereof is selected from the group consisting of T1b, 1 and T4c.

In another embodiment of the present invention, the substituted aromatic ring of the $A_1$ Formula III compound or salt thereof comprises an aromatic ether functional group at either an ortho, meta or para position with respect to the porphyrin ring, and wherein A2, A3 and A4 are each the substituted aromatic ring wherein each A2, A3, and A4 substituted aromatic ring has a substituent located at an ortho, meta or para position with respect to the porphyrin ring wherein the substituent on each A2, A3, and A4 substituted aromatic ring is independently selected from the group consisting of: lower alkyl, branched lower alkyl, cycloalkyl, halogens (F, Cl, Br, I), cyano, amino or substituted amino, sulfonic acid or sulfonamide, aromatic ether, aromatic hydroxyl, carboxylic acid alkyl esters or carboxylic acid amide.

In one embodiment of the present invention, the $B_1$ of the Formula III compound or a salt thereof is selected from the group consisting of: L9, L10, L15, and L16.

In one embodiment of the present invention, a substituent of the substituted aromatic ring at position A2, A3 and A4 of the Formula III compound or a salt thereof is a hydroxyl and may occupy the ortho, meta or para position with respect to the porphyrin ring and $B_1$ is L9 or L15.

In one embodiment of the present invention, the substituted aromatic ring $A_1$ of the Formula III compound or a salt thereof comprises an aromatic ether functional group, where the position of the aromatic ether is meta with respect to the porphyrin ring, and wherein A2, A3 and A4 are each the substituted aromatic ring wherein the substituent on the substituted aromatic ring is an aromatic hydroxyl in the meta position with respect to the porphyrin ring, $B_1$ is L9 or L15 and $Z_1$ is selected from the group consisting of: T1b, 1 and T4c.

In one embodiment of the present invention, the six-membered heteroaromatic ring of $A_1$ of the Formula III compound or a salt thereof comprises a nitrogen atom where a position of the nitrogen atom on the six-membered heteroaromatic ring may occupy one of a 2, 3 or 4 position with respect to the porphyrin ring, A2, A3 and A4 are each a pyridine ring where the position of a pyridine nitrogen on each pyridine ring of A2, A3 and A4 may independently occupy one of the 2, 3 or 4 position with respect to the porphyrin ring. Further still $B_1$ is selected from the group consisting of: L9, L10, L15, and L16. In one example, the six-membered heteroaromatic ring comprising the nitrogen atom at $A_1$ is a pyridinium where the position of the nitrogen is in the 4 position with respect to the porphyrin ring, $B_1$ is L9 or L15, and $Z_1$ is selected from the group consisting of T1b, 1 or T4c. Further still, $B_1$ is L9.

In one embodiment of the present invention the Formula III compound or a salt thereof is selected from the group consisting of: OS002, OS007, OS009, OS0030, OS0032 and OS0035.

In one embodiment of the present invention the Formula III compound or a salt thereof is selected from the group consisting of: OS0023 and OS0024.

In one embodiment of the present invention the Formula III compound or a salt thereof is selected from the group consisting of: OS0025, OS0026, OS0027, and OS0029.

Another embodiment of the present invention provides for a method of treating cancer in a patient in need thereof comprising the steps of: administering to a patient in need thereof a therapeutically effective amount of the Formula III compound or a pharmaceutically acceptable salt thereof.

Another embodiment of the present invention provides for a method of treating cancer cells in vitro comprising the steps of: administering to the cancer cells a therapeutically effective amount of the Formula III compound or a pharmaceutically acceptable salt thereof to induce cytotoxicity activity in the cancer cells preferentially as compared to non-cancer cells.

One embodiment provides for any of the Formula III compound described herein or a salt thereof, further including a pharmaceutical acceptable carrier, for example, the pharmaceutically acceptable carrier is a liquid carrier selected from the group consisting of saline, glucose, alcohols, glycols, esters, amides, and any combination thereof.

Another embodiment provides that a Formula III compound as described herein or a salt thereof is in a dosage form and the dosage form is parenteral and the dosage form is selected from the group consisting of intradermal dosage form, a subcutaneous dosage form, an intramuscular dosage form, a subcutaneous dosage form, an intravenous dosage form, an intrathecal dosage form, and an epidural dosage form. Alternatively, the dosage form is nonparenteral and the dosage form is selected from the group consisting of oral dosage form, sublingual dosage form, topical dosage form, transdermal dosage form, ophthalmic dosage form, otic dosage form, nasal dosage form, rectal dosage form, and vaginal dosage form.

In one embodiment, the salt of the Formula III compound is a pharmaceutically acceptable salt.

One embodiment of the Formula III compound or a pharmaceutically acceptable salt thereof provides is useful in the treatment of cancer.

Another embodiment of the Formula III compound of or a pharmaceutically acceptable salt thereof is useful in the treatment of cancer cells in vitro.

In one embodiment, a composition comprises a Formula III compound and a cytotoxic agent wherein the cytotoxic agent is a formula that is the same or different than $Z_1$ of the compound. For example, the different formula of the cytotoxic agent is selected from a class that is different as compared to $Z_1$ the compound.

Another embodiment of the present invention provides for a drug delivery device comprising the Formula III compound enmeshed with a biodegradable polymer. For example, the biodegradable polymer of the drug delivery device is selected from the group consisting of poly lactic co-glycolic acid, alginate, and polycaprolactone. Further still, the Formula III compound is released over time when the drug delivery device is implanted into a patient.

Another embodiment provides for a kit comprising a Formula III compound or a pharmaceutically acceptable salt thereof, and one or more pharmaceutically acceptable carriers.

Another embodiment of the present invention provides for a method of treating cancer in a patient in need thereof comprising the steps of: administering to a patient in need thereof a therapeutically effective amount of the Formula III compound or a pharmaceutically acceptable salt thereof.

One embodiment of the present invention provides a therapeutic compound comprising a therapeutically effective dose of a compound comprised of a porphyrin bound via a linker to an anti-cancer agent, sometimes referred to herein as a porphyrin anticancer conjugate ("PAC") compound. The anti-cancer agent may be selected from the group consisting of cytotoxic agent, and/or radionuclide also known as radioactive nuclide, radioisotope or radioactive isotope. For example, the anti-cancer agent may be alkylating agents, antimetabolites, anti-tumor antibiotics, antimicrotubule agents, kinase inhibitors, hormonal agents, monoclonal antibodies, glucocorticoids, mitotic inhibitors, topoisomerase I inhibitors, topoisomerase II inhibitors, immunomodulating agents, cellular growth factors, cytokines, histone deacetylase inhibitors, and nonsteroidal anti-estrogenic agents but not limited thereto. A therapeutic composition may further include a PAC compound and a pharmaceutical carrier. In one embodiment, the carrier may be an exogenous protein. In another embodiment, the carrier is not an exogenous protein.

Another embodiment provides for a method of treating cancer in a patient in need thereof comprising the steps of administering to a patient in need thereof a therapeutically effective PAC compound or composition as disclosed herein.

One aspect of the present invention provides for a method of providing two means of cell killing simultaneously via a single compound. A PAC compound will enter the cancer cell, wherein, upon exposure of the cancer cell to laser light of proper emission to excite the porphyrin, the porphyrin irreversibly damages the DNA and the anti-cancer agent acts as a cytotoxic agent in addition.

Another aspect of the present invention provides for a compound comprising a plurality of anti-cancer agents, which in combination have a synergistic therapeutic effect on a cancer cell and or patient in need of anti-cancer treatment.

Another aspect of a PAC compound as disclosed herein provides for a reduced side effect of the anti-cancer agent alone while maintaining the anti-cancer effects of the agent on the cancer cell or patient in need of anti-cancer treatment.

Another aspect of the present invention provides for a lower toxicity of the PAC compound as a treatment agent as compared to a cytotoxic agent administered individually.

In one embodiment of the present invention, the anti-cancer agent of the PAC compound does not include the following: a polyamine, polyamine analog, cyclic polyamine, cyclic polyamine analog, dioxonaphthoquinone, or dioxonaphthoquinone antitumor antibiotics, bleomycin, dactinomycin, mitoxantrone, mitomycin, epipodophyllotoxins, etoposide, teniposide, antimicrotubule agents, vinblastine, vincristine, vindesine, vinorelbine, other vinca alkaloids, taxanes, paclitaxel (taxol), docetaxel (taxotere), nitrogen mustards, chlorambucil, cyclophosphamide, estramustine, ifosfamide, mechlorethamine, melphalan, aziridines, thiotepa, alkyl sulfonates, busulfan, nitrosoureas, carmustine, lomustine, and streptozocin, platinum complexes, carboplatin cisplatin, alkylators, altretamine, dacarbazine, procarbazine, temozolamide, folate analogs, methotrexate, purine analogs, fludarabine, mercaptopurine, thiogaunine, adenosine analogs, cladribine, pentostatin, pyrimidine analogs, capecitabine, cytarabine, floxuridine, fluorouracil, gemcitabine, substituted ureas, hydroxyurea, camptothecin analogs, irinotecan and topotecan, topoisomerase I inhibitors, topoisomerase II inhibitors, and quinone compounds.

Another aspect of an embodiment the present invention provides for a PAC compound that is taken up by cancer cells such that porphyrin fluorescence as measured from the cancer cells is greater by a factor of 2 or more as compared to non-cancer cells when both are exposed to a wavelength of light that excites the porphyrin and or sound wave that excites the porphyrin.

Another aspect of the present invention provides for treatment of a subject with a PAC compound having the formula Pn-Ln-Tn wherein Pn is a porphyrin, and wherein n is selected from 1-4, Ln is a linker, and wherein n is selected from 1-15 and Tn is an anti-cancer agent, and wherein n is 1(a)-33(a) or 1(b)-4(b) or Tn is 1. The PAC compound can be used in combination with photodynamic therapy and/or radiation therapy to treat a subject with cancer or cancer cells in-vitro.

Another aspect of one embodiment of the present invention provides a PAC compound that when introduced into a cell provides a first cytotoxic agent and a second cytotoxic agent that may work synergistically, for example to produce a synthetic lethal mutation in the cell.

Another aspect of the present invention provides a method to treat a cancer cell in-vitro or in-vivo or tumor in vivo by providing a PAC compound to the cancer cell or tumor, treating the cancer cell or tumor with one or more of the following: phototherapy of a wavelength of light to excite the porphyrin of the PAC compound, the sound of the frequency to activate the porphyrin of the PAC compound, in combination with the anti-cancer agent on the PAC compound.

Another aspect of the present invention provides for a method to treat a cancer cell comprising delivering a PAC compound to the cancer cell wherein the porphyrin and the anti-cancer agent act to kill the cancer cell via synthetic lethality. In another embodiment, the use of a PAC compound as disclosed herein is provided in the absence of phenothiazine-derived drug such as chlorpromazine.

In one embodiment of the present invention, the cytotoxic agent (Tn) of the general formula Pn-Ln-Tn is not selected from the group consisting of antitumor antibiotics, bleomycin, dactinomycin, mitoxantrone, mitomycin, epipodophyllotoxins, etoposide, teniposide, antimicrotubule agents, vinblastine, vincristine, vindesine, vinorelbine, other vinca alkaloids, taxanes, paclitaxel (taxol), docetaxel (taxotere), nitrogen mustards, chlorambucil, cyclophosphamide, estramustine, ifosfamide, mechlorethamine, melphalan, aziridines, thiotepa, alkyl sulfonates, busulfan, nitrosoureas, carmustine, lomustine, and streptozocin, platinum complexes, carboplatin cisplatin, alkylators, altretamine, dacarbazine, procarbazine, temozolamide, folate analogs, methotrexate, purine analogs, fludarabine, mercaptopurine, thiogaunine, adenosine analogs, cladribine, pentostatin, pyrimidine analogs, capecitabine, cytarabine, floxuridine, fluorouracil, gemcitabine, substituted ureas, hydroxyurea, camptothecin analogs, irinotecan and topotecan, topoisomerase I inhibitors, and topoisomerase II inhibitors.

In one embodiment of the present invention, the porphyrin (Pn) of the general formula Pn-Ln-Tn is not one of the following: mesoporphyrins, deuteroporphyrins, hematoporphyrins, protoporhyrins, uroporphyrins, coproporphyrins, cytoporphyrins, rhodoporphyrin, pyrroporphyrin, etioporphyrins, phylloporphyrins, heptacarboxyporphyrins, hexacarboxyporphyrins, pentacarboxyporphyrins, and other alkylcarboxyporphyrins.

In another embodiment the PAC compound does not include one the following combinations: direct conjugation of mesoporphyrin IX to doxorubicin via an amide bond; a conjugate between colchicine-like toxin trilobolide and a tetrarryl zinc porphyrin using a 'click' linker; Cytotoxic ruthenium heterocycle conjugated with a porphyrin; the direct conjugates of hematoporphyrin IX with platinum drugs such as cisplatin or carboplatin; a direct conjugation of emodin to aryl porphyrins; a conjugation of an aryl porphyrin to retinoic acid via a PEG amide linker; a direct conjugate of the alkaloid brucine with aryl porphyrins; a conjugate of fluorouracil with meta-phenolic porphyrins using an ether linkage and direct conjugation to a kinase inhibitor.

Embodiments of the present invention relate to methods of treating cancer in a subject in need thereof and a PAC compound for the use in treating cancer in a subject in need thereof. Another embodiment provides for a method of treating cancer cells and a PAC compound for the use in treating cancer cells in-vitro.

Objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims (if any).

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF THE INVENTION

Figure 1:
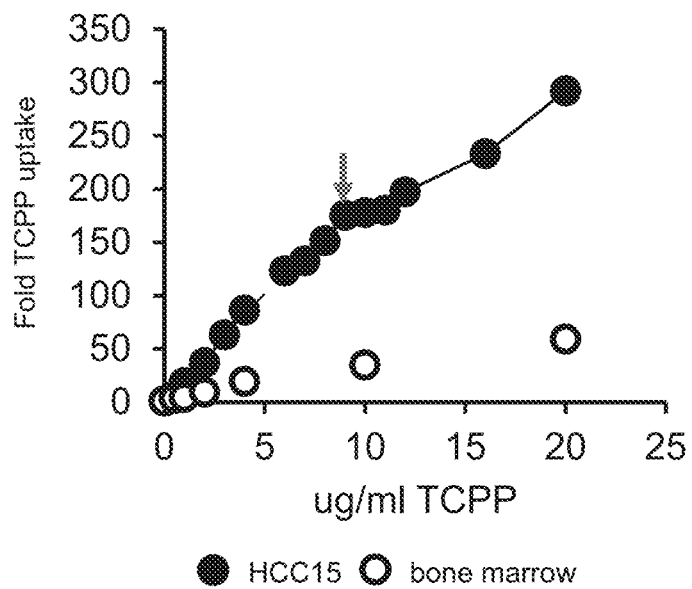
FIG. 1 illustrates TCPP uptake preferentially is cancer cells vs. non-cancer cells.

Furthermore, the following terms shall have the definitions set out below. It is understood that in the event a specific term is not defined herein below, that term shall have a meaning within its typical use within context by those of ordinary skill in the art.

It is to be noted that as used herein and in the appended claims, the singular forms "a," "and" and "the" include plural references unless the context clearly dictates otherwise.

The term "anti-cancer agent" includes cytotoxic agents, which may be selected from antineoplastic and immunomodulating agents such as but not limited to, 1) Immunosuppressants including: Pomalidomide, Pirfenidone, Lenalidomide, Methotrexate, Thalidomide, Azathioprine; 2) Calcineurin Inhibitors including: Voclosporin, Tacrolimus, Ciclosporin, Cyclosporine; 3) Interleukin Inhibitors including: Brodalumab, Siltuximab, Secukinumab, Briakinumab, Canakinumab, Tocilizumab, Mepolizumab, Ustekinumab, Rilonacept, Anakinra, Basiliximab, Daclizumab; 4) Tumor Necrosis Factor alpha (tnf-a) Inhibitors including: Golimumab, Certolizumab pegol, Adalimumab, Afelimomab, Infliximab, Etanercept; 5) Selective Immunosuppressants including: Begelomab, Alemtuzumab, Vedolizumab, Apremilast, Teriflunomide, Tofacitinib, Belatacept, Fingolimod, Belimumab, Eculizumab, Abatacept, Natalizumab, Abetimus, Efalizumab, Gusperimus, Everolimus, Alefacept, Leflunomide, Sirolimus, Mycophenolic acid, Antithymocyte immunoglobulin (rabbit), Antilymphocyte immunoglobulin (horse), Muromonab; 6) Immunostimulants including: Dasiprotimut, Cridanimod, Sipuleucel-T, Plerixafor, Mifamurtide, Histamine dihydrochloride, Glatiramer Acetate, Melanoma vaccine, Tasonermin, Immunocyanin, Thymopentin, Pidotimod, Pegademase, Bcg vaccine, Roquinimex, Lentinan; 7) Interleukins including: Oprelvekin, Aldesleukin; 8) Interferons including: Peginterferon alfa-2a, Peginterferon alfa-2b, Cepeginterferon alfa-2b, Peginterferon beta-1a, Peginterferon beta-1a, Albinterferon alfa-2b, Albumin-interferon alpha, Peginterferon alpha 2a, Peginterferon alpha 2b, Interferon alfacon-1, Interferon beta-1b, Interferon beta-1a, Interferon alfa-nl, Interferon Alfa-2b Recombinant, Interferon Alfa-2a-Recombinant, Interferon gamma, Interferon beta natural, Interferon alfa natural; 9) Colony stimulating factors including: Balugrastim, Lipegfilgrastim, Pegfilgrastim, Ancestim, Pegfilgrastim, Ancestim, Lenograstim, Pegfilgrastim, Sargramostim, Molgramostin, Filgrastim; 10) Hormone Antagonists and related agents including: Abiraterone, Degarelix, Abarelix, Exemestane, Letrozole, Anastrozole, Formestane, Aminoglutethimide, Enzalutamide, Bicalutamide, Nilutamide, Flutamide, Fulvestrant, Toremifene, Tamoxifen; 11) Hormones and Related Agents including: Histrelin, Triptorelin, Goserelin, Leuprolide, Buserelin; 12) Progestogens including: Gestonorone, Medroxyprogesterone, Megestrol; 13) Estrogens including: Fosfesterol, Ethinylestradiol, Ethinyl Estradiol, Polyestradiol phosphate, Diethylstilbestrol; 14) Antineoplastic Agents including: Ixazomib, Belinostat, Sonidegib, Idelalisib, Olaparib, Carfilzomib, Aflibercept, Vismodegib, Panobinostat, Eribulin, Homoharringtonine, Romidepsin, Vorinostat, EG009, Oblimersen, Anagrelide, Celecoxib, Bortezomib, Denileukin difitox, Arsenic trioxide, Bexarotene, Pegaspargase, Mitotane, Alitretinoin, Irinotecan, Topotecan, Tretinoin, Estramustine, Masoprocol, Miltefosine, Pentostatin, Lonidamine, Hydroxycarbamide, Hydroxyurea, Altretamine, Asparaginase, Amsacrine, Tivozanib, Palbociclib, Cediranib, Nintedanib, Lenvatinib, Ceritinib, Ibrutinib, Cabozantinib, Trametinib, Ponatinib, Dabrafenib, Masitinib, Regorafenib, Ruxolitinib, Axitinib, Crizotinib, Vemurafenib, Bosutinib, Afatinib, Vandetanib, Pazopanib, Everolimus, Temsirolimus, Nilotinib, Lapatinib, Dasatinib, Sorafenib, Sunitinib, Erlotinib, Gefitinib, Imatinib; 15) Sensitizers used in photodynamic/radiation therapy including: Efaproxiral, Temoporfin, Aminolevulinic acid, Methyl aminolevulinate, Porfimer; 16) Monoclonal antibodies including: Necitumumab, Ramucirumab, Blinatumomab, Pembrolizumab, Nivolumab, Dinutuximab, Obinutuximab, Ado-trastuxumab emtansane, Pertuzumab, Brentuximab vedotin, Ipilimumab, Ofatumumab, Catumaxomab, Panitumumab, Bevacizumab, Cetuximab, Gemtuzumab, Trastuzumab, Rituximab, Edrecolomab, Methylhydrazines, Procarbazine, Platinum compounds, Polyplatillen, Satraplatin, Oxaliplatin, Carboplatin, Cisplatin; 17) Cytotoxic antibodies and related substances including: Ixabepilone, Mitomycin, Plicamycin, Bleomycin; 18) Anthracyclines and related substances including: Pixantrone, Amrubicin, Valrubicin, Pirarubicin, Mitoxantrone, Idarubicin, Zorubicin, Aclarubicin, Epirubicin, Daunorubicin, Doxorubicin; 19) Actinomycines including: Dactinomycin; 20) Plant Alkaloids and other natural products including: Trabectedin; 21) Taxanes including: Cabazitaxel, Docetaxel, Paclitaxel; 22) Colchicine Derivatives including: Demecolcine; 23) Podophyllotoxin derivatives including Teniposide, Etoposide; 24) Vinca alkaloids and analogues including: Vintafolide, Vinflunine, Vinorelbine, Vindesine, Vincristine, Vinblastine; 25) Pyrimidine analogues including: Trifluridine, Tegafur, Fluorouracil, Decitabine, Azacitidine, Capecitabine, Gemcitabine, Carmofur, Tegafur, Fluorouracil, Cytarabine; 26) Purine analogues including: Nelarabine, Clofarabine, Fludarabine, Cladribine, Tioguanine, Mercaptopurine, Pralatrexate, Pemetrexed, Raltitrexed, Methotrexate; 27) Other alkylating agents including: Dacarbazine, Temozolomide, Pipobroman, Mitrobronitol; 28) Epoxides including: Etoglucid; 29) Nitrosoureas including: Ranimustine, Nimustine, Fotemustine, Streptozocin, Semustine, Lomustine, Carmustine; 30) Ethylene imines including: Carboquone, Triaziquone, Thiotepa; 31) Alkyl sulfonates including: Mannosulfan, Treosulfan, Busulfan; 32) Nitrogen mustard analogues including: Bendamustine, Prednimustine, Trofosfamide, Ifosfamide, Mechlorethamine, Melphalan, Chlorambucil, Cyclophosphamide and derivatives and analogs of the cytotoxic agents disclosed. The antineoplastic and immunomodulating agents may be classified as microtubule-stabilizing agents, microtubule-disruptor agents, alkylating agents, antimetabolites, epidophyllotoxins, antineoplastic enzymes, topoisomerase inhibitors, inhibitors of cell cycle progression, antisense molecules, toxins and platinum coordination complexes.

As used herein, an "anticancer therapeutic effect" includes one or more of the following: inhibition of cancer cell growth, increased cancer cell death (a tumoricidal reaction), reduction in tumor invasiveness, reduction in overall tumor burden, reduction in local tumor burden, reduction in size of the primary tumor, prevention of metastases, reduction in the number of metastases, reduction in the size of metastases, and prolonged life. While it is desired that the treatment render the subject free of disease, it is not intended that the present invention be limited to curing cancer. There is therapeutic benefit even if the cancer is simply slowed in its progression. It is not intended that the present invention be limited to the magnitude of the effect. For example, the reduction in size of the primary tumor (or of metastases) can be as little as a 10% reduction or as great as a 90% reduction (or more). It is also not intended that the present invention be limited to the duration of the anticancer therapeutic effect. The treatment (using the various embodiments described herein) may result in only temporary inhibition of cancer cell growth, temporary increased cancer cell death, temporary reduction in tumor invasiveness, temporary reduction in overall tumor burden, temporary reduction in local tumor burden, temporary reduction in size of the primary tumor, temporary prevention of metastases, temporary reduction in the number of metastases, or temporary reduction in the size of metastases. The temporary effects may last weeks to months, or months to years. These parameters are relatively easy to measure (e.g., by monitoring the size of the primary tumor(s) and metastases over time). With respect to prevention of metastases and prolonging life, these parameters may be measured against patient population data for the particular tumor type, stage, and the like. As used herein, a "cancer preventative effect" or "protective effect" comprises an effect that reduces the incidence of new cancers. This parameter can be proved in animals and measured in humans on a population basis.

The term "bioavailability" refers to the systemic availability (i.e., blood/plasma levels) of a cytotoxic agent administered to a patient. Bioavailability is an absolute term that indicates measurement of both the time (rate) and total amount (extent) of drug that reaches the general circulation from an administered dosage form.

The term "cytotoxic activity" refers to a cell-killing, a cytostatic or an anti-proliferative effect of a porphyrin anti-cancer agent conjugate or an intracellular metabolite of a Drug Linker Ligand conjugate. Cytotoxic activity may be expressed as the $IC_{50}$ value in cells, which is the concentration (molar or mass) per unit volume at which half the cells die and/or the $IC_{10}$ value in animals, which is the concentration (molar or mass) per unit volume at which 10% of the animals die. Light induced porphyrin cytotoxicity occurs upon activation of porphyrin.

Cancers are classified in two ways: by the type of tissue in which the cancer originates (histological type) and by primary site, or the location in the body where the cancer first developed. From a histological standpoint there are hundreds of different cancers, which are grouped into six major categories: Carcinoma, Sarcoma, Myeloma, Leukemia, Lymphoma, Mixed Types, Central Nervous System and Mesothelioma as identified from the world wide web cancer research society website crs-src.ca last visited on May 5, 2016.

The term "cancer" is used throughout the specification to refer to a cell(s) possessing one or more of the following abnormal growth characteristics: uncontrolled proliferation, immortality, metastatic potential, rapid growth and proliferation rate, perturbed oncogenic signaling, and certain morphological characteristic features and may originate from: epithelial cell tissue (carcinomas), blood cells, bone marrow, and immune cells (leukemias, lymphomas, myelomas), connective tissue, bone, cartilage, fat, muscle, blood vessels (sarcomas), central nervous system tissue, glial or supportive cells (gliomas, blastomas CNS lymphoma), mesothelium lining (mesothelioma of lung, heart, abdominal cavity), melanoma (mesodermal origin). As used herein, the term cancer is used to describe all cancerous disease states applicable to diagnosis and treatment according to the present invention and embraces or encompasses the pathological process associated with virtually all cancers types, including carcinomas, sarcoma, myeloma, leukemia, lymphoma, mixed types. In a preferred embodiment, the cancer is a solid tumor.

Examples of cancers which may be diagnosed/treated using compounds and methods according to the present invention include, but is not limited to, carcinomas (e.g., squamous-cell carcinomas, adenocarcinomas, hepatocellular carcinomas, and renal cell carcinomas), particularly those of the bladder, bowel, breast, cervix, colon, esophagus, head, kidney, liver, lung, neck, ovary, pancreas, prostate, and stomach; and malignant lymphomas, particularly Burkitt's lymphoma and Non-Hodgkin's lymphoma; and malignant melanomas; myeloproliferative diseases; sarcomas, particularly Ewing's sarcoma, hemangiosarcoma, Kaposi's sarcoma, liposarcoma, myosarcomas, peripheral neuroepithelioma, and synovial sarcoma; tumors of the central nervous system (e.g., gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas); germ-line tumors (e.g., bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, and melanoma); mixed types of neoplasias, particularly carcinosarcoma and Hodgkin's disease; and tumors of mixed origin, such as Wilms' tumor and teratocarcinomas. For example Adrenal Cancer, Anal Cancer, Bile Duct Cancer, Bladder Cancer, Bone Cancer, Brain/CNS Tumors In Adults, Brain/CNS Tumors In Children, Breast Cancer, Breast Cancer In Men, Cancer in Adolescents, Cancer in Children, Cancer in Young Adults, Cancer of Unknown Primary, Castleman Disease, Cervical Cancer, Colon/Rectum Cancer, Endometrial Cancer, Esophagus Cancer, Ewing Family Of Tumors, Eye Cancer, Gallbladder Cancer, Gastrointestinal Carcinoid Tumors, Gastrointestinal Stromal Tumor (GIST), Gestational Trophoblastic Disease, Hodgkin Disease, Kaposi Sarcoma, Kidney Cancer, Laryngeal and Hypopharyngeal Cancer, Liver Cancer, Lung Cancer, Lung Cancer—Non-Small Cell, Lung Cancer—Small Cell, Lung Carcinoid Tumor, Lymphoma, Lymphoma of the Skin, Malignant Mesothelioma, Multiple Myeloma, Myelodysplastic Syndrome, Nasal Cavity and Paranasal Sinus Cancer, Nasopharyngeal Cancer, Neuroblastoma, Non-Hodgkin Lymphoma, Non-Hodgkin Lymphoma In Children, Oral Cavity and Oropharyngeal Cancer, Osteosarcoma, Ovarian Cancer, Pancreatic Cancer, Penile Cancer, Pituitary Tumors, Prostate Cancer, Retinoblastoma, Rhabdomyosarcoma, Salivary Gland Cancer, Sarcoma—Adult Soft Tissue Cancer, Skin Cancer, Skin Cancer—Basal and Squamous Cell, Skin Cancer—Melanoma, Skin Cancer—Merkel Cell, Small Intestine Cancer, Stomach Cancer, Testicular Cancer, Thymus Cancer, Thyroid Cancer, Uterine Sarcoma, Vaginal Cancer, Vulvar Cancer, Waldenstrom Macroglobulinemia, Wilms Tumor may be the subject of treatment with one or more of the compositions as disclosed herein.

The term "compound", as used herein, unless otherwise indicated, refers to any specific chemical compound disclosed herein. In certain instances, the term may also refer to stereoisomers and/or optical isomers (including racemic mixtures) or enantiomerically enriched mixtures of disclosed compounds. In certain instances, the term may also refer to salts, metabolites, prodrugs, crystals, polymorphs, analogues, solvates and hydrates.

It should be recognized that compounds referred to herein can contain chiral carbon atoms. In other words, it may have optical isomers or diastereoisomers. Compounds may also include salts and their polymorphs. Further a composition may exist as any combination of the compounds.

The term "cytotoxic agent" as used herein refers to a substance that inhibits the function of cells and/or causes destruction of cells wherein the term cytotoxic agents includes cytostatic agents. The term is intended to include radioactive isotopes (e.g., $^{211}$At, $^{131}$I, $^{125}$I, $^{90}$Y, $^{186}$Re, $^{188}$Re, $^{153}$Sm, $^{212}$Bi, $^{32}$P, $^{60}$C, and radioactive isotopes of Lu), and toxins such as small molecule toxins or enzymatically active toxins of bacterial, fungal, plant or animal origin, including synthetic analogs and derivatives thereof. In one aspect, the term does not include a radionuclide.

A cytotoxic agent may be covalently appended to porphyrins with a suitable linker and include solubilizing linkers which include for example polyethylene glycol (PEG) moieties but not limited thereto and wherein the cytotoxic agent in one embodiment include those identified in Table 6, Table 7 and Table 8 and dolastatins, e.g., dolastatin 10, dolastatin 15, monomethylauristatin E, monomethylauristatin F, tasidotin, cemadotin.

The term "effective" is used herein, unless otherwise indicated, to describe an amount of a compound or composition which, in context, is used to produce an intended result, whether that result relates to the treatment of a cancer in a patient or subject or with cells in-vitro. The term effective subsumes all other effective amount or effective concentration terms, which are otherwise described or used in the present application. In the case of cancer, the effective amount of the composition may reduce the number of cancer cells; reduce the tumor size; reduce the number of tumor sites, inhibit (i.e., slow to some extent or stop) cancer cell infiltration into adjacent and or distal tissues.

The term "linker" is used throughout the specification within context to describe a covalent moiety that attaches a porphyrin and an anti-cancer agent, for example covalently. A wide variety of linkers can be used, and according to one embodiment, the invention is not limited by the type of linker used. Examples of linkers include, but are not limited to, substituted and unsubstituted $C_1$-$C_{12}$ alkyl, alkenyl, and alkynyl groups, $C_1$-$C_{12}$ heteroalkyl, heteroalkenyl, and heteroalkynyl groups, and $C_6$-$C_{20}$ aryl-containing and heteroaryl-containing linking groups and L9-L16.

The term "patient" or "subject" is used throughout the specification within context to describe an animal, especially including a domesticated mammal and preferably a human, to whom a treatment or procedure is performed. For treatment of those conditions or disease states which are specific for a specific animal such as a human patient, the term patient refers to that specific animal. In most instances, the patient or subject of the present invention is a domesticated/agricultural animal or human patient of either or both genders.

The term "pharmaceutically acceptable salt" refers to salts derived from a variety of organic and inorganic counter ions well known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, trifluoroacetyl and ethanolamine. In some embodiments, the pharmaceutically acceptable base addition salt is chosen from ammonium, potassium, sodium, calcium, and magnesium salts.

The term "alkyl" refers to saturated aliphatic groups including straight-chain, branched-chain, cyclic groups, and combinations thereof, having the number of carbon atoms specified, or if no number is specified, having up to 12 carbon atoms. "Straight-chain alkyl" or "linear alkyl" groups refer to alkyl groups that are neither cyclic nor branched, commonly designated as "n-alkyl" groups. Examples of alkyl groups include, but are not limited to, groups such as methyl, ethyl, n-propyl, isopropyl, butyl, n-butyl, isobutyl, sec-butyl, t-butyl, pentyl, n-pentyl, hexyl, heptyl, octyl, nonyl, decyl, undecyl, dodecyl, neopentyl, cyclopropyl, cyclobutyl, cyclopentyl, cyclohexyl, and adamantyl. Branched-chain groups would include, but not be limited to, isopropyl, isobutyl, neopentyl, tertiary butyl and tertiary amyl. Cyclic groups can consist of one ring, including, but not limited to, groups such as cyclopropyl, cyclobutyl, cyclopentyl, cyclohexyl, cycloheptyl, or multiple fused rings, including, but not limited to, groups such as adamantyl or norbornyl. Preferred subsets of alkyl groups include $C_1$-$C_{12}$, $C_1$-$C_{10}$, $C_1$-$C_8$, $C_1$-$C_6$, $C_1$-$C_4$, $C_1$-$C_2$, $C_3$-$C_4$, $C_3$, and $C_4$ alkyl groups.

The term "Aryl" or "Ar" refers to an aromatic carbocyclic group having a single ring (including, but not limited to, groups such as phenyl, and includes both unsubstituted and substituted aryl groups. "Substituted aryls" refers to aryls substituted with one or more substituents, including, but not limited to, groups such as alkyl, halogen, alkoxy (OR), amino or alkylamino ($NH_2$, NHR, NRR'), hydroxyl, carboxy, phenyl, cyano, carboalkoxy and carboxamide, or a functionality that can be suitably blocked, if necessary for purposes of the invention, with a protecting group.

The term "alkoxy" as used herein refers to an alkyl group linked to an oxygen atom and having the number of carbon atoms specified, or if no number is specified, having up to 12 carbon atoms. Examples of alkoxy groups include, but are not limited to, groups such as methoxy, ethoxy, and t-butoxy.

The terms "halo" and "halogen" as used herein refer to Cl, Br, F or I substituents.

The terms "intracellularly cleaved" and "intracellular cleavage" refer to a metabolic process or reaction inside a cell on a PAC compound, whereby the linker, the part of the compound that connects the cytotoxic agent and the porphyrin is broken, resulting in the free cytotoxic agent, or other metabolite of the conjugate dissociated from the porphyrin inside the cell. The cleaved moieties of PAC compounds are thus intracellular metabolites.

In addition to the treatment of cancers as described above, the present invention also may be used preferably to treat cancers such as choriocarcinoma, testicular choriocarcinoma, non-seminomatous germ cell testicular cancer, placental cancer (trophoblastic tumor) and embryonal cancer, among others. In a preferred embodiment, the cancer to be treated is lung cancer.

Formulations containing the compounds according to the present invention may take the form of liquid, solid, semi-solid or lyophilized powder forms, such as, for example, solutions, suspensions, emulsions, sustained-release formulations, tablets, capsules, powders, suppositories, creams, ointments, lotions, aerosols, patches or the like, preferably in unit dosage forms suitable for simple administration of precise dosages.

Pharmaceutical compositions according to the present invention typically include a conventional pharmaceutical carrier or excipient and may additionally include other medicinal agents, carriers, adjuvants, additives and the like. Excipients include those identified on the world wide web at fda.gov and equivalents thereto as of the date of the filing of this application. The weight percentage ratio of the anti-cancer/porphyrin to the one or more excipients can be between about 20:1 to about 1:60, or between about 15:1 to about 1:45, or between about 10:1 to about 1:40, or between about 9:1, 8:1, 7:1, 6:1, 5:1, 4:1, 3:1, 2:1 or 1:1 to about 1:2, 1:3, 1:4, 1:5, 1:6, 1:7, 1:8, 1:9, 1:10, 1:15, 1:20, 1:25, 1:30, or 1:35, and preferably is about 20:1, 19:1, 18:1, 17:1, 16:1, 15:1, 14:1, 13:1, 12:1, 11:1, 10:1, 9:1, 8:1, 7:1, 6:1 or 5:1. In some embodiments, formulations of the invention comprise between about 250 mg to about 500 mg, or between about 300 mg to about 450 mg, or about 325 mg to about 425 mg of total porphyrin/anti-cancer agent and may optionally contain one or more suitable pharmaceutical excipients.

An injectable composition for parenteral administration (e.g. intravenous, intramuscular intrathecal, intraperitoneal or intracranial) will typically contain the compound in a suitable i.v. solution, such as sterile physiological salt solution. The compound may also be formulated as a suspension in an aqueous emulsion. A composition comprises a PAC compound or a pharmaceutically acceptable salt thereof and at least on pharmaceutically acceptable carrier.

Liquid compositions can be prepared by dissolving or dispersing the pharmaceutical composition comprising the PAC compound and optional pharmaceutical adjuvants, in a carrier, such as, for example, aqueous saline, aqueous dextrose, glycerol, or ethanol, to form a solution or suspension. For use in an oral liquid preparation, the composition may be prepared as a solution, suspension, emulsion, or syrup, being supplied either in liquid form or a dried form suitable for hydration in water or normal saline.

For oral administration, such excipients include pharmaceutical grades of mannitol, lactose, starch, magnesium stearate, sodium saccharine, talcum, cellulose, glucose, gelatin, sucrose, magnesium carbonate, and the like. If desired, the composition may also contain minor amounts of non-toxic auxiliary substances such as wetting agents, emulsifying agents, or buffers.

When the composition is employed in the form of solid preparations for oral administration, the preparations may be tablets, granules, powders, capsules or the like. In a tablet formulation, the composition is typically formulated with additives, e.g. an excipient such as a saccharide or cellulose preparation, a binder such as starch paste or methyl cellulose, a filler, a disintegrator, and other additives typically used in the manufacture of medical preparations.

Methods for preparing such dosage forms are known or are apparent to those skilled in the art; for example, see Remington's Pharmaceutical Sciences (17th Ed., Mack Pub. Co. 1985). The composition to be administered will contain a quantity of the selected compound in a pharmaceutically effective amount for therapeutic use in a biological system, including a patient or subject according to the present invention.

Methods of treating patients or subjects in need, for a particular disease state comprise administration of an effective amount of a pharmaceutical composition comprising therapeutic amounts of porphyrin/anti-cancer agent described herein and optionally at least one additional bioactive (e.g. anti-cancer) agent according to the present invention. The amount of porphyrin/anti-cancer agent used in the methods of treatment of the instant invention that may be combined with the carrier materials to produce a single dosage form will vary depending upon the host treated, the particular mode of administration. For example, the compositions could be formulated so that a therapeutically effective dosage of between about 0.01, 0.1, 1, 5, 10, 15, 20, 25, 30, 35, 40, 45, 50, 55, 60, 65, 70, 75, 80, 85, 90 or 100 mg/kg of patient/day or in some embodiments, greater than 100, 110, 120, 130, 140, 150, 160, 170, 180, 190 or 200 mg/kg of the novel porphyrin/anti-cancer agent can be administered to a patient receiving these compositions.

In one embodiment, a compound of Formula III

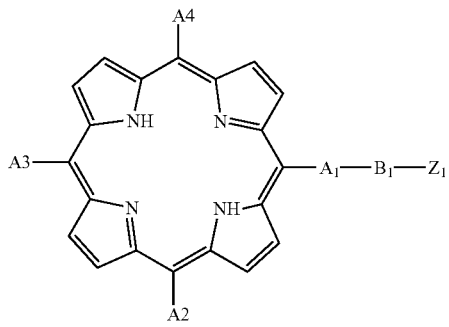

Formula III or a pharmaceutically acceptable salt, enantiomer, solvate, or polymorph thereof is provided, wherein A1-A4 each are independently selected from a substituted aromatic ring or substituted heteroaromatic ring. $B_1$ represents a covalent linker moiety which connects $A_1$ to a cytotoxic agent (also referred to herein as "cytotoxin") $Z_1$.

In a specific embodiment, $A_1$ represents an aromatic ring bearing a carboxylic amide functional group, where the position of the carboxylic amide may be ortho, meta or para with respect to the porphyrin ring and wherein the C—N bond of the carboxamide functional group serves to covalently connect $A_1$ to linker Bi. Further, A2, A3 and A4 represent mono-substituted aromatic rings wherein the substituent may independently occupy the ortho, meta or para position with respect to the porphyrin ring. The substituents on A2, A3 and A4 may independently be lower alkyl, branched lower alkyl, cycloalkyl, halogens (F, Cl, Br, I), cyano, amino or substituted amino, sulfonyl (including sulfonic acids, esters or amides), phenol, aromatic ethers (OR, where R is lower alkyl) or carbonyl (including carboxylic acids, carboxylic esters (COOR, where R is lower alkyl) or carboxylic amides. $B_1$ can be selected from the group L11-L14 (wherein $B_1$ is defined as the chemical formula between $A_1$ and $Z_1$ of Table 1). The group $Z_1$ may be a toxin of the anthracycline type (Table 2), kinase inhibitor (Table 3) or auristatin type (Table 4), respectively, bound to $B_1$ and wherein the a nitrogen atom of the cytotoxin $Z_1$ is part of a carboxamide functional group connecting $B_1$ to $Z_1$.

In a preferred embodiment, $A_1$ represents an aromatic ring bearing a carboxylic amide (carboxamide) functional group, where the position of the carboxylic amide may be ortho, meta or para with respect to the porphyrin ring. Further, A2, A3 and A4 represent mono-substituted aromatic rings wherein the substituent is a carboxylic acid, carboxylic ester or carboxylic amide and may occupy the ortho, meta or para position with respect to the porphyrin ring. $B_1$ may be selected from the group L11 or L13 (Table 1) $Z_1$ may be selected from the cytotoxins of the anthracycline, kinase inhibitor or auristatin type, respectively (Table 2-4).

In a most preferred embodiment, $A_1$ represents an aromatic ring bearing a carboxylic amide functional group, where the position of the carboxylic amide is para with respect to the porphyrin ring. Further, A2, A3 and A4 represent mono-substituted aromatic rings wherein the substituent is a carboxylic acid, or carboxylic methyl ester in the para position with respect to the porphyrin ring. $B_1$ may be selected from the group L11 or L13 (Table 1). $Z_1$ may be selected from the toxins T1b, 1 or T4c, in Table 2-4, respectively.

TABLE 1

B1 formulas

L11

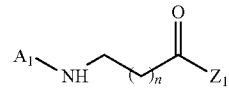

TABLE 1-continued
B1 formulas
L12 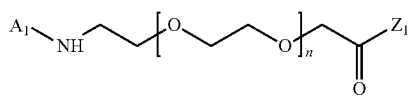
L13 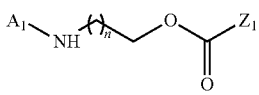
L14 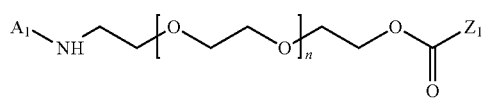
(n = 1-12)
TABLE 2
Cytotoxins Z1 (anthracycline type formulas)
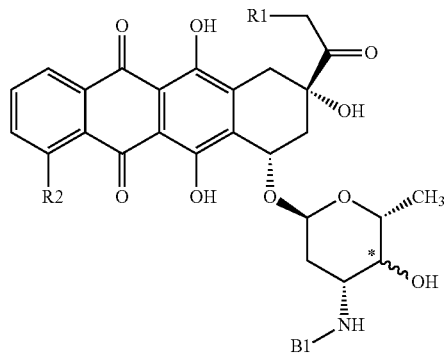
| Tnb | R1 | R2 | * |
|---|---|---|---|
| T1b | OH | OMe | R |
| T2b | H | OMe | R |
| T3b | H | H | R |
| T4b | OH | OMe | S |
TABLE 3
Cytotoxins Z1 (kinase inhibitor type formulas)
| Toxin | Structure | Parent toxin name |
|---|---|---|
| 1 | 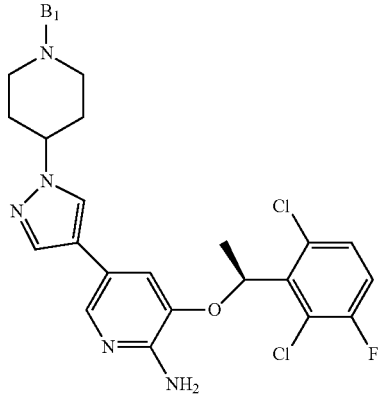 | Crizotinib |
| T1a | 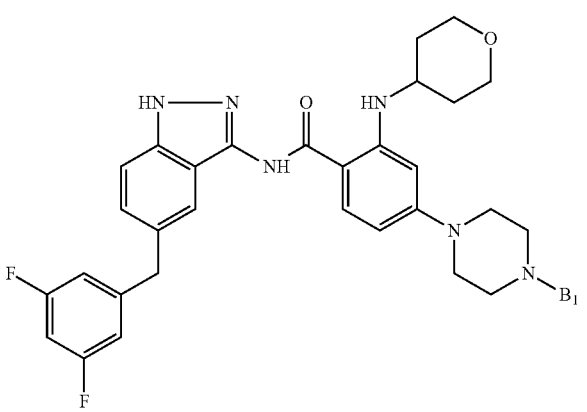 | entrecitinib |

TABLE 3-continued
Cytotoxins Z1 (kinase inhibitor type formulas)
| Toxin | Structure | Parent toxin name |
|---|---|---|
| T3a | 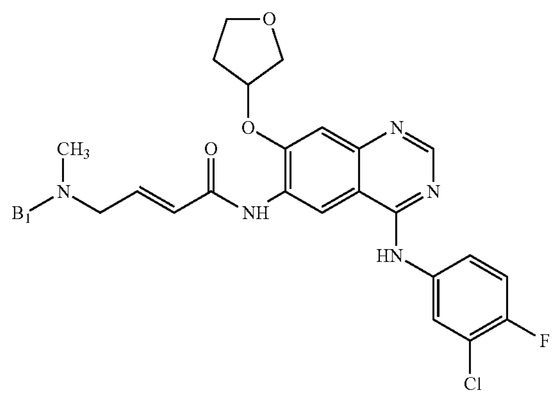 | pelitinib |
| T4a | 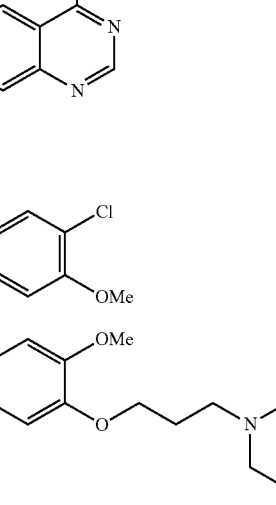 | lapatinib |
| T8a | 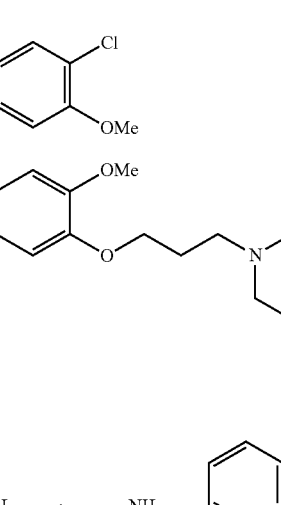 | bosutinib |
| T10a | 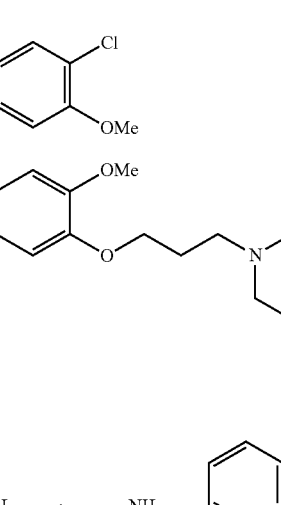 | imatinib |

TABLE 3-continued
Cytotoxins Z1 (kinase inhibitor type formulas)
| Toxin | Structure | Parent toxin name |
|---|---|---|
| T14a | 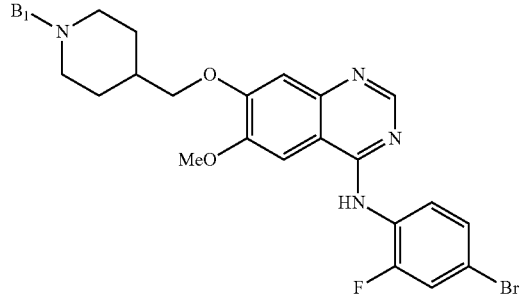 | vandetanib |
| T15a | 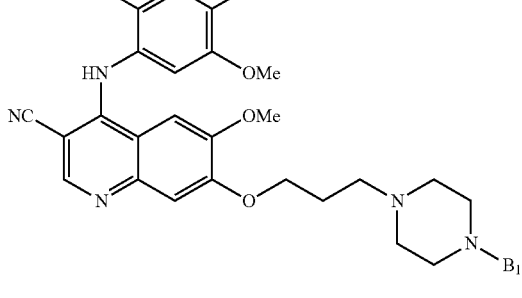 | bosutinib |
| 18a | 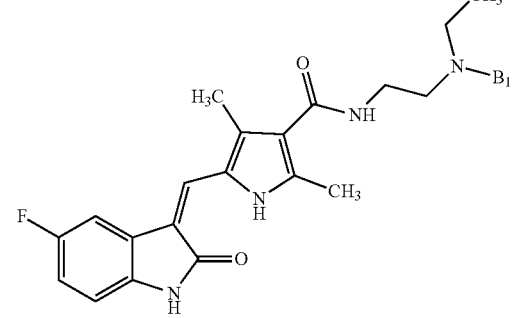 | sunutinib |
| T19a | 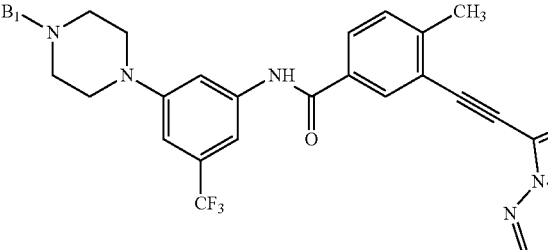 | ponatinib |

TABLE 3-continued

| Cytotoxins Z1 (kinase inhibitor type formulas) | | |
|---|---|---|
| Toxin | Structure | Parent toxin name |
| T21a | | masitinib |
| T27a | | nintedanib |
| T29a | | ceritinib |
| T31a | | palbociclib |

TABLE 3-continued

Cytotoxins Z1 (kinase inhibitor type formulas)

| Toxin | Structure | Parent toxin name |
|---|---|---|
| T32a | 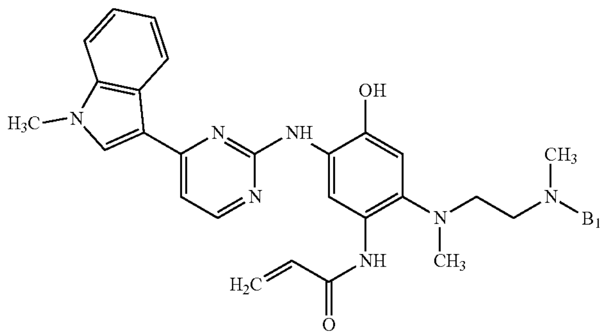 | osimertinib |
| T33a | 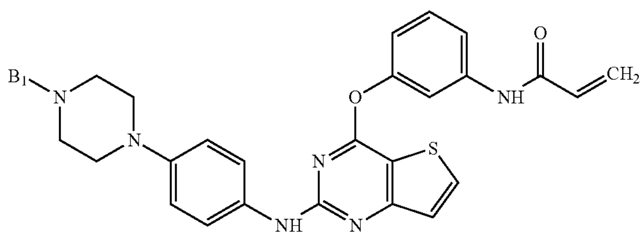 | Olmutinib |

TABLE 4

CytoToxins Z1 (auristatin type formula)

| | |
|---|---|
| | T4c |
| | T5c |
| | T9c |

TABLE 4-continued

CytoToxins Z1 (auristatin type formula)

T10c

[Chemical structure of auristatin-type cytotoxin T10c showing $B_1$ linked through N-CH$_3$ to a peptide chain containing valine, NH-CH(isopropyl)-C(=O), NH-valine-N, proline, proline, terminating in NH-Bn]

In another specific embodiment, $A_1$ represents an aromatic ring bearing an aromatic ether functional group, where the position of the aromatic ether may be ortho, meta or para with respect to the porphyrin ring. Further, A2, A3 and A4 represent mono-substituted aromatic rings wherein the substituent may independently occupy the ortho, meta or para position with respect to the porphyrin ring. The substituents on A2, A3 and A4 may independently be lower alkyl, branched lower alkyl, cycloalkyl, halogens (F, Cl, Br, I), cyano, amino or substituted amino, sulfonyl (including sulfonic acids, esters or amides), phenol or aromatic ethers (OR, where R is lower alkyl) or carbonyl (including carboxylic acids, carboxylic esters (COOR, where R is lower alkyl) or carboxylic amides). $B_1$ may be selected from the group L9, L10, L15, L16 (Table 5). $Z_1$ may be selected from the cytotoxins of the anthracycline, kinase inhibitor or auristatin type, respectively (Tables 2-4).

In a preferred embodiment, $A_1$ represents an aromatic ring bearing an aromatic ether functional group, where the position of the aromatic ether may be ortho, meta or para with respect to the porphyrin ring. Further, A2, A3 and A4 represent mono-substituted aromatic rings wherein the substituent is a phenol and may occupy the ortho, meta or para position with respect to the porphyrin ring. $B_1$ may be selected from the group L9 or L15 (Table 5). $Z_1$ may be selected from the cytotoxins of the anthracycline, kinase inhibitor or auristatin type, respectively (Tables 2-4).

In a most preferred embodiment, $A_1$ represents an aromatic ring bearing an aromatic ether functional group, where the position of the aromatic ether is meta with respect to the porphyrin ring. Further, A2, A3 and A4 represent mono-substituted aromatic rings wherein the substituent is a phenol in the meta position with respect to the porphyrin ring. $B_1$ is L9 (Table 5). $Z_1$ may be selected from the cytotoxins T1b or 1 Tables 2-3, respectively.

TABLE 5

B1 Structures

L9  [Structure: $A_1$—(CH$_2$)$_n$—C(=O)—$Z_1$]

L10 [Structure: $A_1$—CH$_2$CH$_2$—[O—CH$_2$CH$_2$]$_n$—O—CH$_2$—C(=O)—$Z_1$]

L15 [Structure: $A_1$—(CH$_2$)$_n$—O—C(=O)—$Z_1$]

TABLE 5-continued

B1 Structures

L16 [Structure: $A_1$—CH$_2$CH$_2$—[O—CH$_2$CH$_2$]$_n$—O—CH$_2$—O—C(=O)—$Z_1$]

(chemical formula represented between A1 and Z1 where n = 1-12)

In another specific embodiment, $A_1$ represents a heteroaromatic ring bearing an alkylated nitrogen atom (i.e., a pyridinium) where the position of the pyridinium nitrogen may be in the 2, 3 or 4 position with respect to the porphyrin ring. Further, A2, A3 and A4 represent pyridine, or alkylpyridinium, rings where the position of the pyridine, or alkylpyridinium, nitrogen may independently be in the 2, 3 or 4 position with respect to the porphyrin ring. The alkyl portion of the alkylpyridinium moiety represents lower alkyl or branched alkyl. $B_1$ may be selected from the group L9, L10, L15, L16 (Table 5). $Z_1$ may be selected from the cytotoxins of the anthracycline, kinase inhibitor or auristatin type, respectively (Tables 2-4).

In a most preferred embodiment, $A_1$ is a heteroaromatic ring bearing a nitrogen atom (i.e., a pyridinium) where the position of the pyridinium nitrogen is in the 4 position with respect to the porphyrin ring. Moreover, A2, A3 and A4 represent pyridine rings wherein the position of each nitrogen atom is in the 4 position relative to the porphyrin ring. $B_1$ may be selected from the group L9 or L15 (Table 5). $Z_1$ may be selected from the cytotoxins T1b or1, in Tables 2 and 3, respectively.

EXAMPLES

Porphyrins preferentially taken up by cancer cells as compared to non-cancer cells. The mechanism responsible for this is poorly understood. Table 9 is a list of some of the porphyrins and the type of cancer cells that exhibit preferential uptake of the porphyrin as compared to uptake of the porphyrin by non-cancer cells. The list is not exhaustive but illustrative of the effect.

TABLE 9

CANCER CELL LINES

| Porphyrin | Model |
| --- | --- |
| hematoporphyrin | Murine carcinoma |
| L-aspartyl-chlorin e6 | Murine carcinoma |

TABLE 9-continued

CANCER CELL LINES

| Porphyrin | Model |
|---|---|
| Chloraluminum pthalocyanine | Murine carcinoma |
| 5,10,15,20-tetrakis (5-morpholinopentyl)-21H,23H-Porphin (MPP) | Human bladder cancer (T24) cells in murine xenograft |
| Venteporphyrin | Human colorectal cancer cells |
| Protoporphyrin IX | Human squamous cell carcinoma cells |
| Porfimer sodium | Tumor-normal tissue selectivity in human patients |
| Lemuteporfin (a chlorin) | Selective accumulation in mitogen-activated lymphoid cells |
| Metalloporphyrins and conjugates | Human colon and sarcoma cells tumor accumulation. |
| Sulfonylated aryl porphyrins | Human melanoma cells vs. fibroblasts (normal cells) |
| Mn pyridylporphyrins | Selective toxicity against human breast cancer cells vs. normal breast cells. |
| Temoporfin | squamous cell carcinoma of the head and neck |

Figure 2:
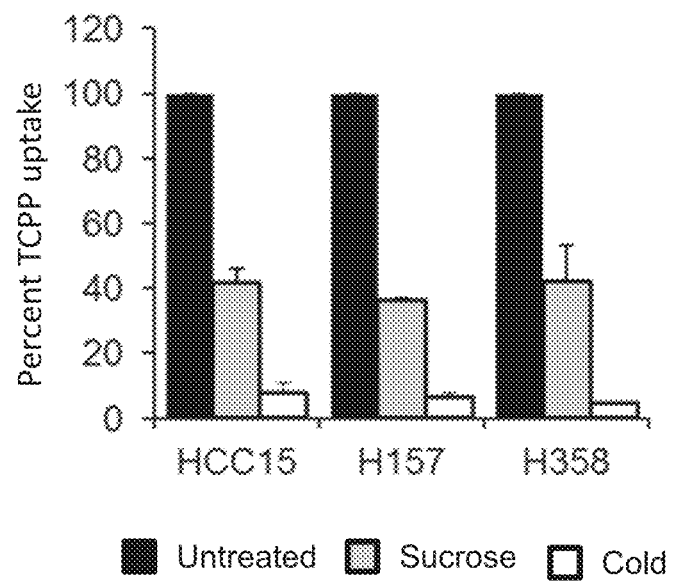
FIG. 2 illustrates inhibition of TCPP uptake in cancer cells under various conditions.
Figure 3:
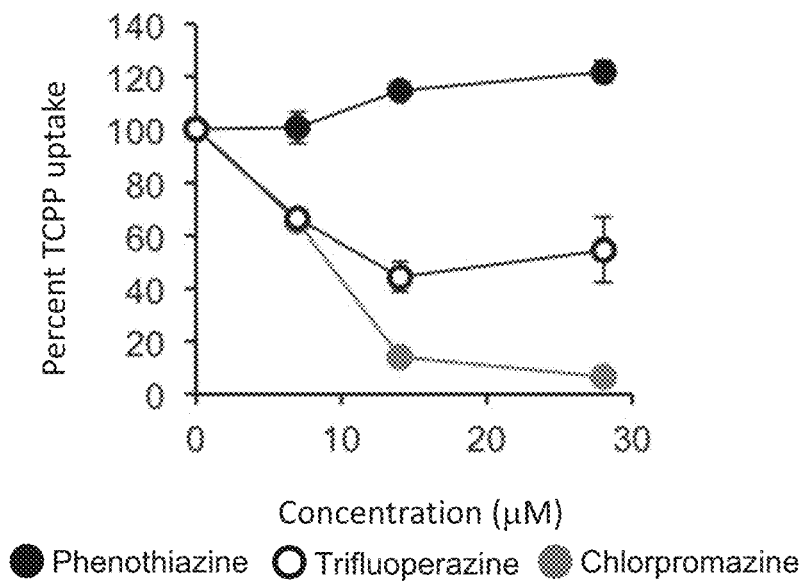
FIG. 3 illustrates a graph of TCPP uptake by a cancer cell treated with different inhibitors of endocytosis.

Porphyrin tetrakis(4-carboxyphenyl)porphyrin (TCPP) uptake by a panel of human lung cancer cell lines including, HCC15, H157, and H358 were examined using flow cytometry in under varying conditions to manipulate clathrin-dependent and independent endocytosis by chemical inhibitors. Referring now to FIG. 1, TCPP uptake in cancer cells (HCC15) as compared to bone marrow cells in a dose dependent manner is illustrated. Similar results are observed with mouse normal lung cells as is shown for bone marrow cells. The uptake of TCPP by HCC15 is greater than 2-fold at 10 ug/ml as compared to the non-cancer cells. As is illustrated in FIG. 2, TCPP uptake in cancer cell lines HCC15, H157 and H358 is moderately inhibited by sucrose and nearly completely inhibited by cold temperature, suggesting that endocytosis is at play in TCPP uptake by the cell. Chlorpromazine, an antagonist of clathrin-mediated endocytosis, inhibited TCPP uptake in a cancer cell line by up to 80% as is illustrated in FIG. 3. In contrast, the clathrin-independent endocytosis inhibitor filipin had no effect on TCPP uptake. It has been speculated that preferential porphyrin uptake by cancer cells as compared to non-cancer cells is facilitated by the increased number of LDL receptor (LDLR) on the surface of cancer cells. To examine LDLR contribution on TCPP uptake, lung cancer cells were manipulated to express no LDLR, which reduced TCPP uptake by only 20%. Surprisingly, TCPP uptake in human fibroblasts without functional LDLR showed no inhibition of TCPP at all. These data suggest that additional receptors (to LDLR) and/or mechanisms (to endocytosis) are involved in TCPP uptake.

Figure 4:
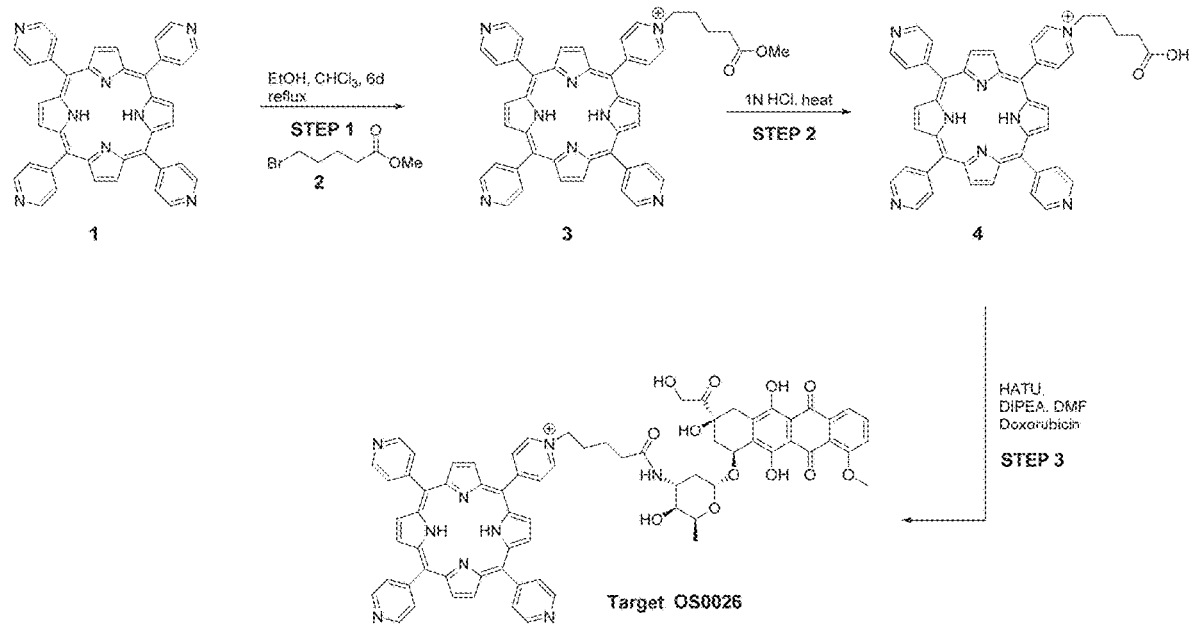
FIG. 4 illustrates a synthesis scheme for compound OS0026.

PAC compounds of Formula III can be synthesized as described below. The procedure for the synthesis of target OS0026 is illustrated in FIG. 4.

STEP 1: Synthesis of 1-(5-methoxy-5-oxopentyl)-4-(10,15,20-tri(pyridin-4-yl)porphyrin-5-yl)pyridin-1-ium bromide (3). A mixture of meso-tetrakis(4-pyridyl)porphyrin (1) (420 mg, 0.67 mmol) and methyl 5-bromopentanoate 2 (1.58 g, 8.08 mmol) in 33 mL EtOH and 100 mL chloroform was stirred at reflux for 6 days. The reaction mixture was purified by two successive column chromatography over silica gel using EtOH/Chloroform (3/7) as eluent to give 3 as a purple solid (186 mg, 30%). $^1$H-NMR (300 MHz, DMSO-$d_6$): δ 11.95 (s, 2H), 9.52-9.55 (d, 2H), 8.94-9.10 (m, 16H), 8.29-8.31 (t, 6H), 4.94 (t, 2H), 3.68 (s, 3H), 2.51-2.58 (m, 2H), 2.66 (m, 2H), 1.84 (m, 2H). MS m/z=733 [M]$^+$. Purity by HPLC: >95%, $t_R$=3.48.

STEP 2: Synthesis of 1-(4-carboxybutyl)-4-(10,15,20-tri(pyridin-4-yl)porphyrin-5-yl)pyridin-1-ium chloride (4). Ester derivative 3 (230 mg, 0.28 mmol) was dissolved in 46 mL 1N HCl to give a green solution, which was stirred at reflux for 3 h. The reaction mixture was lyophilized to afford the corresponding acid derivative 4 as a purple solid (244 mg, chide yield 100%). The crude product was used directly for the next step without further purification. $^1$H-NMR (300 MHz, DMSO-$d_6$): δ 11.90 (s, 2H), 9.50 (d, 2H), 9.35-9.37 (d, 6H), 9.13 (m, 8H), 9.02-9.04 (d, 2H), 8.79 (s, 6H), 5.5 (br, 5H), 5.0 (m, 2H), 2.3 (m, 2H), 1.85 (m, 2H). Purity by HPLC: >95%, $t_R$=3.29.

STEP 3: Synthesis of 1-(5-(((2S,3S,4R,6R)-3-hydroxy-2-methyl-6-(((1S,3S)-3,5,12-trihydroxy-3-(2-hydroxyacetyl)-10-methoxy-6,11-dioxo-1,2,3,4,6,11-hexahydrotetracen-1-yl)oxy)tetrahydro-2H-pyran-4-yl)amino)-5-oxopentyl)-4-(10,15,20-tri(pyridin-4-yl)porphyrin-5-yl)pyridin-1-ium TFA salt (OS0026). To a solution of acid derivative 4 (45 mg, 0.05 mmol) in 4.5 mL DMF was added HATU (45 mg, 0.12 mmol) in one portion, followed by the dropwise addition of DIPEA (45 mg, 0.35 mmol) at room temperature. The reaction mixture was stirred for 5 min at r.t before the addition of doxorubicin hydrochloride (30 mg, 0.056 mmol) in one portion. The reaction mixture was stirred at room temperature overnight and evaporated to remove solvent. The residue was purified by reverse phase preparatoryHPLC using ACN/water with TFA as eluent to afford the desired target compound OS0026 (30 mg, 33%) as a purple solid. Purity by HPLC: >95%, $t_R$=3.48.

HPLC Condition.

Agilent Tech 1100 series HPLC System equipped with Variable Wavelength Detector and ELSD Detector Column: Agela, Durashell C18, 3.0 μm, 4.60×50 mm.

Mobile Phase: A ACN with 0.1% TFA

Mobile Phase: D H$_2$O with 0.1% TFA

Gradient

| Time | A (ACN with 0.1% TFA) | D (H$_2$O with 0.1% TFA) |
|---|---|---|
| 0 | 5 | 95 |
| 5.75 | 95 | 5 |
| 8 | 95 | 5 |
| 9 | 5 | 95 |

Detection: UV at 254 nm & ELSD

Flow rate: 1 mL/min

Injection volume: 5 μL

Column Temp: RT

Run time: 9 min

The synthetic scheme for OS0026 illustrates the alkylation of meso-tetrakis(4-pyridyl)porphyrin (1) with methyl 5-bromopentanoate (2) to yield an intermediate ester (3), which is then hydrolyzed to the corresponding acid (4) and subsequently coupled to the aminosugar nitrogen of doxorubicin using the peptide coupling reagent HATU to afford OS0026.

Further, a pyridyl porphyrin conjugate having the general structure P2

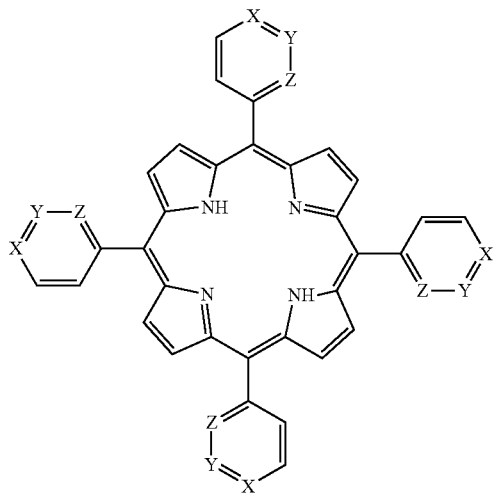

P2 wherein X is nitrogen (N) is illustrated. However, N may alternatively be positioned on each ring at Y or Z instead of X with the linker bound to the N at the alternative position. Thus, on each pyridine ring of P2, N may be independently positioned at either X or Y or Z, with CH groups occupying the remaining two positions. For example, the porphyrin meso-tetrakis(3-pyridyl) porphyrin could be represented as Y is N, X and Z are CH on all four pyridine rings. In a general embodiment, the position of the N atom on each ring may differ. In a more preferred embodiment, the position of the N atom in each pyridine ring is the same in all four pyridine rings. In a preferred embodiment, the porphyrin meso-tetrakis(4-pyridyl) porphyrin could be represented as X=N, and Y and Z are CH on all four pyridine rings.

P2 or an isomer thereof is reacted with an alkylator selected from either L1 or L2. In particular, n is 1-12 for L1 or L2 and X is a leaving group suitable for an $S_N2$ reaction with a pyridine nitrogen to form an alkylpyridinium salt (e.g., 3 in FIG. 4). In this context, the leaving group X is either a halogen leaving groups (Cl, Br, I) or a variety of activated sulfonyl esters such as mesylates, tosylates or triflates. Moreover, Y on L1 or L2 may be a variety of carboxylate esters (OR), wherein R may be chosen to be H, lower straight chain or branched alkyl, cycloalkyl, aryl or heteroaryl. In a preferred embodiment, L1 is selected such that n=3, X is bromo and Y is methoxy.

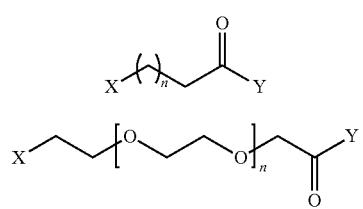

L1

L2

The toxin conjugated in FIG. 4 is doxorubicin, but could more generally be chosen from the anythracycline antibiotics possessing an aminosugar moiety capable of forming an amide bond, as illustrated in Table 6, wherein doxorubicin is illustrated as T1b and examples of analogues therefore are illustrated at T2b-T4b. In a preferred embodiment, P2 is selected such that X=N and Y and Z are both CH. Moreover, X is positioned at the 4-position relative to the porphyrin ring. In this embodiment, L1 is selected such that X is Br and Y is OMe, n=3, and the toxin is T1b.

TABLE 6

Examples of anthracyclines containing an aminosugar

| Tnb | R1 | R2 | * |
|---|---|---|---|
| T1b | OH | OMe | R |
| T2b | H | OMe | R |
| T3b | H | H | R |
| T4b | OH | OMe | S |

Figure 5:
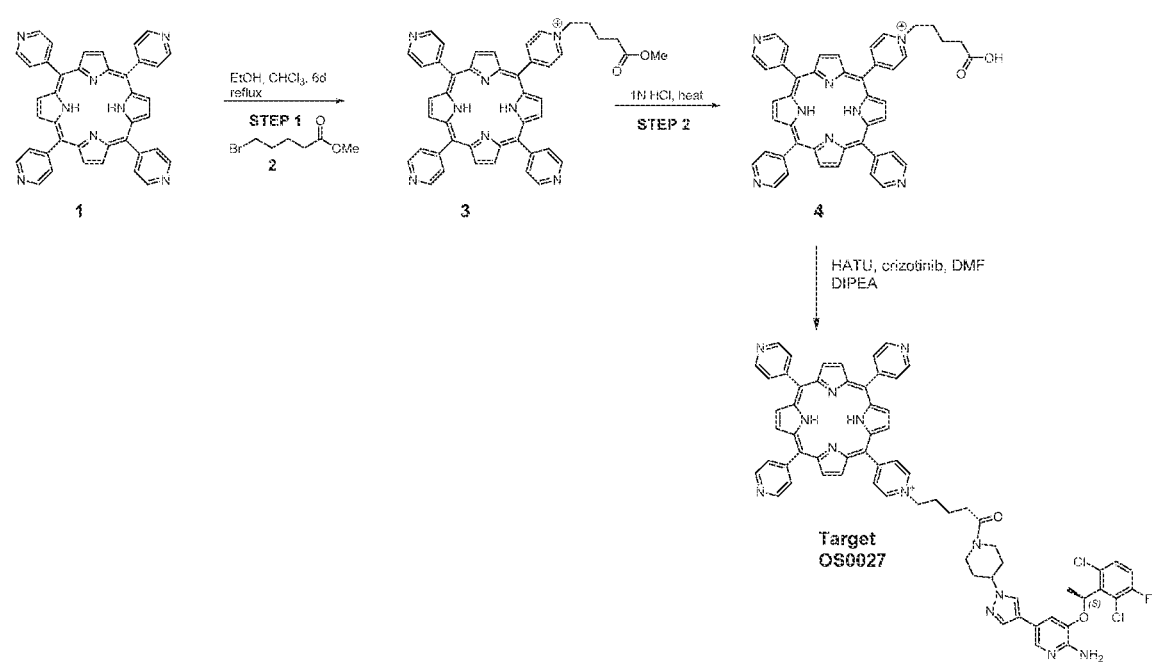
FIG. 5 illustrates a synthesis scheme for compound OS0027.

The procedure for the synthesis of target OS0027 is illustrated in FIG. 5 and described below.

STEP 1: Synthesis of 1-(5-methoxy-5-oxopentyl)-4-(10,15,20-tri(pyridin-4-yl)porphyrin-5-yl)pyridin-1-ium bromide (3). A mixture of meso-tetrakis(4-pyridyl)porphyrin (1) (1) (420 mg, 0.67 mmol) and methyl 5-bromopentanoate 2 (1.58 g, 8.08 mmol) in 33 mL EtOH and 100 mL chloroform was stirred at reflux for 6 days. The reaction mixture was purified by two successive column chromatography over silica gel using EtOH/Chloroform (3/7) as eluent to give 3 as a purple solid (186 mg, 30%). $^1$H-NMR (300 MHz, DMSO-$d_6$): δ 11.95 (s, 2H), 9.52-9.55 (d, 2H), 8.94-9.10 (m, 16H), 8.29-8.31 (t, 6H), 4.94 (t, 2H), 3.68 (s, 3H), 2.51-2.58 (m, 2H), 2.66 (m, 2H), 1.84 (m, 2H). MS m/z=733 [M]$^+$. Purity by HPLC: >95%, $t_R$=3.48.

STEP 2: Synthesis of 1-(4-carboxybutyl)-4-(10,15,20-tri(pyridin-4-yl)porphyrin-5-yl)pyridin-1-ium chloride salt (4). Ester derivative 3 (230 mg, 0.28 mmol) was dissolved in 46 mL 1N HCl to give a green solution, which was stirred at reflux for 3 h. The reaction mixture was lyophilized to afford the corresponding acid derivative 4 as a purple solid (244 mg, crude yield 100%). The crude product was used directly for the next step without further purification. $^1$H-NMR (300 MHz, DMSO-$d_6$): δ 11.90 (s, 2H), 9.50 (d, 2H), 9.35-9.37 (d, 6H), 9.13 (m, 8H), 9.02-9.04 (d, 2H), 8.79 (s, 6H), 5.5 (br, 5H), 5.0 (m, 2H), 2.3 (m, 2H), 1.85 (m, 2H). Purity by HPLC: >95%, $t_R$=3.29.

Synthesis of (5)-1-(5-(4-(4-(6-amino-5-(1-(2,6-dichloro-3-fluorophenyl)ethoxy)pyridin-3-yl)-1H-pyrazol-1-yl)piperidin-1-yl)-5-oxopentyl)-4-(10,15,20-tri(pyridin-4-yl)porphyrin-5-yl)pyridin-1-ium TFA salt (OS0027). To a solution of acid derivative 4 (86 mg, 0.1 mmol) in 8.6 mL DMF was added HATU (52 mg, 0.23 mmol) in one portion, followed by the dropwise addition of DIPEA (86 mg, 0.67 mmol) at room temperature. The resulted mixture was stirred for 5 min at r.t before the addition of crizotinib hydrochloride (52 mg, 0.11 mmol) in one portion. The resulted mixture was stirred at room temperature overnight and evaporated to remove solvent. The residue was purified by reverse phase preparatory HPLC using ACN/Water with TFA as eluent to afford the desired target compound OS0027 as a purple solid (27 mg, 17%). MS (ESI) m/z=1150 [M]$^+$. Purity by HPLC (ELSD): >95%, $t_R$=4.00.

HPLC Condition.
Agilent Tech 1100 series HPLC System equipped with Variable Wavelength Detector and ELSD Detector
Column: Agela, Durashell C18, 3.0 μm, 4.60×50 mm.
Mobile Phase: A ACN with 0.1% TFA
Mobile Phase: D H$_2$O with 0.1% TFA
Gradient

| Time | A (ACN with 0.1% TFA) | D (H$_2$O with 0.1% TFA) |
|---|---|---|
| 0 | 5 | 95 |
| 5.75 | 95 | 5 |
| 8 | 95 | 5 |
| 9 | 5 | 95 |

Detection: UV at 254 nm & ELSD
Flow rate: 1 mL/min
Injection volume: 5
Column Temp: RT
Run time: 9 min The synthetic scheme for OS0027 illustrates the alkylation of meso-tetrakis(4-pyridyl)porphyrin (1) methyl 5-bromopentanoate (2) to yield an intermediate ester (3), which is then hydrolyzed to the corresponding acid (4) and subsequently coupled to the secondary amine of the toxin (crizotinib) using the peptide coupling reagent HATU to afford OS0027.

In one embodiment, a pyridyl porphyrin having the general structure of P2 is used. P2, having a nitrogen atom (N) is positioned at X or Y or Z, with CH occupying the remaining two positions. For example, the porphyrin meso-tetrakis(3-pyridyl)porphyrin could be represented as Y is N, X and Z are CH on all four pyridine rings. In a general embodiment, the position of the N on each ring may differ. In a preferred embodiment, the position of the N on each ring is the same.

In another general embodiment, P2 is reacted with an alkylator selected from either L1 or L2. In L1 or L2, n is 1-12, X is a leaving group suitable for an S$_N$2 reaction with a pyridine nitrogen atom to form an alkylpyridinium species (e.g., 3 in FIG. 5). In this context, the leaving group X is either a halogen leaving groups (Cl, Br, I) or a variety of activated sulfonyl esters such as mesylates, tosylates or triflates. Moreover, Y on L1 or L2 may be a variety of carboxylate esters (OR), wherein R may be chosen to be H, lower straight chain or branched alkyl, cycloalkyl, aryl or heteroaryl. In a preferred embodiment, X is bromo and Y is methoxy.

The specific toxin illustrated in FIG. 5 is kinase inhibitor crizotinib (1, Table 7). In an embodiment, crizotinib is replaced with the kinase inhibitors Tna (n=1-33) in Table 7. In this context, X represents the location of amide bond formation to L1 or L2. In a preferred embodiment, P2 is selected such that X=N and Y and Z are both CH. Moreover, X is positioned at the 4-position relative to the porphyrin ring. In this embodiment, L1 is selected such that X is Br and Y is OMe, n=3, and the cytotoxin is crizotinib (1).

TABLE 7

Kinase inhibitors and analogues.

| Toxin | Structure | Parent toxin name |
|---|---|---|
| 1 | 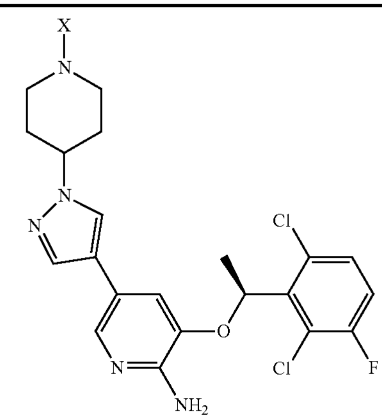 | Crizotinib |
| T1a | 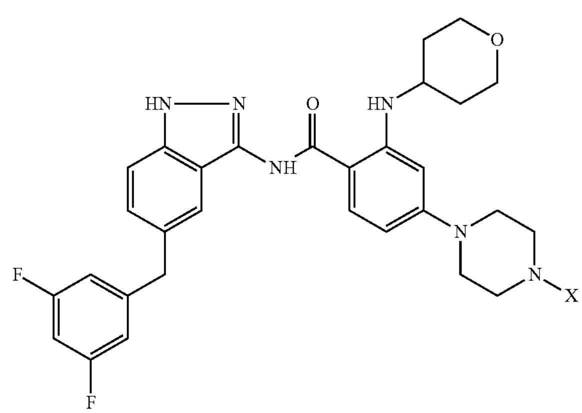 | entrecitinib |

TABLE 7-continued

Kinase inhibitors and analogues.

| Toxin | Structure | Parent toxin name |
|---|---|---|
| T3a | 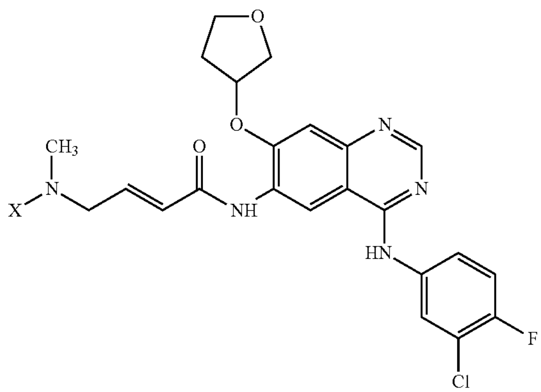 | pelitinib |
| T4a | 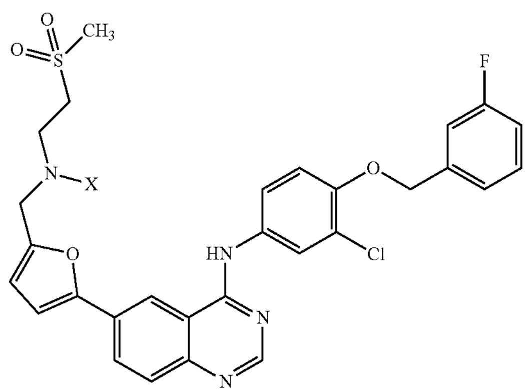 | lapatinib |
| T8a | 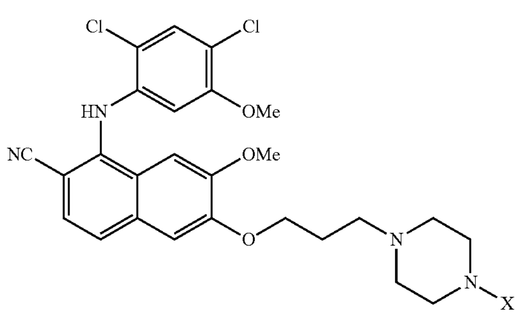 | bosutinib |
| T10a | 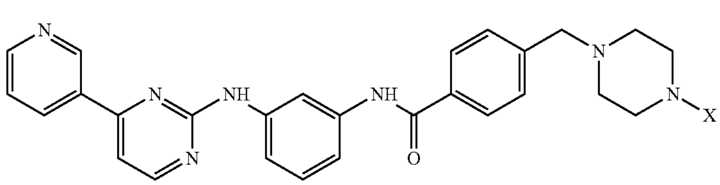 | imatinib |

TABLE 7-continued
Kinase inhibitors and analogues.
| Toxin | Structure | Parent toxin name |
|---|---|---|
| T14a | 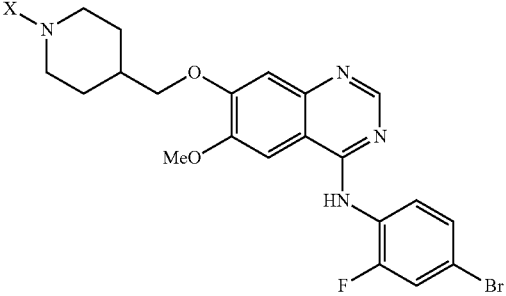 | vandetanib |
| T15a | 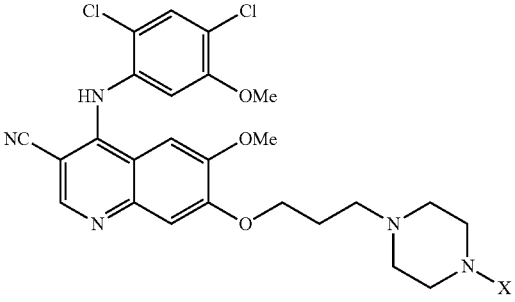 | bosutinib |
| 18a | 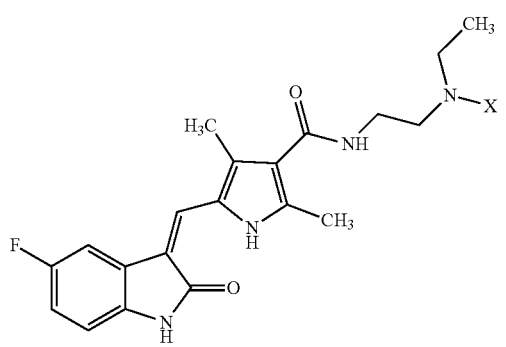 | sunutinib |
| T19a | 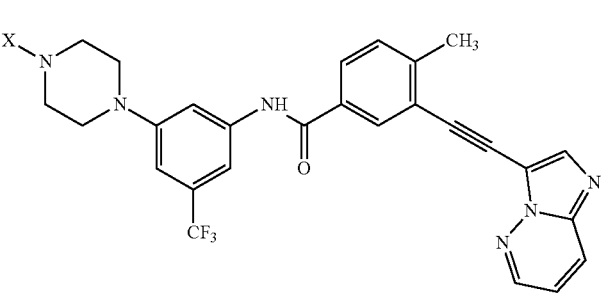 | ponatinib |

TABLE 7-continued

Kinase inhibitors and analogues.

| Toxin | Structure | Parent toxin name |
|---|---|---|
| T21a | 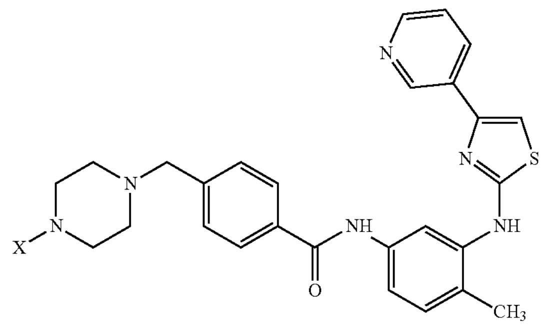 | masitinib |
| T27a | 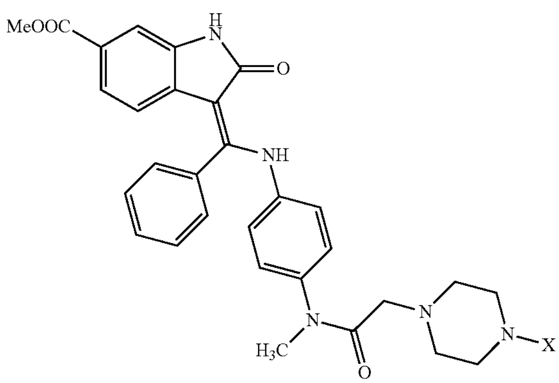 | nintedanib |
| T29a | 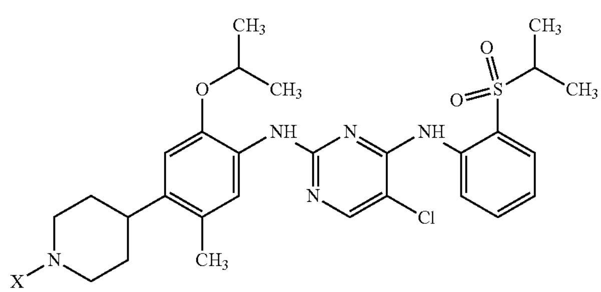 | ceritinib |
| T31a | 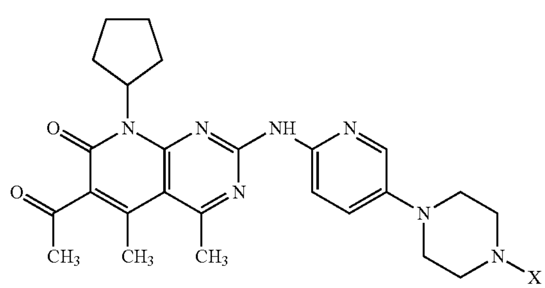 | palbociclib |

TABLE 7-continued

Kinase inhibitors and analogues.

| Toxin | Structure | Parent toxin name |
|---|---|---|
| T32a | 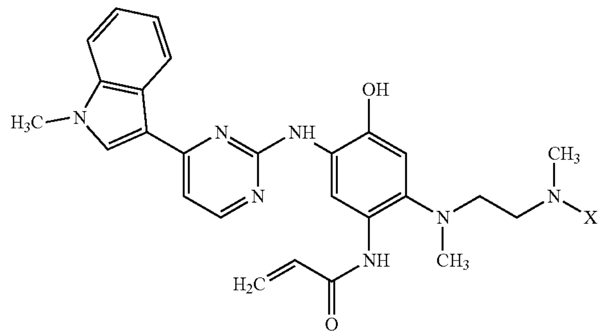  | osimertinib |
| T33a | 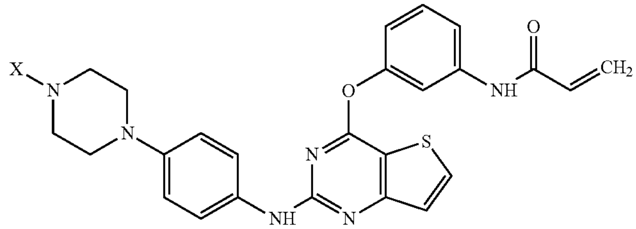  | Olmutinib |

The procedure for the synthesis of target OS002 is illustrated in FIG. 6 and described below.

Preparation of tert-butyl (2-(((4-nitrophenoxy)carboxyl) oxy)ethyl)carbamate (4). To a mixture of tert-butyl (2-hydroxyethyl)carbamate 2 (1.2 g, 7.45 mmol) and triethylamine (2.58 mL, 18.6 mmol) in $CH_2Cl_2$ (80 mL) was added p-nitrophenyl chloroformate 3 (1.5 g, 7.45 mmol) portion wise at 0° C. The resultant mixture was warmed to room temperature and stirred for 5 h. The mixture was quenched with 10 mL saturate $NH_4Cl$ solution, extracted with $CH_2Cl_2$ (2×50 mL). The combined organic layers were washed with brine (20 mL), dried over $Na_2SO_4$, and evaporated. The crude residue was purified by normal phase chromatography with 0-100% EtOAc-hexanes to give 4 (1.92 g, 79%). $^1$H-NMR (300 MHz, $CDCl_3$): δ 8.28 (d, 2H), 7.39 (d, 2H), 4.85-4.95 (m, 1H), 4.33 (t, 2H), 3.0-3.51 (m, 2H), 1.45 (s, 9H).

Preparation of 2-((tert-butoxycarboxyl)amino)ethyl (S)-4-(4-(6-amino-5-(1-(2,6-dichloro-3-fluorophenyl)ethoxy) pyridin-3-yl)-1H-pyrazol-1-yl)piperidine-1-carboxylate (5). To a mixture of crizotinib hydrochloride 1 (100 mg, 0.2 mmol) and 4 (136 mg, 0.41 mmol) in $CH_2Cl_2$ (50 mL) was added DIPEA (0.4 mL g, 0.67 mmol) at room temperature. The resultant mixture was stirred for 16 h. The mixture was washed with water (2×20 mL). The organic layer was washed with brine (20 mL), dried over $Na_2SO_4$, and evaporated. The crude residue was purified by normal phase chromatography with 0-10% MeOH—$CH_2Cl_2$ to give 5 (130 mg, 99%). $^1$H-NMR (300 MHz, $CDCl_3$): δ 7.75 (d, 1H), 7.55 (s, 1H), 7.47 (s, 1H), 7.25-7.27 (m, 1H), 7.01-7.08 (m, 1H), 6.85 (d, 1H), 6.05-6.1 (m, 1H), 475-4.85 (m, 3H), 4.1-4.35 (m, 5H), 3.39-3.45 (m, 2H), 2.9-3.0 (m, 2H), 2.1-2.19 (m, 2H), 1.9-1.98 (m, 2H), 1.86 (d, 3H), 12.1-2.19 (m, 2H), 1.9-1.98 (m, 2H), 1.86 (d, 3H), 1.43 (s, 9H). MS m/z=637.2 $[M]^+$. $t_R$=5.16

Preparation of 2-aminoethyl (S)-4-(4-(6-amino-5-(1-(2,6-dichloro-3-fluorophenyl)ethoxy) pyridin-3-yl)-1H-pyrazol-1-yl)piperidine-1-carboxylate. HCl (6). To a mixture of 5 (125 mg, 0.19 mmol) in THF (10 mL) was added HCl (4 mL, 4N in dioxane) at room temperature. The resultant mixture was stirred for 16 h. The solvents were evaporated and the resultant residue was triturated with diethyl ether. The solid was filtered, and dried to give 6 (100 mg, 94%). This was used in next step without further purification. $^1$H-NMR (300 MHz, DMSO-$d_6$): δ 8.03-8.13 (m, 3H), 7.71-7.85 (m, 3H), 7.53-7.63 (m, 2H), 7.42-7.52 (m, 1H), 7.12 (s, 1H), 6.21-6.31 (m, 1H), 4.25-4.45 (m, 1H), 4.05-4.19 (m, 4H), 2.9-3.07 (m, 4H), 1.91-2.05 (m, 2H), 1.80-1.89 (m, 5H). MS m/z=537.2 $[M]^+$. HPLC Purity=98%, $t_R$=4.72.

Preparation of 4-(10,15,20-tris(4-(methoxycarboxyl)phenyl)porphyrin-5-yl)benzoic acid (8). A mixture of tetramethyl porphyrin derivative 7 (1.0 g, 1.18 mmol) and $Me_3SnOH$ (0.43 g, 2.36 mmol) in 1,2-dichloroethane (10 mL) was reacted in a microwave reactor at 150° C. for 1 h. The solvents were evaporated and the residue absorbed in silica for purification. The silica absorbed crude compound was purified by normal phase chromatography with 0-10% MeOH—$CH_2Cl_2$ (0.1% $CH_3COOH$) to get the desired compound 8 (275 mg, 28%). $^1$H-NMR (300 MHz, DMSO-$d_6$): δ 17.0 (s, 1H), 13.2 (brs, 1H), 8.81-8.82 (m, 8H), 8.35-8.37 (m, 16H), 4.03 (s, 9H).

Preparation of trimethyl 4,4',4"-(20-(4-((2-(((4-(4-(6-amino-5-(1-(2,6-dichloro-3-fluorophenyl)ethoxy)pyridin-3-yl)-1H-pyrazol-1-yl)piperidine-1-carboxyl)oxy)ethyl) carbamoyl) phenyl)porphyrin-5,10,15-triyl)(S)-tribenzoate (TARGET OS002). To a mixture of 6 (100 mg, 0.165 mmol), 8 (143 mg, 0.165 mmol) and PyBOP (136 mg, 0.248 mmol) in NMP (10 mL) was added DIPEA (0.2 mL, 0.99 mmol). The resultant mixture was stirred at ambient temperature overnight. The mixture was quenched with water (2 mL), extracted with $CH_2Cl_2$ (2×20 mL). The combined organic layers were washed with water, dried over $Na_2SO_4$, and evaporated. The crude compound was purified by normal phase chromatography with 0-10% MeOH—$CH_2Cl_2$ to get the desired target compound OS002 (132 mg, 56%) as purple solid. $^1$H-NMR (300 MHz, CDCl$_3$): δ 12.17 (s, 1H), 8.81 (d, 8H), 8.45 (d, 6H), 8.18-8.29 (m, 10H), 7.72 (s, 1H), 7.43-7.53 (m, 3H), 7.14-7.18 (m, 1H), 6.93 (t, 1H), 6.79 (s, 1H), 5.9-6.1 (m, 1H), 4.72 (s, 2H), 4.53 (t, 1H), 4.2-4.48 (m, 3H), 4.10 (s, 9H), 3.89-3.95 (m, 2H), 2.9-3.15 (m, 2H), 2.13-2.23 (m, 2H), 1.9-2.19 (m, 2H), 1.77 (d, 3H), Purity by HPLC: >96%, $t_R$=7.69.

HPLC Condition.

Agilent Tech 1200 series HPLC System equipped with Variable Wavelength Detector and Mass Spectrometer.
Column: Agela, Durashell C18, 3.0 μm, 4.60×50 mm.
Mobile Phase: A (ACN with 0.1% TFA)
Mobile Phase: D (H$_2$O with 0.1% TFA)
Gradient

| Time | A (ACN with 0.1% TFA) | D (H$_2$O with 0.1% TFA) |
|---|---|---|
| 0 | 5 | 95 |
| 5.75 | 95 | 5 |
| 8 | 95 | 5 |
| 9 | 5 | 95 |

Detection: UV at 254 nm

In the synthetic scheme for OS002, the condensation of aryl carboxylate 8 with the primary amine 6 using the amidation reagent PyBOP to afford OS002 is illustrated. In an embodiment, aryl carboxylate 8 may be exchanged for carboxylate P1, where the carboxylic acid substituent (COOH) occupies ortho, meta or para, that is, positions 2, 3 or 4, and wherein the three substituents L, M and N may independently occupy the ortho, meta or para (positions 2, 3 or 4) on their respective aromatic rings.

P1

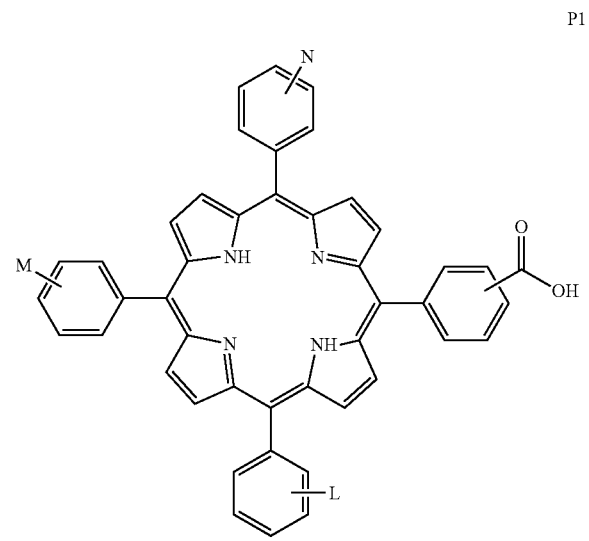

The substituents L, M and N are selected from the group consisting of:
a) H;
b) carboxyaryl esters and acids (COOR) wherein the R may be H, lower straight chain or branched alkyl, cycloalkyl, hydroxy-substituted alkyl, polyethers (lower PEG), amino-substituted alkyl, hetero-substituted cycloalkyl and additionally, sugars. In addition, R may include aryl and heteroaryl substituents;

c) Carboxamides (CONR1R2), wherein the R1 and R2 groups may individually be selected from H, be lower straight chain or branched alkyl, cycloalkyl, hydroxy-substituted alkyl, polyethers (lower PEG), amino-substituted alkyl, hetero-substituted cycloalkyl. In addition, R may include aryl and heteroaryl substituents;

d) Aminoaryl groups (NR1R2) wherein R1 or R2 may individually be selected from the group lower alkyl, branched lower alkyl, cycloalkyl, or hetero-substituted alkyl or hetero-substituted cycloalkyl. R may also be an acyl group such as C(O)R, where R may include lower alkyl, hydroxy-substituted alkyl, polyethers (lower PEG), amino-substituted alkyl, cycloalkyl. In addition, R may include aryl and heteroaryl substituents;

e) Sulfur containing functional groups that may include thiols, sulfonic acids and corresponding amides thereof. The amides may be further defined as containing a nitrogen moiety NHR, with the N connected by a single bond to the sulfur atom, and where R is lower alkyl, cycloalkyl, or hetero-substituted alkyl or hetero-substituted cycloalkyl. R may also be an acyl group such as C(O)R, where R may include lower alkyl, hydroxy-substituted alkyl, polyethers (lower PEG), amino-substituted alkyl, cycloalkyl. In addition, R may include aryl and heteroaryl substituents;

f) Lower straight chain or branched alkyl groups, cycloalkyl groups, hydroxy-substituted alkyl, polyethers (lower PEG), amino-substituted alkyl, cycloalkyl and hetero-substituted cycloalkyl; and g) Oxygen groups such as hydroxy and substituted hydroxyaryl (OH or OR), where R may be chosen from the group including lower straight chain or branched alkyl groups, cycloalkyl groups, hydroxy-substituted alkyl, polyethers (lower PEG), amino-substituted alkyl, cycloalkyl and hetero-substituted cycloalkyl. In addition, R may include acyl (C(O)R), carbamoyloxy (C(O)NR1R2), wherein R1 and R2 are lower alkyl, aryl and heteroaryl substituents.

In a further embodiment, the carboxylate substituent (COOH) occupies the para (4-position) on its aromatic ring and further, the substituents on each of the other three aromatic rings are identical, that is L=M=N. Moreover, the substituents L, M and N are situated such that their positions on each aromatic ring are identical; for example, where each substituent occupies the meta position on its respective aromatic ring. A preferred embodiment is where the substituents L, M and N are all carboxylate (COOH) or carboxymethyl (COOMe) and are situated at the para position (i.e., 4-position) of their respective aromatic rings.

Figure 6:
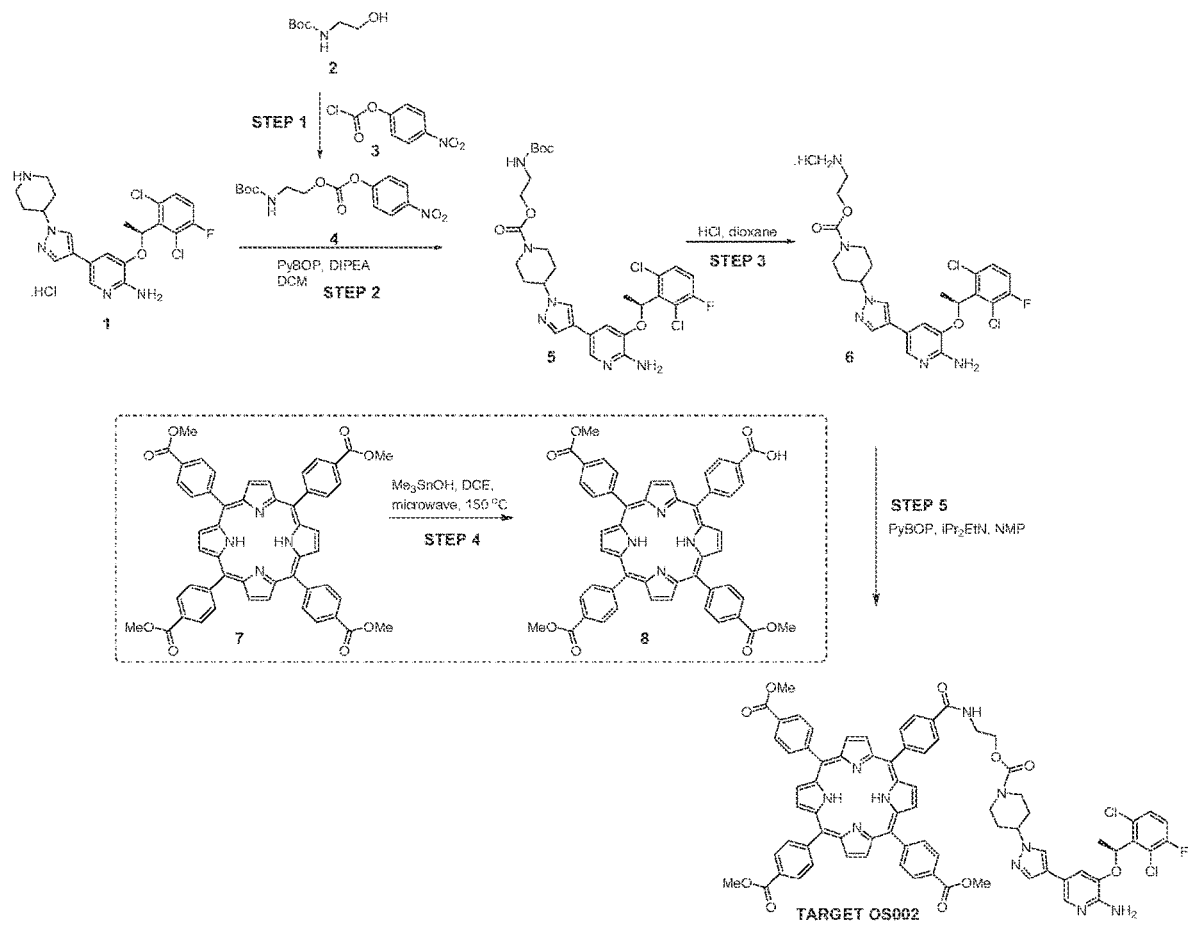
FIG. 6 illustrates a synthesis scheme for compound OS002.

As shown in FIG. 6, the starting material tent-butyl (2-hydroxyethyl)carbamate (2) is utilized as a key building block for the linker moiety that connects the porphyrin 8 to crizotinib by way of a carbamate bond to the nitrogen of cizotinib and an amide bond to the carboxylate of 8. In one embodiment, the starting material 2 is replaced by a protected aminoalcohol L5 or L6, wherein the group P represents an amine protecting group that may include carbamates (e.g., BOC, FMOC, Alloc, CBZ), amides (e.g., acetamide, dichloroacetamide) or other protecting groups containing a bond between the nitrogen of the amine and either carbon or silicon of the protecting group (e.g., benzyl, tert-butyl, triisopropylsilyl). In L5 or L6, n=1-12. In a preferred embodiment, the aminoalcohol L5 is chosen such that P is BOC and n=1.

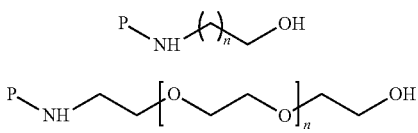

FIG. 6 illustrates the preparation of key intermediate 6, wherein crizotinib is functionalized at its secondary amine by a carbamoyl amine moiety. In an embodiment, the toxin, kinase inhibitor crizotinib, of (1) is replaced with a kinase inhibitor chosen from the set Tna (Table 7). X represents the amide bond to L5 or L6. In a preferred embodiment, P1 is the porphyrin where L, M and N are all carboxylic acid or carboxymethyl groups positioned para to the porphyrin rings, and where the carboxylic acid group forming the amide bond to the linker, is positioned para relative to the porphyrin ring. Moreover, L5 is used, where P=H and n=1 and the kinase inhibitor is criziotinib.

Figure 15:
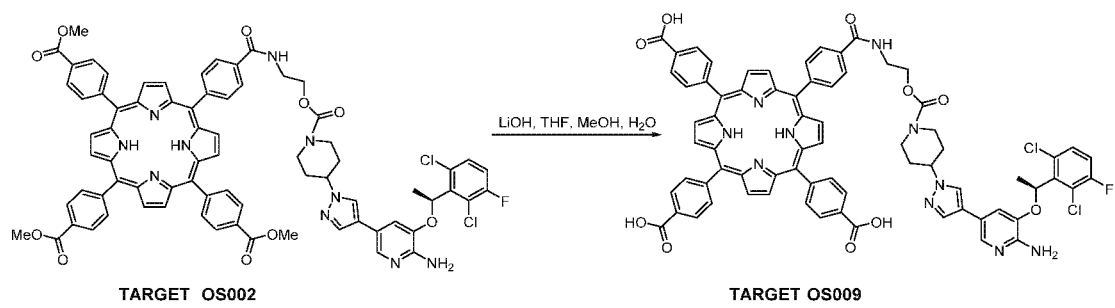
FIG. 15 illustrates a synthesis scheme for compound OS009.

The procedure for the synthesis of target OS009 is illustrated in FIG. 15 and described below.

Preparation of (S)-4,4',4"-(20-(4-((2-((4-(4-(6-amino-5-(1-(2,6-dichloro-3-fluorophenyl) ethoxy)pyridin-3-yl)-1H-pyrazol-1-yl)piperidine-1-carbonyl)oxy)ethyl)carbamoyl) phenyl) porphyrin-5,10,15-triyl)tribenzoic acid (2). To a mixture of OS002 (35 mg, 2.03 mmol) in THF:MeOH:H$_2$O (1.5 mL, 3:1:1) was added LiOH. H$_2$O (7 mg, 0.166 mmol). The resultant mixture was stirred for 64 h at room temperature. The solvents were evaporated and the pH of the reaction mixture was adjusted to pH 6-7, by addition of 0.1 M aqueous HCl solution, and lyophilized. An additional batch was similarly prepared on 25 mg scale following this procedure. The combined batches were purified by preparative HPLC using acetonitrile-water (0.1% TFA) as solvent system to give the desired compound 2 (17.5 mg, 30%) as green solid. MS (ESI) m/z=1309.3 [M]$^+$. Purity by HPLC (ELSD): >97%, t$_R$=6.0.

HPLC Condition.
Agilent Tech 1100 series HPLC System equipped with Variable Wavelength Detector and ELSD Detector
Column: Agela, Durashell C18, 3.0 μm, 4.60×50 mm.
Mobile Phase: A (ACN with 0.1% TFA)
Mobile Phase: D (H$_2$O with 0.1% TFA)

Figure 7:
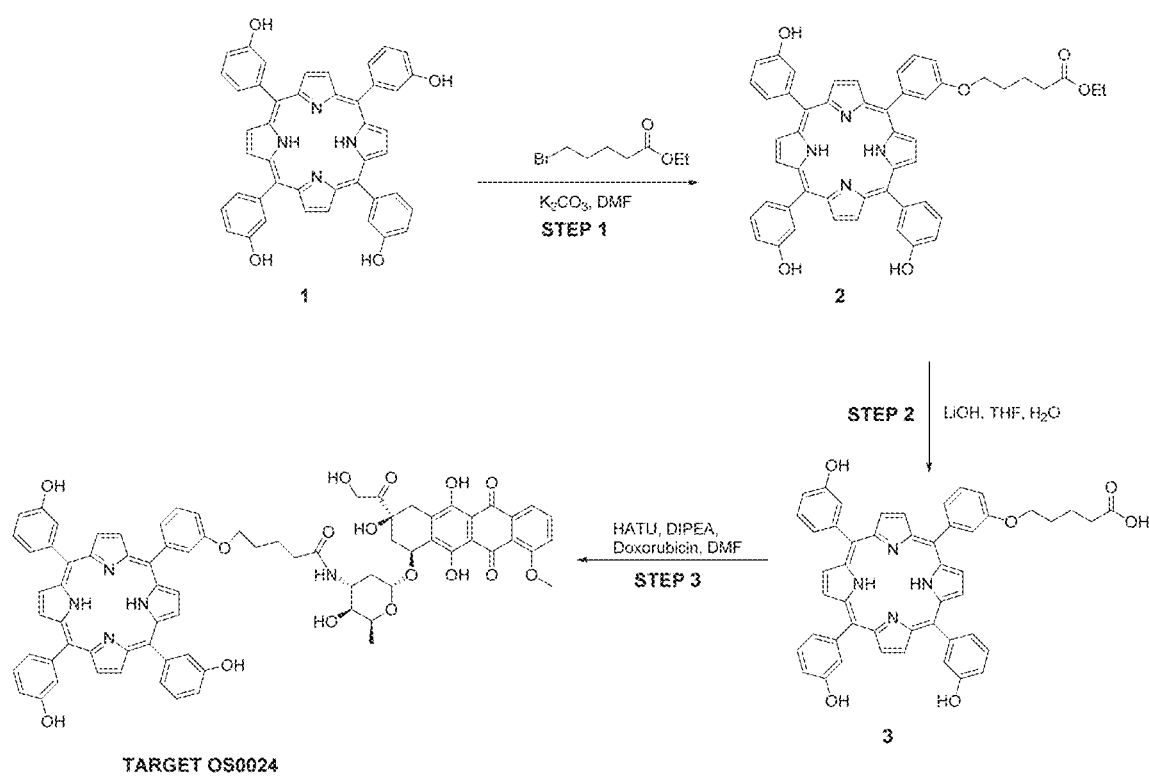
FIG. 7 illustrates a synthesis scheme for compound OS0024.

The procedure for the synthesis of target OS0024 is illustrated in FIG. 7 and described below.

STEP 1: Synthesis of ethyl 5-(3-(10,15,20-tris(3-hydroxyphenyl)porphyrin-5-yl)phenoxy) pentanoate) (2). A mixture of meso-tetrakis(3-hydroxyphenyl)porphyrin 1 (1.25 g, 1.84 mmol) and K$_2$CO$_3$ (0.5 g) in DMF (30 mL) was stirred under nitrogen at room temperature for 30 min. Ethyl 5-bromopentanoate (1.15 g, 5.5 mmol, 3 eq.) was added. The mixture was stirred at room temperature overnight. The reaction mixture was diluted with DCM, washed with water, satd .NaHCO$_3$(aq), water and brine, dried over Na$_2$SO$_4$, and evaporated. The crude residue was purified with two successive column chromatographies to give 2 (0.42 g, 28%).

$^1$H-NMR (300 MHz, DMSO-d$_6$): δ 12.0 (s, 1H), 9.90 (s, 3H), 8.88 (s, 8H), 7.66-7.79 (m, 3H), 7.52-7.65 (m, 9H), 7.36-7.7.42 (m, 1H), 7.18-7.26 (m, 3H), 4.12-4.20 (m, 2H), 4.05 (q, 2H), 2.34-2.40 (m, 2H), 1.65-1.85 (m, 4H), 1.12 (t, 3H).

STEP 2: Synthesis of 5-(3-(10,15,20-tris(3-hydroxyphenyl)porphyrin-5-yl)phenoxy) pentanoic acid (3). To a solution of 2 (157 mg, 0.19 mmol) in THF (45 mL) was added a solution of LiOH—H$_2$O (0.15 g) in water (30 mL) at room temperature. The mixture was stirred at room temperature overnight. Evaporated THF, diluted with sat. NH$_4$Cl, extracted with DCM, washed with brine, and evaporated. It was used for next step reaction without further purification. 3 (0.14 g, 92%); 1H-NMR (300 MHz, DMSO-d6): δ 12.0 (s, 2H), 9.90 (s, 3H), 8.89 (s, 8H), 7.66-7.82 (m, 3H), 7.54-7.65 (m, 9H), 7.36-7.7.42 (m, 1H), 7.20-7.26 (m, 3H), 4.14-4.22 (m, 2H), 2.26-2.36 (m, 2H), 1.65-1.85 (m, 4H).

STEP 3: Synthesis N-((2S,3S,4R,6R)-3-hydroxy-2-methyl-6-0(1S,3S)-3,5,12-trihydroxy-3-(2-hydroxyacetyl)-10-methoxy-6,11-dioxo-1,2,3,4,6,11-hexahydrotetracen-1-yl)oxy) tetrahydro-2H-pyran-4-yl)-5-(3-(10,15,20-tris(3-hydroxyphenyl)porphyrin-5-yl)phenoxy) pentanamide (OS0024). To a solution of 3 (53 mg, 0.068 mmol) in DMF (5.5 mL) was added HATU (56 mg, 0.147 mmol, 2.16 eq.) and DIPEA (75 mL). Stirred at room temperature for 5 min. followed by addition of doxorubicin-HCl (35 mg, 0.06 mmol, 0.9 eq.). The mixture was stirred at room temperature overnight. DMF was evaporated and the residue was purified by a normal phase column chromatography followed by a preparatory-HPLC using ACN/Water with TFA as eluent to afford the desired target compound OS0024 (5 mg). MS(ES) [M+1]+=1304; HPLC purity: 90% (UV400) and ELSD (96%).

HPLC Condition

Agilent Tech 1200 series HPLC System equipped with Variable Wavelength Detector and Mass Spectrometer and ELSD Detector Column: Agela, Durashell C18, 3.0 μm, 4.60×50 mm.

Mobile Phase: A (ACN with 0.1% TFA)

Mobile Phase: D (H$_2$O with 0.1% TFA)

Gradient

| Time | A (ACN with 0.1% TFA) | D (H$_2$O with 0.1% TFA) |
|---|---|---|
| 0 | 5 | 95 |
| 5.75 | 95 | 5 |
| 8 | 95 | 5 |
| 9 | 5 | 95 |

Detection: UV at 400 nm and evaporative light scattering detector.

FIG. 7 illustrates the conjugation of porphyrin 1 with doxorubicin via a covalent linker whose carbons derive from the bifunctional linker starting material ethyl 5-bromopentanoate. In an embodiment, porphyrin 1 could be substituted by porphyrin P4,

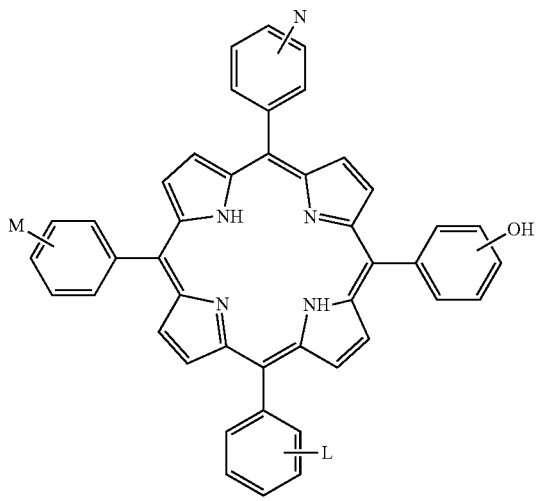

wherein the hydroxy substituent could be situated at the ortho, meta or para positions (positions 2, 3 or 4) of the aromatic ring and, moreover, where the substituents L, M and N, may be independently occupy the ortho, meta or para, that is 2-, 3- or 4-positions, on their respective aromatic rings. The substituents L, M ad N are selected from the set consisting of:
  a) H;
  b) carboxyaryl esters and acids (COOR) where the R may be H, lower straight chain or branched alkyl, cycloalkyl, hydroxy-substituted alkyl, polyethers (lower PEG), amino-substituted alkyl, hetero-substituted cycloalkyl and additionally, sugars. In addition, R may include aryl and heteroaryl substituents;
  c) Carboxamides (CONR1R2), where wherein the R1 and R2 groups may individually be H, be lower straight chain or branched alkyl, cycloalkyl, hydroxy-substituted alkyl, polyethers (lower PEG), amino-substituted alkyl, hetero-substituted cycloalkyl. In addition, R may include acyl (C(O)R1), carbamoyloxy (C(O)NR1R2), aryl and heteroaryl substituents;
  d) Aminoaryl groups (NR1R2) where R1 or R2 may individually be selected from the group lower alkyl, branched lower alkyl, cycloalkyl, or hetero-substituted alkyl or hetero-substituted cycloalkyl. R may also be an acyl group such as C(O)R, where R may include lower alkyl, hydroxy-substituted alkyl, polyethers (lower PEG), amino-substituted alkyl, cycloalkyl. In addition, R may include aryl and heteroaryl substituents;
  e) Sulfur containing functional groups that may include thiols, sulfonic acids and corresponding amides thereof. The amides may be further defined as containing a nitrogen moiety NHR, with the N connected by a single bond to the sulfur atom, and where R is lower alkyl, cycloalkyl, or hetero-substituted alkyl or hetero-substituted cycloalkyl. R may also be an acyl group such as C(O)R, where R may include lower alkyl, hydroxy-substituted alkyl, polyethers (lower PEG), amino-substituted alkyl, cycloalkyl. In addition, R may include aryl and heteroaryl substituents;
  f) Lower straight chain or branched alkyl groups, cycloalkyl groups, hydroxy-substituted alkyl, polyethers (lower PEG), amino-substituted alkyl, cycloalkyl and hetero-substituted cycloalkyl;
  g) Oxygen groups such as hydroxy and substituted hydroxyaryl (OH or OR), where R may be chosen from the group including lower straight chain or branched alkyl groups, cycloalkyl groups, hydroxy-substituted alkyl, polyethers (lower PEG), amino-substituted alkyl, cycloalkyl and hetero-substituted cycloalkyl. In addition, R may include acyl, aryl and heteroaryl substituents; and
  h) Cyano or halogens (F, Cl, Br, I).

In a further embodiment, the aromatic hydroxy substituent (OH) occupies the meta (3 position) on its aromatic ring and, further, the substituents on each of the other three aromatic rings are identical, that is L=M=N. Moreover, the substituents L, M and N are situated such that their positions on each aromatic ring are identical; for example, where each substituent occupies the meta position on its respective aromatic ring. In a preferred embodiment, the substituents L, M and N are all hydroxyl (OH) and are situated at the meta (3 position) of their respective aromatic rings.

As shown in FIG. 7, the phenol group of the porphyrin is alkylated via an $S_N2$ reaction under basic conditions with ethyl 5-bromopentanoate to give intermediate 2. In an embodiment, ethyl 5-bromopentanoate may be replaced by L1 or L2. In particular, n is selected from 1-12 for L1 and L2. X is a leaving group suitable for an $S_N2$ reaction with a phenolic oxygen atom to form a phenolic ether (e.g., 2 in FIG. 7). In this context, the leaving group X is either a halogen leaving groups (Cl, Br, I) or a variety of activated sulfonyl esters such as mesylates, tosylates or triflates. Moreover, Y on L1 or L2 may be a variety of carboxylate esters (OR), wherein R may be chosen to be H, lower straight chain or branched alkyl, cycloalkyl, aryl or heteroaryl. In a preferred embodiment, X is bromo and Y is ethoxy.

Attachment to the doxorubicin occurs via the saponification of the ester group of intermediate 2 to the corresponding carboxylic acid (3) and amide bond formation between the carboxylic acid and the amine on the aminosugar moiety of doxorubicin using the peptide coupling reagent HATU, to afford OS0024. The toxin conjugated in FIG. 7 is doxorubicin, but could more generally be chosen from the anythracycline antibiotics possessing an aminosugar moiety capable of forming an amide bond as illustrated in Table 6, wherein doxorubicin is denoted as T1b and examples of analogues are illustrated as T2b-T4b. In a preferred embodiment, P4 is selected such that all the substituents (L=M=N) are hydroxyl groups positioned meta to the porphyrin ring and wherein L1 is selected such that n=3, X is bromo and Y is ethoxy. Moreover, in this preferred embodiment, the toxin is selected as doxorubicin (T1b).

Figure 8:
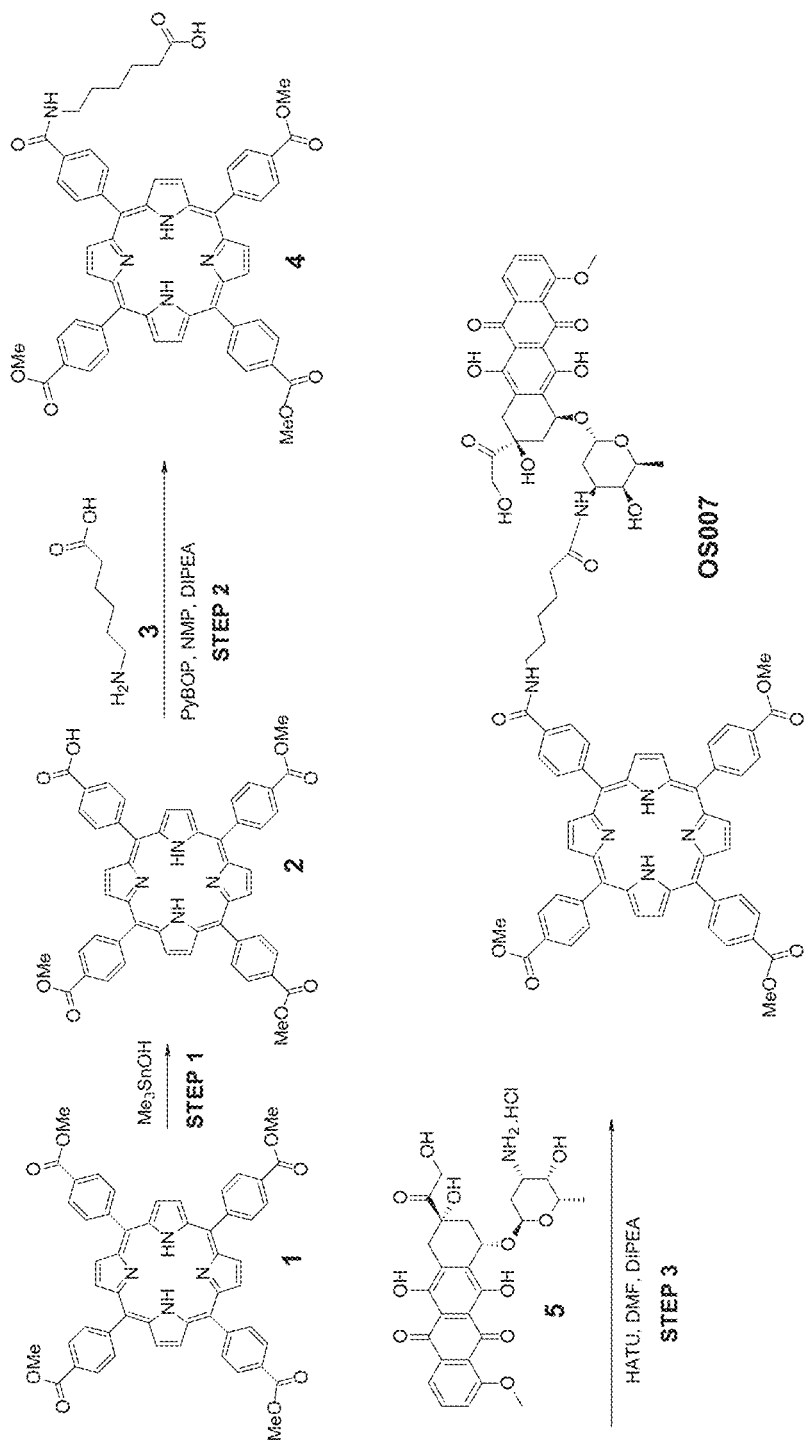
FIG. 8 illustrates a synthesis scheme for compound OS007.

The procedure for synthesis of target OS007 is illustrated in FIG. 8 and described below.

Preparation of 4-(10,15,20-tris(4-(methoxycarbonyl)phenyl)porphyrin-5-yl)benzoic acid (2). A mixture of tetrakis (4-carbomethoxyphenyl)porphyrin (1) (1.0 g, 1.18 mmol) and $Me_3SnOH$ (0.43 g, 2.36 mmol) in 1,2-dichloroethane (10 mL) was reacted in a microwave reactor at 150° C. for 1 h. The solvents were evaporated and absorbed on silica gel for purification. The silica absorbed crude compound was purified by normal phase chromatography with 0-10% MeOH—$CH_2Cl_2$ (0.1% $CH_3COOH$) to get the desired compound 2 (275 mg, 28%). $^1$H-NMR (300 MHz, DMSO-$d_6$): δ 17.0 (s, 1H), 13.2 (brs, 1H), 8.81-8.82 (m, 8H), 8.35-8.37 (m, 16H), 4.03 (s, 9H).

Preparation of 6-(4-(10,15,20-tris(4-(methoxycarbonyl) phenyl)porphyrin-5-yl)benzamido) hexanoic acid (4). A mixture of 2 (300 mg, 0.36 mmol), PyBOP (374 mg, 0.72 mmol) and DIPEA (0.48 mL, 2.8 mmol) in NMP (15 mL) was stirred for 10 min at room temperature. To the above mixture was added 6-aminohexanoic acid (3, 188 mg, 1.44 mmol) and the resultant mixture was stirred at room temperature for 48 h. The mixture was diluted with $CH_2Cl_2$, washed with water (3×50 mL). The organic layer was dried over $Na_2SO_4$, and evaporated. The residue was purified by normal phase chromatography with 0-10% MeOH—$CH_2Cl_2$ to get the desired compound 4 (89 mg, 26%). $^1$H-NMR (300 MHz, $CDCl_3$): δ 12.17 (s, 1H), 8.80 (s, 8H), 8.14-8.44 (m, 16H), 6.39 (brt, 1H), 3.51-3.62 (m, 2H), 2.40-2.45 (m, 2H), 1.45-1.79 (m, 6H).

Preparation of trimethyl 4,4',4"-(20-(4-((6-(((2S,3S,4S,6R)-3-hydroxy-2-methyl-6-(((1S,3S)-3,5,12-trihydroxy-3-(2-hydroxyacetyl)-10-methoxy-6,11-dioxo-1,2,3,4,6,11-hexahydrotetracen-1-yl)oxy)tetrahydro-2H-pyran-4-yl)amino)-6-oxohexyl)carbamoyl)phenyl)porphyrin-5,10,15-triyl)tribenzoate (OS007). To a mixture of 4 (20 mg, 0.021 mmol), HATU (19.2 mg, 0.051 mmol) and DIPEA (30 µL, 0.168 mmol) in DMF (2.5 mL) was stirred for 10 min at room temperature. To the above mixture was added doxorubicin.HCl (5, 13.5 mg, 0.023 mmol) and the resultant mixture was stirred at room temperature for 16 h. The mixture was diluted with $CH_2Cl_2$, washed with water (3×10 mL). The organic layer was dried over $Na_2SO_4$, and evaporated. The residue was purified by normal phase chromatography with 0-10% MeOH—$CH_2Cl_2$ to afford the desired compound OS007 (21 mg, 68%). %). $^1$H-NMR (300 MHz, DMSO-$d_6$): δ 12.0 (s, 1H), 9.90 (s, 3H), 8.88 (s, 8H), 7.66-7.79 (m, 3H), 7.52-7.65 (m, 9H), 7.36-7.7.42 (m, 1H), 7.18-7.26 (m, 3H), 4.12-4.20 (m, 2H), 4.05 (q, 2H), 2.34-2.40 (m, 2H), 1.65-1.85 (m, 4H), 1.12 (t, 3H).

In FIG. 8, the porphyrin carboxylate 2 is condensed with 6-aminohexanoic acid (3) using PyBOP to afford an amide (4). In an embodiment, amino acid (3) is replaced with amino acids L3 or L4, wherein the group P represents H. The value of n in L3 and L4 is selected from 1-12 and Y is OH.

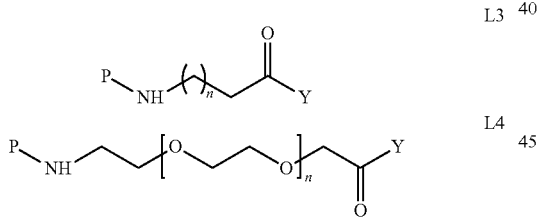

The anthracycline toxin illustrated in FIG. 8 is doxorubicin. However, in an embodiment, the anthracycline may be selected from the group T1b-T4b, where T1b is doxorubicin (Table 6).

FIG. 8 further describes the condensation of the amine in intermediate 2 with the carboxylic acid group of 4 using ByPOP to afford the conjugate OS007. Porphyrin 4 is in turn derived from porphyrins 2, which may be replaced by P1, wherein the carboxylic acid substituent (COOH) occupies ortho, meta or para positions, that is, positions 2, 3 or 4, and wherein the three substituents L, M and N may independently occupy the ortho, meta or para (positions 2, 3 or 4) on their respective aromatic rings. The substituents L, M ad N are selected from the set consisting of:

a) H;
b) carboxyaryl esters and acids (COOR) where the R may be H, lower straight chain or branched alkyl, cycloalkyl, hydroxy-substituted alkyl, polyethers (lower PEG), amino-substituted alkyl, hetero-substituted cycloalkyl and additionally, sugars. In addition, R may include aryl and heteroaryl substituents;
c) Carboxamides (CONR1R2), where wherein the R1 and R2 groups may individually be H, be lower straight chain or branched alkyl, cycloalkyl, hydroxy-substituted alkyl, polyethers (lower PEG), amino-substituted alkyl, hetero-substituted cycloalkyl. In addition, R may include aryl and heteroaryl substituents;
d) Aminoaryl groups (NR1R2) where R1 or R2 may individually be selected from the group lower alkyl, branched lower alkyl, cycloalkyl, or hetero-substituted alkyl or hetero-substituted cycloalkyl. R may also be an acyl group such as C(O)R, where R may include lower alkyl, hydroxy-substituted alkyl, polyethers (lower PEG), amino-substituted alkyl, cycloalkyl. In addition, R may include aryl and heteroaryl substituents;
e) Sulfur containing functional groups that may include thiols, sulfonicacids and corresponding amides thereof. The amides may be further defined as containing a nitrogen moiety NHR, with the N connected by a single bond to the sulfur atom, and where R is lower alkyl, cycloalkyl, or hetero-substituted alkyl or hetero-substituted cycloalkyl. R may also be an acyl group such as C(O)R, where R may include lower alkyl, hydroxy-substituted alkyl, polyethers (lower PEG), amino-substituted alkyl, cycloalkyl. In addition, R may include aryl and heteroaryl substituents;
f) Lower straight chain or branched alkyl groups, cycloalkyl groups, hydroxy-substituted alkyl, polyethers (lower PEG), amino-substituted alkyl, cycloalkyl and hetero-substituted cycloalkyl;
g) Oxygen groups such as hydroxy and substituted hydroxyaryl (OH or OR), where R may be chosen from the group including lower straight chain or branched alkyl groups, cycloalkyl groups, hydroxy-substituted alkyl, polyethers (lower PEG), amino-substituted alkyl, cycloalkyl and hetero-substituted cycloalkyl. In addition, R may include acyl (C(O)R), carbamoyloxy (C(O)NR1R2), aryl and heteroaryl substituents; and
h) Cyano or halogens (F, Cl, Br, I).

In a further embodiment, the carboxylate substituent (COOH) occupies the para (4-position) on its aromatic ring and further, the substituents on each of the other three aromatic rings are identical, that is L=M=N. Moreover, the substituents L, M and N are situated such that their positions on each aromatic ring are identical; for example, where each substituent occupies the meta position on its respective aromatic ring. A preferred embodiment is where the substituents L, M and N are all carboxylate (COOH) or carboxymethyl (COOMe) and are situated at the para position (i.e., 4-position) of their respective aromatic rings.

Figure 9:
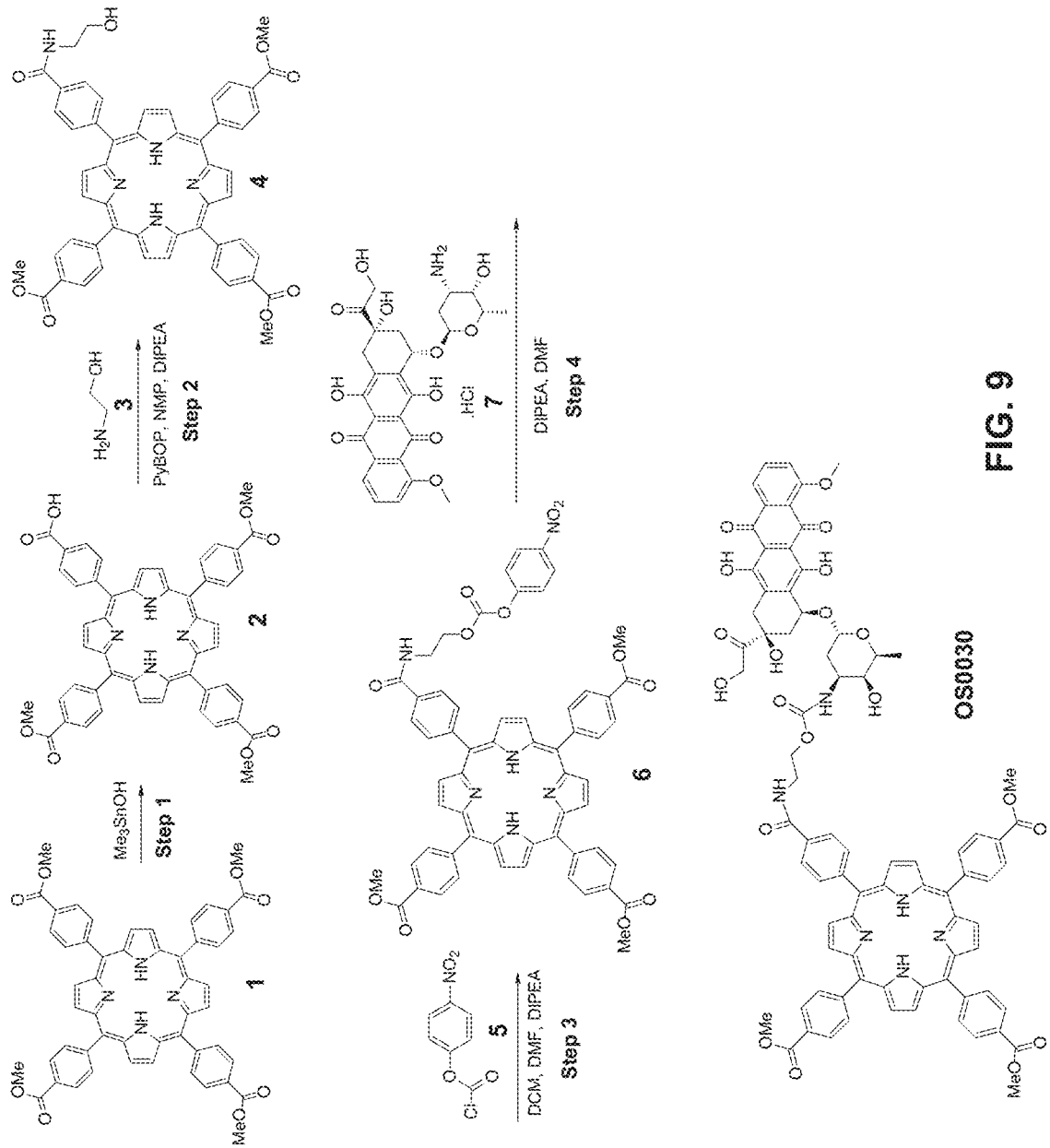
FIG. 9 illustrates a synthesis scheme for compound OS0030.

The procedure for synthesis of target OS0030 is illustrated in FIG. 9 and described below.

Preparation of 4-(10,15,20-tris(4-(methoxycarbonyl)phenyl)porphyrin-5-yl)benzoic acid (2). A mixture of 1 (1.0 g, 1.18 mmol) and Me₃SnOH (0.43 g, 2.36 mmol) in 1,2-dichloroethane (10 mL) was reacted in a microwave reactor at 150° C. for 1 h. The solvents were evaporated and absorbed on silica gel for purification. The silica-absorbed crude compound was purified by normal phase chromatography with 0-10% MeOH—$CH_2Cl_2$ (0.1% $CH_3COOH$) to get the desired compound 2 (275 mg, 28%). 41-NMR (300 MHz, DMSO-$d_6$): δ 17.0 (s, 1H), 13.2 (brs, 1H), 8.81-8.82 (m, 8H), 8.35-8.37 (m, 16H), 4.03 (s, 9H).

Preparation of trimethyl 4,4',4"-(20-(4-((2-hydroxyethyl)carbamoyl)phenyl)porphyrin-5,10,15-triyl)tribenzoate (4).

To a mixture of 2 (20 mg, 0.024 mmol), ethanol amine 3 (5.8 mg, 0.096 mmol) and PyBOP (19 mg, 0.036 mmol) in NMP (1 mL) was added DIPEA (20 µL, 0.12 mmol). The resultant mixture was stirred at ambient temperature overnight. The mixture was quenched with water (1 mL), extracted with $CH_2Cl_2$ (2×5 mL). The combined organic layers were washed with water, dried over $Na_2SO_4$, and evaporated. The crude compound was purified by normal phase chromatography with 0-10% MeOH—$CH_2Cl_2$ to get the desired compound 4 (14 mg, 67%) as purple solid. 41-NMR (300 MHz, $CDCl_3$): δ 12.09 (s, 1H), 8.80 (s, 8H), 8.26-8.45 (m, 16H), 6.92 (brs, 1H), 4.10 (s, 9H), 3.98-4.01 (m, 2H), 3.80-3.84 (m, 2H).

Preparation of trimethyl 4,4',4''-(20-(4-((2-(((4-nitrophenoxy)carbonyl)oxy)ethyl) carbamoyl)phenyl)porphyrin-5,10,15-triyl)tribenzoate (6). To a mixture of 4 (12 mg, 0.0137 mmol) and 5 (4 mg, 0.049 mmol) in $CH_2Cl_2$: DMF(8:2, 1 mL) was added DIPEA (12 µL g, 0.068 mmol) at room temperature. The resultant mixture was stirred for 4 h. The mixture was diluted with DCM (2 mL) and washed with water (2×10 mL), dried over $Na_2SO_4$, and evaporated. The crude residue was purified by normal phase chromatography with 0-10% MeOH—$CH_2Cl_2$ to obtain 6 (8 mg, 57%). $^1$H-NMR (300 MHz, $CDCl_3$): δ 12.17 (s, 1H), 8.81 (s, 8H), 8.16-8.43 (m, 18H), 7.42 (d, 2H), 6.84 (brt, 1H), 4.62-4.64 (m, 2H), 3.9-4.11 (m, 11H).

Preparation of trimethyl 4,4',4''-(20-(4-((2-(((((2S,3S,4S,6R)-3-hydroxy-2-methyl-6-(((1S,3S)-3,5,12-trihydroxy-3-(2-hydroxyacetyl)-10-methoxy-6,11-dioxo-1,2,3,4,6,11-hexahydrotetracen-1-yl)oxy)tetrahydro-2H-pyran-4-yl) carbamoyl)oxy)ethyl)carbamoyl) phenyl)porphyrin-5,10,15-triyl)tribenzoate (OS0030). To a mixture of 6 (8 mg, 0.0076 mmol) and doxorubicin.HCl 7 (3.7 mg, 0.0064 mmol) in DMF (0.8 mL) was added DIPEA (10 µL g, 0.061 mmol) at room temperature. The resultant mixture was stirred for 4 h. The mixture was diluted with $CH_2Cl_2$ (5 mL), The mixture was washed with water (2×5 mL), dried over $Na_2SO_4$, and evaporated. The crude residue was purified by normal phase chromatography with 0-10% MeOH—$CH_2Cl_2$ to give OS0030 (7 mg, 77%). $^1$H-NMR (300 MHz, DMSO-$d_6$): δ 12.0 (s, 1H), 9.90 (s, 3H), 8.88 (s, 8H), 7.66-7.79 (m, 3H), 7.52-7.65 (m, 9H), 7.36-7.7.42 (m, 1H), 7.18-7.26 (m, 3H), 4.12-4.20 (m, 2H), 4.05 (q, 2H), 2.34-2.40 (m, 2H), 1.65-1.85 (m, 4H), 1.12 (t, 3H).

In FIG. 9, the hydroxycarboxamide (4) is formed from the condensation of ethanolamine (3) with porphyrin carboxylate (2). In an embodiment, ethanolamine (3) may be replaced by aminoalcohols L5 or L6, wherein the group P represents H and n=1-12. The toxin illustrated in FIG. 9 is doxorubicin. However, in an embodiment, the anthracycline may be selected from the group T1b-T4b, where T1b is doxorubicin (Table 6). The carboxyaryl porphyrin (2) illustrated in FIG. 9 may, in an embodiment, also may be replaced by P1, where the carboxylic acid substituent (COOH) occupies ortho, meta or para, that is, positions 2, 3 or 4, and wherein the three substituents L, M and N may independently occupy the ortho, meta or para (positions 2, 3 or 4) on their respective aromatic rings. The substituents L, M ad N are selected from the set consisting of:
a) H;
b) carboxyaryl esters and acids (COOR) where the R may be H, lower straight chain or branched alkyl, cycloalkyl, hydroxy-substituted alkyl, polyethers (lower PEG), amino-substituted alkyl, hetero-substituted cycloalkyl and additionally, sugars. In addition, R may include aryl and heteroaryl substituents;
c) Carboxamides (CONR1R2), where wherein the R1 and R2 groups may individually be H, be lower straight chain or branched alkyl, cycloalkyl, hydroxy-substituted alkyl, polyethers (lower PEG), amino-substituted alkyl, hetero-substituted cycloalkyl. In addition, R may include aryl and heteroaryl substituents;
d) Aminoaryl groups (NR1R2) where R1 or R2 may individually be selected from the group lower alkyl, branched lower alkyl, cycloalkyl, or hetero-substituted alkyl or hetero-substituted cycloalkyl. R may also be an acyl group such as C(O)R, where R may include lower alkyl, hydroxy-substituted alkyl, polyethers (lower PEG), amino-substituted alkyl, cycloalkyl. In addition, R may include aryl and heteroaryl substituents;
e) Sulfur containing functional groups that may include thiols, sulfonic acids and corresponding amides thereof. The amides may be further defined as containing a nitrogen moiety NHR, with the N connected by a single bond to the sulfur atom, and where R is lower alkyl, cycloalkyl, or hetero-substituted alkyl or hetero-substituted cycloalkyl. R may also be an acyl group such as C(O)R, where R may include lower alkyl, hydroxy-substituted alkyl, polyethers (lower PEG), amino-substituted alkyl, cycloalkyl. In addition, R may include aryl and heteroaryl substituents;
f) Lower straight chain or branched alkyl groups, cycloalkyl groups, hydroxy-substituted alkyl, polyethers (lower PEG), amino-substituted alkyl, cycloalkyl and hetero-substituted cycloalkyl;
g) Oxygen groups such as hydroxy and substituted hydroxyaryl (OH or OR), where R may be chosen from the group including lower straight chain or branched alkyl groups, cycloalkyl groups, hydroxy-substituted alkyl, polyethers (lower PEG), amino-substituted alkyl, cycloalkyl and hetero-substituted cycloalkyl. In addition, R may include acyl (C(O)R), carbamoyloxy (C(O)NR1R2), wherein R1 and R2 may be H or lower alkyl, aryl and heteroaryl substituents.

In a preferred embodiment, the porphyrin is selected to be P1, wherein the carboxylic acid group is in the para position relative to the porphyrin ring, L, M and N are all carboxylic acid or carboxymethyl ester groups and are all in the para position relative to the porphyrin ring. Moreover, in this preferred embodiment, L5 is selected such that n=1 and P=H.

Figure 10:
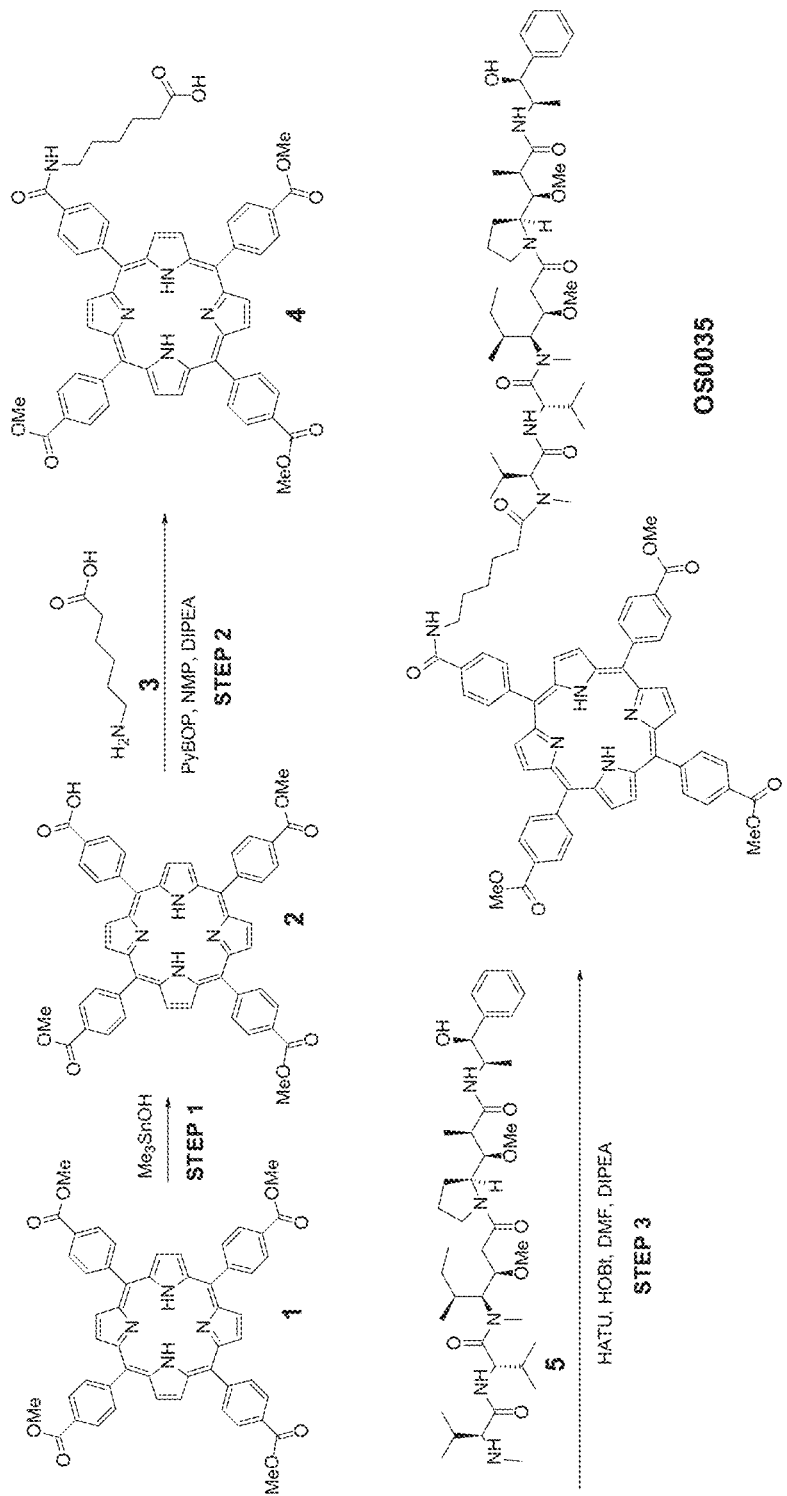
FIG. 10 illustrates a synthesis scheme for compound OS0035.

The procedure for synthesis of target OS0035 is illustrated in FIG. 10 and described below.

Preparation of 4-(10,15,20-tris(4-(methoxycarbonyl)phenyl)porphyrin-5-yl)benzoic acid (2). A mixture of 1 (1.0 g, 1.18 mmol) and $Me_3SnOH$ (0.43 g, 2.36 mmol) in 1,2-dichloroethane (10 mL) was reacted in a microwave reactor at 150° C. for 1 h. The solvents were evaporated and absorbed on silica gel for purification. The silica absorbed crude compound was purified by normal phase chromatography with 0-10% MeOH—$CH_2Cl_2$ (0.1% $CH_3COOH$) to get the desired compound 2 (275 mg, 28%). 41-NMR (300 MHz, DMSO-$d_6$): δ 17.0 (s, 1H), 13.2 (brs, 1H), 8.81-8.82 (m, 8H), 8.35-8.37 (m, 16H), 4.03 (s, 9H).

Preparation of 6-(4-(10,15,20-tris(4-(methoxycarbonyl) phenyl)porphyrin-5-yl)benzamido) hexanoic acid (4). A mixture of 2 (300 mg, 0.36 mmol), PyBOP (374 mg, 0.72 mmol) and DIPEA (0.48 mL, 2.8 mmol) in NMP (15 mL) was stirred for 10 min. at room temperature. To the above mixture was added 6-aminohexanoic acid (3, 188 mg, 1.44 mmol) and the resultant mixture was stirred at room temperature for 48 h. The mixture was diluted with $CH_2Cl_2$, washed with water (3×50 mL). The organic layer was dried over Na₂SO₄, and evaporated. The residue was purified by normal phase chromatography with 0-10% MeOH—CH₂Cl₂ to obtain the desired compound 4 (89 mg, 26%). ¹H-NMR (300 MHz, CDCl₃): δ 12.17 (s, 1H), 8.80 (s, 8H), 8.14-8.44 (m, 16H), 6.39 (brt, 1H), 3.51-3.62 (m, 2H), 2.40-2.45 (m, 2H), 1.45-1.79 (m, 6H).

MeOH—CH₂Cl₂ to get the desired target compound OS0035 (12 mg, 33%).

FIG. 10 illustrates the condensation of the secondary amine of monomethylauristatin E (5), with the carboxylate of intermediate 4, using peptide coupling reagent HATU, to afford OS0035. In an embodiment, the 5 may be replaced with auristatin-related peptides T5c, T9c and T10c (Table 8).

TABLE 8

Auristatin-related peptides

[Chemical structures of T4c, T5c, T9c, and T10c shown]

Preparation trimethyl 4,4',4"-(20-(4-(((3R,4S,7S,10S)-4-((S)-sec-butyl)-3-(2-((S)-2-41R,2R)-3-(((1S,2R)-1-hydroxy-1-phenylpropan-2-yl)amino)-1-methoxy-2-methyl-3-oxopropyl)pyrrolidin-1-yl)-2-oxoethyl)-7,10-diisopropyl-5,11-dimethyl-6,9,12-trioxo-2-oxa-5,8,11-triazaheptadecan-17-yl)carbamoyl)phenyl)porphyrin-5,10,15-triyl) tribenzoate (OS0035). To a mixture of 4 (21 mg, 0.022 mmol), HATU (20.2 mg, 0.053 mmol) and DIPEA (31 μL, 0.177 mmol) in DMF (2 mL) was stirred for 10 min at room temperature. To the above mixture was added monomethyl auristatin E (5, 17.5 mg, 0.024 mmol) followed by HOBt (3.3 mg, 0.024 mmol) and the resultant mixture was stirred at room temperature for 16 h. The mixture was diluted with CH₂Cl₂ and washed with water (3×10 mL). The organic layer was dried over Na₂SO₄, and evaporated. The residue was purified by normal phase chromatography with 0-10%

In another embodiment, the amino acid 3 is replaced by a protected L3 or L4, where P═H and n=1-12 and wherein Y is OH.

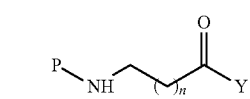

L3

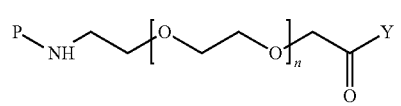

L4

In FIG. 10, the porphyrin carboxylate (2) is condensed with the primary amine 3 to form the amide bond affording the intermediate carboxylate 4, which in turn is condensed with MMAE (5) to afford OS0035. However, in another embodiment, 2 may be replaced by P1, where the carboxylic acid substituent (COOH) occupies ortho, meta or para positon, that is, positions 2, 3 or 4, relative to the porphyrin ring and wherein the three substituents L, M and N may independently occupy the ortho, meta or para (positions 2, 3 or 4) on their respective aromatic rings. The substituents L, M ad N are selected from the set consisting of:

a) H;
b) carboxyaryl esters and acids (COOR) where the R may be H, lower straight chain or branched alkyl, cycloalkyl, hydroxy-substituted alkyl, polyethers (lower PEG), amino-substituted alkyl, hetero-substituted cycloalkyl and additionally, sugars. In addition, R may include aryl and heteroaryl substituents;
c) Carboxamides (CONR1R2), where wherein the R1 and R2 groups may individually be H, be lower straight chain or branched alkyl, cycloalkyl, hydroxy-substituted alkyl, polyethers (lower PEG), amino-substituted alkyl, hetero-substituted cycloalkyl. In addition, R may include aryl and heteroaryl substituents;
d) Aminoaryl groups (NR1R2) where R1 or R2 may individually be selected from the group lower alkyl, branched lower alkyl, cycloalkyl, or hetero-substituted alkyl or hetero-substituted cycloalkyl. R may also be an acyl group such as C(O)R, where R may include lower alkyl, hydroxy-substituted alkyl, polyethers (lower PEG), amino-substituted alkyl, cycloalkyl. In addition, R may include aryl and heteroaryl substituents;
e) Sulfur containing functional groups that may include thiols, sulfonic acids and corresponding amides thereof. The amides may be further defined as containing a nitrogen moiety NHR, with the N connected by a single bond to the sulfur atom, and where R is lower alkyl, cycloalkyl, or hetero-substituted alkyl or hetero-substituted cycloalkyl. R may also be an acyl group such as C(O)R, where R may include lower alkyl, hydroxy-substituted alkyl, polyethers (lower PEG), amino-substituted alkyl, cycloalkyl. In addition, R may include aryl and heteroaryl substituents;
f) Lower straight chain or branched alkyl groups, cycloalkyl groups, hydroxy-substituted alkyl, polyethers (lower PEG), amino-substituted alkyl, cycloalkyl and hetero-substituted cycloalkyl;
g) Oxygen groups such as hydroxy and substituted hydroxyaryl (OH or OR), where R may be chosen from the group including lower straight chain or branched alkyl groups, cycloalkyl groups, hydroxy-substituted alkyl, polyethers (lower PEG), amino-substituted alkyl, cycloalkyl and hetero-substituted cycloalkyl. In addition, R may include acyl (C(O)R), carbamoyloxy (C(O)NR1R2), where R1 and R2 are lower alkyl, aryl and heteroaryl substituents.

In a preferred embodiment, the porphyrin is selected to be P1, wherein the carboxylic acid group is in the para position relative to the porphyrin ring, L, M and N are all carboxylic acid or carboxymethyl ester groups and are all in the para position relative to the porphyrin ring. Moreover, in this preferred embodiment, L3 is selected such that n=4 and P=H. In this embodiment, the toxin is T4c (Table 8).

Figure 11:
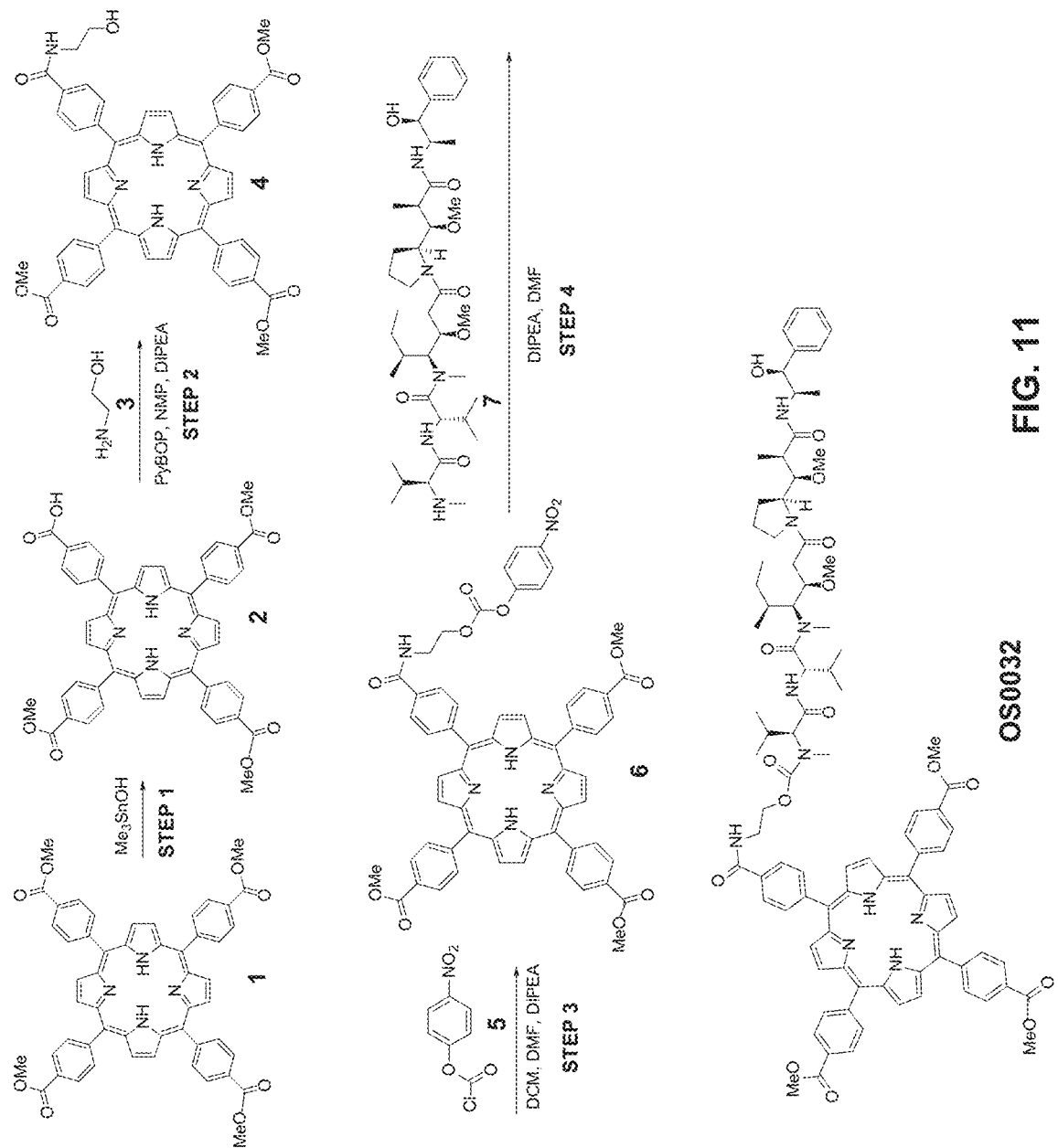
FIG. 11 illustrates a synthesis scheme for compound OS0032.

The procedure for synthesis of target OS0032 is illustrated in FIG. 11 and described below.

Preparation of 4-(10,15,20-tris(4-(methoxycarbonyl)phenyl)porphyrin-5-yl)benzoic acid (2). A mixture of tetra methyl porphyrin ester (1) (1.0 g, 1.18 mmol) and Me3SnOH (0.43 g, 2.36 mmol) in 1,2-dichloroethane (10 mL) was reacted in a microwave reactor at 150° C. for 1 h. The solvents were evaporated and absorbed on silica gel for purification. The silica absorbed crude compound was purified by normal phase chromatography with 0-10% MeOH—$CH_2Cl_2$ (0.1% $CH_3COOH$) to get the desired compound 2 (275 mg, 28%). $^1$H-NMR (300 MHz, DMSO-d6): δ 17.0 (s, 1H), 13.2 (br s, 1H), 8.81-8.82 (m, 8H), 8.35-8.37 (m, 16H), 4.03 (s, 9H).

Preparation of trimethyl 4,4',4"-(20-(4-((2-hydroxyethyl)carbamoyl)phenyl)porphyrin-5,10,15-triyl)tribenzoate (4). To a mixture of 2 (20 mg, 0.024 mmol), ethanol amine (3) (5.8 mg, 0.096 mmol) and PyBOP (19 mg, 0.036 mmol) in NMP (1 mL) was added DIPEA (20 μL, 0.12 mmol). The resultant mixture was stirred at ambient temperature overnight. The mixture was quenched with water (1 mL) and extracted with $CH_2Cl_2$ (2×5 mL). The combined organic layers were washed with water, dried over $Na_2SO_4$, and evaporated. The crude compound was purified by ISCO with 0-10% MeOH—$CH_2Cl_2$ to get the desired compound 4 (14 mg, 67%) as purple solid. $^1$H-NMR (300 MHz, $CDCl_3$): δ 12.09 (s, 1H), 8.80 (s, 8H), 8.26-8.45 (m, 16H), 6.92 (brs, 1H), 4.10 (s, 9H), 3.98-4.01 (m, 2H), 3.80-3.84 (m, 2H).

Preparation of trimethyl 4,4',4"-(20-(4-((2-(((4-nitrophenoxy)carbonyl)oxy) ethyl) carbamoyl)phenyl)porphyrin-5,10,15-triyl)tribenzoate (6). To a mixture of 4 (12 mg, 0.0137 mmol) and p-nitrophenyl chloroformate 5 (4 mg, 0.049 mmol) in $CH_2Cl_2$: DMF (8:2, 1 mL) was added DIPEA (12 μL g, 0.068 mmol) at room temperature. The resultant mixture was stirred for 4 h. The mixture was diluted with DCM (2 mL), washed with water (2×10 mL), dried over $Na_2SO_4$, and evaporated. The crude residue was purified by normal phase chromatography with 0-10% MeOH—$CH_2Cl_2$ to give 6 (8 mg, 57%). $^1$H-NMR (300 MHz, $CDCl_3$): δ 12.17 (s, 1H), 8.81 (s, 8H), 8.16-8.43 (m, 18H), 7.42 (d, 2H), 6.84 (brt, 1H), 4.62-4.64 (m, 2H), 3.9-4.11 (m, 11H).

Preparation of trimethyl 4,4',4"-(20-(4-(03R,4S,7S,10S)-4-((S)-sec-butyl)-3-(2-((S)-2-((1R,2R)-3-(((1S,2R)-1-hydroxy-1-phenylpropan-2-yl)amino)-1-methoxy-2-methyl-3-oxopropyl) pyrrolidin-1-yl)-2-oxoethyl)-7,10-diisopropyl-5,11-dimethyl-6,9,12-trioxo-2,13-dioxa-5,8,11-triazapentadecan-15-yl)carbamoyl)phenyl)porphyrin-5,10,15-triyl)tribenzoate (OS0032). To a mixture of 6 (20 mg, 0.019 mmol) and monomethyl auristatin E 7 (15.1 mg, 0.021 mmol) in DMF (0.8 mL) was added DIPEA (27 μL g, 0.153 mmol) at room temperature. The resultant mixture was stirred for 16 at ambient temperature. The mixture was diluted with $CH_2Cl_2$ (5 mL), washed with water (2×10 mL), dried over $Na_2SO_4$, and evaporated. The crude residue was purified by normal phase chromatography with 0-10% MeOH—$CH_2Cl_2$ to give the desired target OS0032 (15 mg, 77%). $^1$H-NMR (300 MHz, $CDCl_3$): δ 8.85 (s, 8H), 8.43 (d, 6H, J=8), 8.18-8.33 (m, 10H), 7.21-7.31 (m, 5H), 6.43 (m, 1H), 3.80-4.89 (m, 17H), 3.75 (d, 1H, J=7), 3.19-3.34 (m, 9H), 2.97 (m, 6H), 2.31-2.42 (m, 4H), 1.97-2.18 (m, 3H), 1.60-1.75 (M, 3h), 1.17-1.38 (M, 5H), 0.68-0.97 (m, 26H).

In FIG. 11, a hydroxyamide intermediate (4) is formed from the condensation of porphyrin carboxylate 2 with ethanolamine (3).

In one embodiment, the 3 is replaced by aminoalcohols L5 or L6, wherein the group P represents H and n=1-12.

In another embodiment, MMAE (7) may be replaced with auristatin-related peptides T5c, T9c and T10c (Table 8). MMAE is denoted as T4c in Table 8.

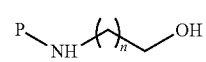

L5

-continued

L6

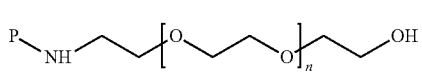

In another embodiment, porphyrin (2) may be replaced by P1, where the carboxylic acid substituent (COOH) occupies ortho, meta or para, that is, positions 2, 3 or 4, and wherein the three substituents L, M and N may independently occupy the ortho, meta or para (positions 2, 3 or 4) on their respective aromatic rings. The substituents L, M ad N are selected from the set consisting of:
a) H;
b) carboxyaryl esters and acids (COOR) where the R may be H, lower straight chain or branched alkyl, cycloalkyl, hydroxy-substituted alkyl, polyethers (lower PEG), amino-substituted alkyl, hetero-substituted cycloalkyl and additionally, sugars. In addition, R may include aryl and heteroaryl substituents;
c) Carboxamides (CONR1R2), where wherein the R1 and R2 groups may individually be H, be lower straight chain or branched alkyl, cycloalkyl, hydroxy-substituted alkyl, polyethers (lower PEG), amino-substituted alkyl, hetero-substituted cycloalkyl. In addition, R may include aryl and heteroaryl substituents;
d) Aminoaryl groups (NR1R2) where R1 or R2 may individually be selected from the group lower alkyl, branched lower alkyl, cycloalkyl, or hetero-substituted alkyl or hetero-substituted cycloalkyl. R may also be an acyl group such as C(O)R, where R may include lower alkyl, hydroxy-substituted alkyl, polyethers (lower PEG), amino-substituted alkyl, cycloalkyl. In addition, R may include aryl and heteroaryl substituents;
e) Sulfur containing functional groups that may include thiols, sulfonic acids and corresponding amides thereof. The amides may be further defined as containing a nitrogen moiety NHR, with the N connected by a single bond to the sulfur atom, and where R is lower alkyl, cycloalkyl, or hetero-substituted alkyl or hetero-substituted cycloalkyl. R may also be an acyl group such as C(O)R, where R may include lower alkyl, hydroxy-substituted alkyl, polyethers (lower PEG), amino-substituted alkyl, cycloalkyl. In addition, R may include aryl and heteroaryl substituents;
f) Lower straight chain or branched alkyl groups, cycloalkyl groups, hydroxy-substituted alkyl, polyethers (lower PEG), amino-substituted alkyl, cycloalkyl and hetero-substituted cycloalkyl;

g) Oxygen groups such as hydroxy and substituted hydroxyaryl (OH or OR), where R may be chosen from the group including lower straight chain or branched alkyl groups, cycloalkyl groups, hydroxy-substituted alkyl, polyethers (lower PEG), amino-substituted alkyl, cycloalkyl and hetero-substituted cycloalkyl. In addition, R may include acyl (C(O)R), carbamoyloxy (C(O) NR1R2), where R1 and R2 may be H or lower alkyl, aryl and heteroaryl substituents.

In a preferred embodiment, the aminoalcohol L5 is chosen such that P is H and n=1. The porphyrin in this embodiment is selected to be P1, wherein the carboxylic acid group is in the para position relative to the porphyrin ring, L, M and N are all carboxylic acid or carboxymethyl ester groups and are all in the para position relative to the porphyrin ring. Moreover, the toxin is MMAE (T4c).

Figure 12:
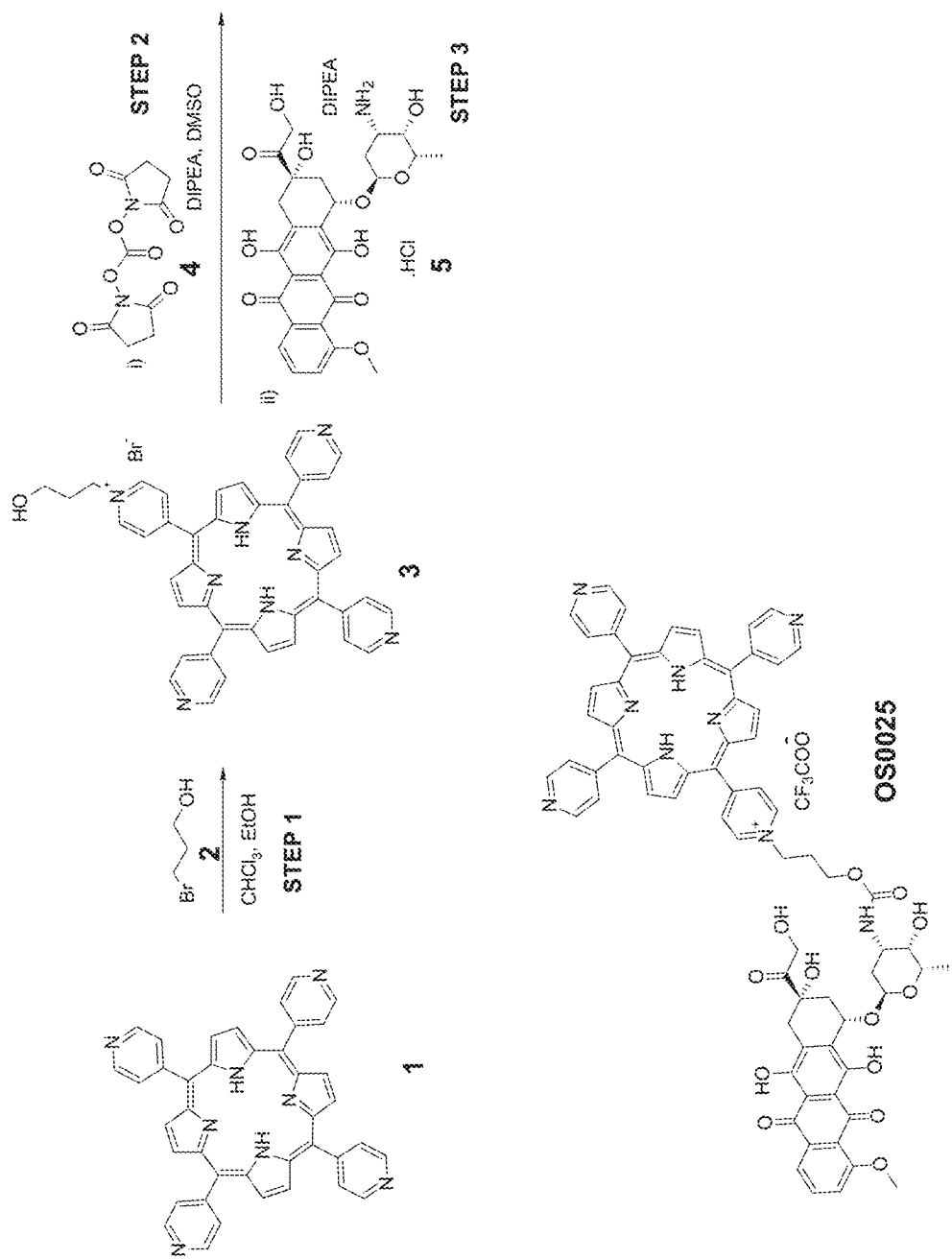
FIG. 12 illustrates a synthesis scheme for compound OS0025.

The procedure for synthesis of target OS0025 is illustrated in FIG. 12 and described below.

Preparation of 1-(3-hydroxypropyl)-4-(10,15,20-tri(pyridin-4-yl)porphyrin-5-yl)pyridin-1-ium (3). A mixture of 1 (1.26 g, 2.03 mmol) and 3-bromo-1-propanol 2 (0.43 g, 2.36 mmol) in a mixture of EtOH and $CHCl_3$ (400 mL, 1:3) was refluxed for 6 d. The solvents were evaporated and absorbed on silica for purification. The silica absorbed crude compound was purified by two short silica gel columns ($CH_2Cl_2$: EtOH, 7:3, v/v) to get the desired compound 3 (74 mg, 6%). $^1$H-NMR (300 MHz, DMSO-$d_6$): δ 11.9 (s, 1H), 9.5 (d, 2H), 8.81-9.08 (m, 16H), 8.27 (d, 6H), 5.00-5.03 (m, 3H), 2.75-2.77 (m, 2H), 2.32-2.35 (m, 2H). MS m/z=677 $[M]^+$.

Preparation of 1-(3-((((2S,3S,4S,6R)-3-hydroxy-2-methyl-6-0(1S,3S)-3,5,12-trihydroxy-3-(2-hydroxyacetyl)-10-methoxy-6,11-dioxo-1,2,3,4,6,11-hexahydrotetracen-1-yl)oxy)tetrahydro-2H-pyran-4-yl)carbamoyl)oxy)propyl)-4-(10,15,20-tri(pyridin-4-yl)porphyrin-5-yl)pyridin-1-ium (OS0025). To a mixture of 3 (23 mg, 0.034 mmol) and 4 (13 mg, 0.05 mmol) in DMSO-$d_6$ (1 mL) was added DIPEA (9 μL, 0.05 mmol). The resultant mixture was stirred at ambient temperature overnight. The HPLC showed new peak and consumption of 3. At this point of time, was added 5 (20 mg, 0.034 mmol) followed by DIPEA (18 μL, 0.1 mmol). The reaction mixture was stirred at room temperature for 7 h and stored at 0° C. over 64 h. The mixture was diluted with 9 mL of chloroform. The supernatant layer was collected after centrifugation (15 min, 3000 rpm) and evaporated. The residue was purified by reverse phase ISCO with water-acetonitrile (0.1% TFA) to get the desired compound 6 (12.5 mg, 30%) as purple solid. MS (ESI) m/z=1247 $[M]^+$. Purity by HPLC (ELSD): >89%, $t_R$=3.58.

HPLC Condition.

Agilent Tech 1100 series HPLC System equipped with Variable Wavelength Detector and ELSD Detector and UV at 254 nm Column: Agela, Durashell C18, 3.0 μm, 4.60×50 mm.

Mobile Phase: A (ACN with 0.1% TFA)

Mobile Phase: D ($H_2O$ with 0.1% TFA)

Gradient

| Time | A (ACN with 0.1% TFA) | D ($H_2O$ with 0.1% TFA) |
|---|---|---|
| 0 | 5 | 95 |
| 5.75 | 95 | 5 |
| 8 | 95 | 5 |
| 9 | 5 | 95 |

The synthetic scheme illustrates the alkylation of meso-tetrakis(4-pyridyl)porphyrin (1) with 1-bromo-3-propanol (2) to afford pyridinium intermediate 3 via an $S_N2$ reaction. In an embodiment, the bromoalcohol (2) may be replaced with related bromoalcohols L7 and L8, where n is selected from 1-12.

L7

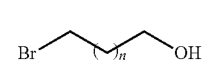

L8

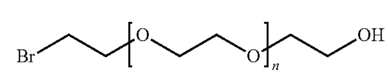

The porphyrin 1 may also be substituted by P2, wherein the position of the heteroatom is one of X, Y or Z on the four aromatic rings. Thus, on each pyridine ring of P2, a nitrogen (N) is positioned at either X or Y or Z, with CH occupying the remaining two positions. For example, the porphyrin meso-tetrakis(3-pyridyl)porphyrin could be represented as Y is N, X and Z are CH on all four pyridine rings. In a general embodiment, the position of the N on each ring may differ. In a more preferred embodiment, the position of the N atom in each pyridine ring is the same in all four pyridine rings. In a preferred embodiment, the porphyrin meso-tetrakis(4-pyridyl)porphyrin could be represented as X=N, Y and Z are CH on all four pyridine rings.

FIG. 12 further illustrates the reaction of the activated carbonate 4 with the aminosugar of doxorubicin to afford the carbamate moiety in OS0025. In another embodiment, doxorubicin may be replaced with an anthracycline selected from the group T1b-T4b, wherein T1b is doxorubicin (Table 6).

In a preferred embodiment, P2 is selected such that X=N, Y=Z=CH; L7 is selected such that n=1; and Tnb is selected as T1b (doxorubicin).

Figure 13:
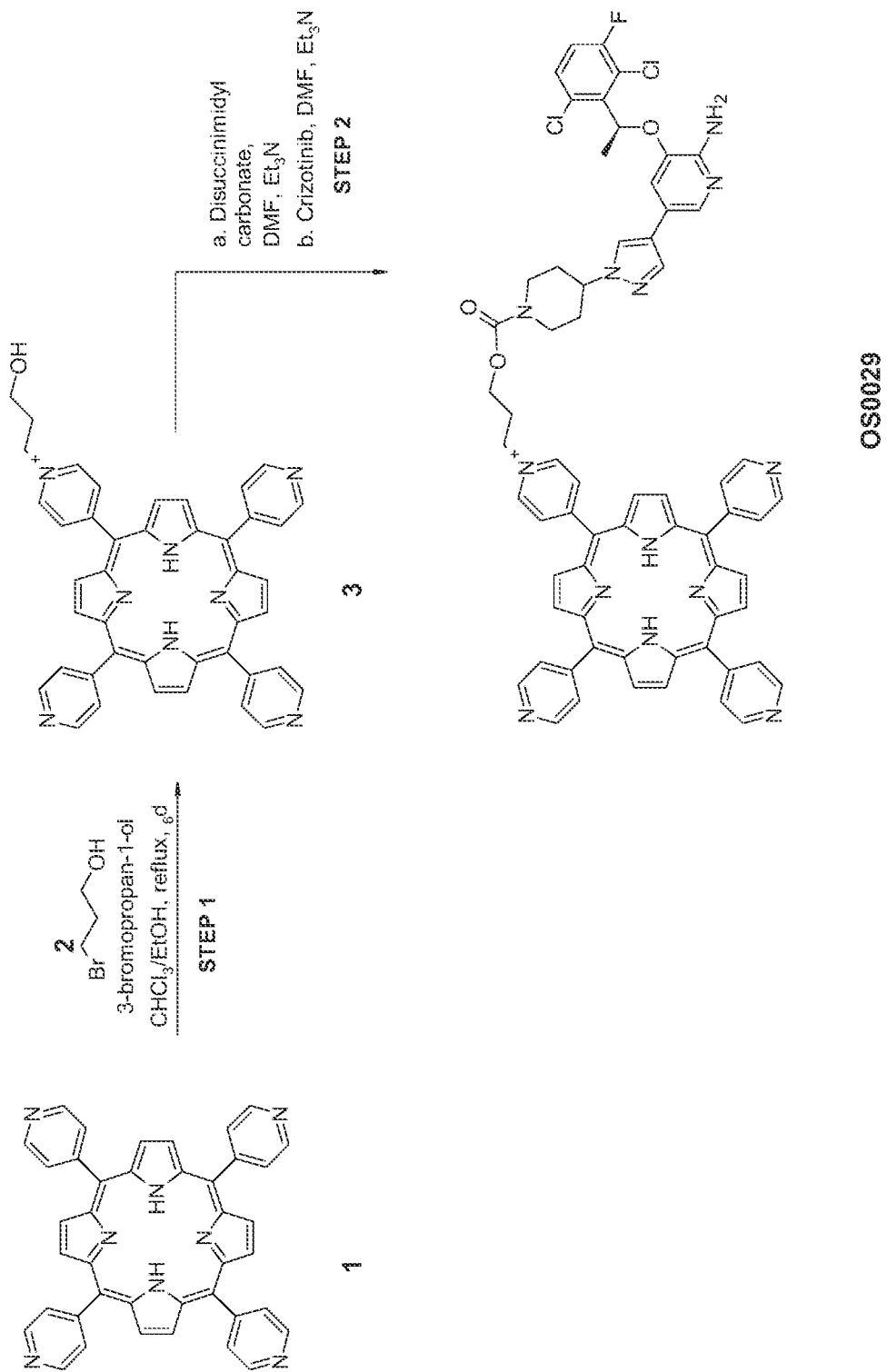
FIG. 13 illustrates a synthesis scheme for compound OS0029.

The procedure for the synthesis of target OS0029 is illustrated in FIG. 13 and described below.

Preparation of 1-(3-hydroxypropyl)-4-(10,15,20-tri(pyridin-4-yl)porphyrin-5-yl)pyridin-1-ium (3). A mixture of 1 (1.26 g, 2.03 mmol) and 2 (3.31 g, 23.86 mmol) in a mixture of EtOH and $CHCl_3$ (400 mL, 1:3) was refluxed for 6 d. The solvents were evaporated and adsorbed on silica for purification. The silica adsorbed crude compound was purified by two successive short silica gel columns ($CH_2Cl_2$:EtOH, 7:3, v/v) to get the desired compound 3 (74 mg, 6%). $^1$H-NMR (300 MHz, DMSO-$d_6$): δ 11.9 (s, 1H), 9.5 (d, 2H), 8.81-9.08 (m, 16H), 8.27 (d, 6H), 5.00-5.03 (m, 3H), 2.75-2.77 (m, 2H), 2.32-2.35 (m, 2H). MS m/z=677 $[M]^+$.

Preparation of (S)-1-(3-((4-(4-(4-amino-3-(1-(2,6-dichloro-3-fluorophenyl)ethoxy)phenyl)-1H-pyrazol-1-yl)piperidine-1-carbonyl)oxy)propyl)-4-(10,15,20-tri(pyridin-4-yl)porphyrin-5-yl)pyridin-1-ium (OS0029). To a mixture of 3 (30 mg, 0.044 mmol) and disuccinimidyl carbonate (13.6 mg, 0.05 mmol) in DMSO-$d_6$ (1.5 mL) was added DIPEA (11 µL, 0.066 mmol). The resultant mixture was stirred at ambient temperature overnight. The HPLC showed new peak and consumption of 3. At this point of time, was added crizotinib hydrochloride (25.8 mg, 0.053 mmol) followed by DIPEA (22 µL, 0.066 mmol). Then the mixture was stirred at room temperature for 7 h and stored at 0° C. over 64 h. The crude mixture was loaded on reverse phase column and eluted with 0-100% acetonitrile-water (0.1% TFA). The pure fractions were collected and lyophilized. The solid was triturated/sonicated with chloroform (5 mL×4) and the supernatant layer was separated. The remaining solid was dried under vacuum overnight to yield 6 (23 mg, 45%). MS (ESI) m/z=1152.3 $[M]^+$. Purity by HPLC (ELSD): >97%, $t_R$=4.58.

HPLC Condition.
Agilent Tech 1100 series HPLC System equipped with Variable Wavelength Detector and ELSD Detector
Column: Agela, Durashell C18, 3.0 µm, 4.60×50 mm.
Mobile Phase: A (ACN with 0.1% TFA)
Mobile Phase: D ($H_2O$ with 0.1% TFA)
Gradient

| Time | A (ACN with 0.1% TFA) | D ($H_2O$ with 0.1% TFA) |
|---|---|---|
| 0 | 5 | 95 |
| 5.75 | 95 | 5 |
| 8 | 95 | 5 |
| 9 | 5 | 95 |

Detection: UV at 254 nm

FIG. 13 illustrates the alkylation of meso-tetrakis(4-pyridyl)porphyrin (1) with 1-bromo-3-propanol (2) to afford hydroxypyridinium intermediate 3 via an $S_N2$ reaction. In an embodiment, the bromoalcohol (2) may be replaced by L7 and L8, wherein n=1-12. The porphyrin 1 may be replaced with porphyrins P2, wherein the position of the heteroatom is one of X, Y or Z on the four aromatic rings. Thus, on each pyridine ring of P2, a nitrogen (N) is positioned at either X or Y or Z, with CH occupying the remaining two positions. For example, the porphyrin meso-tetrakis(3-pyridyl)porphyrin could be represented as Y is N, X and Z are CH on all four pyridine rings. In a general embodiment, the position of the N on each ring may differ. In a more preferred embodiment, the position of the N atom in each pyridine ring is the same in all four pyridine rings. In a preferred embodiment, the porphyrin meso-tetrakis(4-pyridyl)porphyrin could be represented as X=N, Y and Z are CH on all four pyridine rings. FIG. 13 further illustrates the reaction of 3 with disuccimidyl carbonate to form an activated carbonate intermediate, which is subsequently reacted in Step 3 with the secondary amine of cirizotinib to afford OS0029.

Further, the crizotinib may be replaced in this condensation reaction by kinase inhibitors (T1a-T33a), as shown in Table 7.

In a preferred embodiment, P2 is selected such that X=N, Y=Z=CH; L7 is selected such that n=1; and crizotinib is the toxin.

Figure 14:
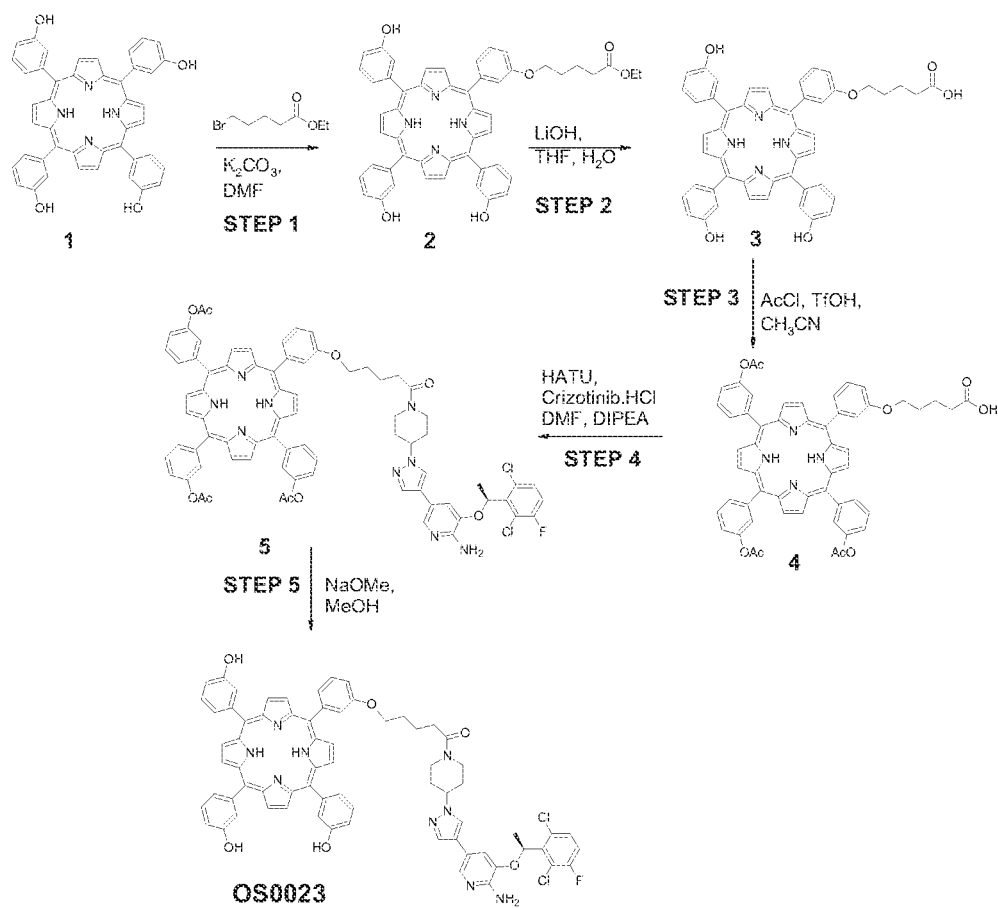
FIG. 14 illustrates a synthesis scheme for compound OS0023.

The procedure for synthesis of target OS0023 is illustrated in FIG. 14 and described below.

Synthesis of ethyl 5-(3-(10,15,20-tris(3-hydroxyphenyl)porphyrin-5-yl)phenoxy) pentanoate) (2). A mixture of 1 (1.25 g, 1.84 mmol) and $K_2CO_3$ (0.5 g) in DMF (30 mL) was stirred under nitrogen at room temperature for 30 min. Ethyl 5-bromopentanoate (1.15 g, 5.5 mmol, 3 eq.) was added. The mixture was stirred at room temperature overnight. The mixture was diluted with DCM, washed with water, satd. $NaHCO_3$(aq), water and brine, dried over $Na_2SO_4$, and evaporated. The crude residue was purified with two successive column chromatography to give 2 (0.42 g, 28%). $^1$H-NMR (300 MHz, DMSO-$d_6$): δ 12.0 (s, 1H), 9.90 (s, 3H), 8.88 (s, 8H), 7.66-7.79 (m, 3H), 7.52-7.65 (m, 9H), 7.36-7.7.42 (m, 1H), 7.18-7.26 (m, 3H), 4.12-4.20 (m, 2H), 4.05 (q, 2H), 2.34-2.40 (m, 2H), 1.65-1.85 (m, 4H), 1.12 (t, 3H).

Synthesis 5-(3-(10,15,20-tris(3-hydroxyphenyl)porphyrin-5-yl)phenoxy)pentanoic acid (3). To a solution of 2 (157 mg, 0.19 mmol) in THF (45 mL) was added a solution of LiOH—$H_2O$ (0.15 g) in water (30 mL) at room temperature. The mixture was stirred at room temperature overnight. Evaporated THF, diluted with satd. $NH_4Cl$ (aq), extracted with DCM, washed with brine, and evaporated. The intermediate was used for next step reaction without further purification. 3 (0.14 g, 92%) $^1$H-NMR (300 MHz, DMSO-$d_6$): δ 12.0 (s, 2H), 9.90 (s, 3H), 8.89 (s, 8H), 7.66-7.82 (m, 3H), 7.54-7.65 (m, 9H), 7.36-7.7.42 (m, 1H), 7.20-7.26 (m, 3H), 4.14-4.22 (m, 2H), 2.26-2.36 (m, 2H), 1.65-1.85 (m, 4H).

Synthesis 5-(3-(10,15,20-tris(3-acetoxyphenyl)porphyrin-5-yl)phenoxy)pentanoic acid (4). To a mixture of 3 (67 mg, 0.068 mmol) in 1% TfOH/$CH_3CN$ (25 mL) was added AcCl (1.5 mL) at room temperature. The reaction was stirred at same temperature for 2 h then poured into cold half concentrated $NaHCO_3$ and EtOAc, extracted with EtOAc, washed with brine and solvents evaporated. The crude residue was purified with column chromatography to give 4 (75 mg, 95%)$^1$H-NMR (300 MHz, $CDCl_3$): δ 12.1 (s, 1H), 8.91 (s, 8H), 8.03-8.10 (m, 3H), 7.92-7.98 (m, 3H), 7.70=7.81 (m, 5H), 7.58-7.64 (m, 1H), 7.49-7.56 (m, 3H), 7.32-7.28 (m, 1H), 4.05-4.20 (m, 2H), 2.28-2.35 (m, 2H), 2.37 (s, 9H), 1.84-194 (m, 4H).

Synthesis (S)-(20-(3-((5-(4-(4-(6-amino-5-(1-(2,6-dichloro-3-fluorophenyl)ethoxy)pyridin-3-yl)-1H-pyrazol-1-yl)piperidin-1-yl)-5-oxopentyl)oxy)phenyl)porphyrin-5,10,15-triyl)tris(benzene-3,1-diyl) triacetate (5). To a solution of 4 (80 mg, 0.087 mmol) in DMF (6 mL) was added HATU (77 mg, 0.2 mmol, 2.3 eq.) and DIPEA (104 μL. Stirred at room temperature for 5 min. crizotinib-HCl (47 mg, 0.096 mmol, 1.1 eq.) was added. The mixture was stirred at room temperature overnight. The DMF solvent was evaporated, the residue was dissolved to EtOAc, then washed with water and brine. The crude residue was purified by a normal phase column chromatography to afford 5 (71 mg, 61%); MS [M+1]$^+$=1336.

Synthesis (S)-1-(4-(4-(6-amino-5-(1-(2,6-dichloro-3-fluorophenyl)ethoxy)pyridin-3-yl)-1H-pyrazol-1-yl)piperidin-1-yl)-5-(3-(10,15,20-tris(3-hydroxyphenyl)porphyrin-5-yl)phenoxy)pentan-1-one (OS0023). To a solution of 5 (71 mg, 0.053 mmol) in MeOH/DMF (20 mL/6 mL) was added a solution of NaOMe in methanol (3.2 mL, 50 mM, 1 eq.) at 0° C. The reaction was monitored by HPLC. Stirred at same temperature for 1 h then warmed to room temperature. After stirring at room temperature for 2 h, HPLC indicated that the reaction was complete. The reaction was quenched with a solution of HOAc in MeOH (0.4 mL/2 mL). Concentrated, the residue was dissolved into EtOAc, washed with water and brine. After evaporating the solvents, the residue was purified by a normal phase column chromatography to afford the desired target OS0023 (35 mg, 55%). MS [M+1]+=1210.

FIG. 14 illustrates the condensation of the secondary amine of crizotinib with the carboxylate group of intermediate 4 using the peptide coupling reagent HATU to afford intermediate 5. In an embodiment crizotinib may be replaced with other kinase inhibitors chosen from the set illustrated in Table 7, wherein crizotinib is compound 1 in Table 7.

Moreover, in another embodiment, the ethyl 5-bromopentanoate used in the synthesis of OS0023 may be replaced with either L1 or L2, wherein Y represents OH and the n is selected from 1-12 for L1 and L2. X represents a leaving group suitable for an $S_N2$ reaction with a nucleophile, such as a phenol or its conjugate base. In this context, the leaving group X is either a halogen leaving groups (Cl, Br, I) or a variety of activated sulfonyl esters such as mesylates, tosylates or triflates.

FIG. 14 illustrates the alkylation of meso-tetrakis(3-hydroxyphenyl)porphyrin (1) to afford intermediate 2. In yet another embodiment, the phenolic porphyrin 1 is replaced by porphyrin P4, wherein the hydroxy substituent could be situated at the ortho, meta or para positions (positions 2, 3 or 4) of the aromatic ring and, moreover, where the substituents L, M and N, may be independently occupy the ortho, meta or para, that is 2-, 3- or 4-positions, on their respective aromatic rings. The substituents L, M ad N are selected from the group consisting of:

a) H;
b) carboxyaryl esters and acids (COOR) where the R may be H, lower straight chain or branched alkyl, cycloalkyl, hydroxy-substituted alkyl, polyethers (lower PEG), amino-substituted alkyl, heterosubstituted cycloalkyl and additionally, sugars. In addition, R may include aryl and heteroaryl substituents;
c) Carboxamides (CONR1R2), where wherein the R1 and R2 groups may individually be H, be lower straight chain or branched alkyl, cycloalkyl, hydroxy-substituted alkyl, polyethers (lower PEG), amino-substituted alkyl, heterosubstituted cycloalkyl. In addition, R may include acyl (C(O)R1), carbamoyloxy (C(O)NR1R2), aryl and heteroaryl substituents;
d) Aminoaryl groups (NR1R2) where R1 or R2 may individually be selected from the group lower alkyl, branched lower alkyl, cycloalkyl, or heterosubstituted alkyl or heterosubstituted cycloalkyl. R may also be an acyl group such as C(O)R, where R may include lower alkyl, hydroxy-substituted alkyl, polyethers (lower PEG), amino-substituted alkyl, cycloalkyl. In addition, R may include aryl and heteroaryl substituents;
e) Sulfur containing functional groups that may include thiols, sulfonic acids and corresponding amides thereof. The amides may be further defined as containing a nitrogen moiety NHR, with the N connected by a single bond to the sulfur atom, and where R is lower alkyl, cycloalkyl, or heterosubstituted alkyl or heterosubstituted cycloalkyl. R may also be an acyl group such as C(O)R, where R may include lower alkyl, hydroxy-substituted alkyl, polyethers (lower PEG), amino-substituted alkyl, cycloalkyl. In addition, R may include aryl and heteroaryl substituents.
f) Lower straight chain or branched alkyl groups, cycloalkyl groups, hydroxy-substituted alkyl, polyethers (lower PEG), amino-substituted alkyl, cycloalkyl and heterosubstituted cycloalkyl;
g) Oxygen groups such as hydroxy and substituted hydroxyaryl (OH or OR), where R may be chosen from the group including lower straight chain or branched alkyl groups, cycloalkyl groups, hydroxy-substituted alkyl, polyethers (lower PEG), amino-substituted alkyl, cycloalkyl and hetero-substituted cycloalkyl. In addition, R may include acyl, aryl and heteroaryl substituents; and
h) Cyano or halogens (F, Cl, Br, I).

In a preferred embodiment utilizing L1, n=4, X is bromo and Y is ethoxy. Moreover, P4 is selected such that L, M and N are all hydroxyl in the para position relative to the porphyrin ring. The toxin is selected to be crizotinib.

The cytotoxic activity and/or efficacy of a PAC compound is evaluated as described below. A set of tumor and normal cell lines are evaluated in vitro. The CellTiter-Glo® Assay (Promega Corporation) is used to determine the cytotoxicity activity of an individual PAC compound as disclosed herein over a range of concentrations to determine a dose-response curve. The PAC compounds to be tested are kept in the dark, at −20° C., until use. Abbreviations: TCPP=tetra(4-carboxyphenyl)porphyrin; THPP=meso-tetrakis(3-hydroxyphenyl) porphyrin. Exemplary cell lines selected for the assay are listed in Table 10. Entries 4 are cancer cell lines while entries 5-6 are normal cell lines

TABLE 10

Cell lines for in vitro assay

| Entry | Cell Line | Tissue | NCI-60 line |
|---|---|---|---|
| 1 | NCI-H460 | Lung | yes |
| 2 | MDA-MB-231 | Breast (triple negative) | yes |
| 3 | HepG2 | Liver | no |
| 4 | PC3 | Prostate | yes |
| 5 | Lonza CC-2547 | SAEC-Small Airway Epithelial Cells | no |
| 6 | Lonza CC-2551 | HMEC-Mammary Epithelial Cells | no |

Cell culture conditions: cells are thawed, grown and split twice prior to conducting the cytotoxicity assay, or until satisfactory cell growth has been established. Cells are grown in their appropriate medium; the culture media for cancer cell lines will be supplemented with 5% fetal bovine serum (not heat-inactivated) and anti-bacterial and/or fungal agents. For the cultures of normal cell lines, the culture medium specified by the vendor will be used. For the CellTiter-Glo® Assay, cells are plated in 96-well plates with one cell line per plate. On each plate, the Assay is conducted on cells exposed to a selected PAC compound as disclosed herein (8 dose levels, 3 replicates at each dose level). On the same plate, cells are exposed to the unreactecd cytotoxic agent that corresponds to the cytotoxic agent incorporated into the PAC compound being tested on the plate as a positive control (3 replicates). On each plate, the Assay is conducted on cells grown in their appropriate medium, without any of the above-mentioned additives (3 replicates). This is the negative control of the experiment.

The cell assay is ideally conducted in the dark or low light conditions. A PAC compound is dissolved in a 100% DMSO solution and tested in the assay over a concentration range as shown in Table 11.

TABLE 11

Dose range for testing PAC compounds and cytotoxins.
Dose Concentrations (nM)

| 1 | 2 | 3 | 4 | 5 | 6 | 7 | 8 |
|---|---|---|---|---|---|---|---|
| 10,000 | 3,165 | 1,001 | 317 | 100 | 32 | 10.0 | 3.2 |

For example, a positive control such as Doxorubicin is used at 10 uM doxorubicin.

Media (negative control): Since the PAC compounds and cytotoxic agents are dissolved in 100% DMSO, the negative control of "medium only" is DMSO as well. The percentage of DMSO in the "medium only" control is equal that of the highest DMSO concentration in the concentration range of PAC compounds and cytotoxins.

CeliTiter-Glo® Assay should is performed 72 hours after first exposing cells to the various PAC compounds, to discriminate between metabolically active (indicating live, quiescent, and senescent cells) and metabolically inactive (dead) cells.

In Vivo Testing of PAC compounds

In order to evaluate the efficacy of a particular PAC compound for a particular medicinal application, the compounds are first tested against appropriately chosen test cells in vitro. In a non-limiting example, PAC compounds are tested against tumor cells, for example, lung tumor cells in murine in vivo models.

Animals: Male nude (nu/nu) mice 5-6 weeks of age weighing approximately 22-25 g at the time of tumor implantation are used. Xenografts: Mice were implanted subcutaneously in the axilla region by trocar with fragments of NCI-H460 human non-small cell lung cancer tumors harvested from s.c. growing tumors in nude mice hosts. When the tumors are approximately 248-270 $mm^3$ in size (11-15 days following implantation), the animals are pair-matched into treatment and control groups. Each group contains 8 mice bearing tumors, each of which is ear-tagged and followed individually throughout the experiment.

Test Article Formulation Preparation: On each day of dosing, the porphyrin conjugate is weighed and the appropriate volume of DMSO added for initial dissolution. To this is added either 5% dextrose in water (D5W), isotonic saline or glycerol, or a combination of the above, for preparation of the stock solution. Thus, a stock solution, 0.1-1.0 mg/mL is then diluted to lower concentrations through serial dilutions. Dosing solutions are prepared immediately prior to dosing in sterile scintillation vials. Similarly, the parent porphyrin and toxin control compounds are formulated as per the conjugate.

Compound Dose Preparation: Preparation process is developed based on compound properties in vehicles suitable for parenteral administration to the test animals. Conjugates are dissolved in DMSO and then diluted with one or a combination of the following diluents: isotonic saline, D5W or glycerol to prepare stock solutions, which are further serially diluted for intraperitoneal (IP) or intravenous (i.v.) administration. The dose ranges for the conjugate, parent porphyrin and parent toxin are 1-100 mg/kg.

Dosing Solution Storage: Prepared test article dosing solutions used on the day of preparation are maintained at controlled ambient temperature in the absence of light and during dosing and sampling. Prepared test article dosing solutions not used on the day of preparation are discarded.

Dosing Procedure: The administration of vehicle or test agents begins the same day as pair-matching (Day 11). The doses are administered by IP or i.v. injection at a constant dose volume of 10 mL/kg based upon each animal's body weight at that time.

Tumor Volume: Tumor volumes are monitored twice weekly by measuring the width (mm) and length (mm) of the tumor mass using digital calipers. Tumor measurements are converted to a tumor volume ($mm^3$) using the formula, {width $(mm)^2$×length (mm)}×0.52.

Body Weight: All mice are individually weighed prior to each dose, but only recorded twice weekly. Clinical Observations: Abnormal clinical signs are recorded for all mice before each dosing and frequently after each dose. Abnormal clinical signs are recorded on all mice at the time of body weight measurements on non-dosing days. Mortality evaluations are performed on all mice daily.

Data Analysis: In this experiment the tumor growth inhibition and tumor growth delay for each treatment group compared to their respective control group is reported. Tumor growth inhibition (T/C) is calculated using the mean tumor volume from each group on the day the median control mouse volume reaches 1000 $mm^3$. Tumor growth delay utilized the time required for the median mouse in each group to reach the same tumor volume endpoint of 2000 $mm^3$. This data is reported as T-C and T/C tumor growth delay. The classification of antitumor activity of each treatment group is based on similar parameters found in two publications (Hill, 2001; Johnson, et al., 2001), the latter reference from the National Cancer Institute (Bethesda, Md.). The table below summarizes these finding.

| Rating Tumor Growth Inhibition | Tumor Growth Delay (T/C) |
|---|---|
| Active <60% | >1.5x |
| Moderate <40% | 1.75x |
| High <10% | 2x |

Partial and complete regressions are also monitored. A partial regression occurs when a tumor regresses by 50% or more compared to its size at the time of first dosing. A tumor is notated as a complete regression when the tumor is no longer visible or palpable. Toxic deaths are deaths that occur during the course of dosing or immediately following the conclusion of dosing. For recording of the percent body weight change in each group, the following formula was employed: (Day 'x' mean weight–Day 1 mean weight)/Day 1 weight×100%. The % maximal weight loss for each group was the maximum weight loss which occurred during the first two weeks following drug administration.

Note that in the specification and claims, "about" or "approximately" means within +/–twenty percent (20%) or in a preferred embodiment+/–ten percent (10%) of the numerical amount cited. Although the invention has been described in detail with particular reference to these preferred embodiments, other embodiments can achieve the same results. For example, the porphyrin cytotoxic conjugate can be combined with a biodegradable matrix material (such as alginate, polylactic acid, polyglycolic acid, caprolactone etc) and implanted in a tissue such that the porphyrin cytotoxic agent is delivered to the tissue over time as the biodegradable matrix dissolves. Variations and modifications of the present invention will be obvious to those skilled in the art and it is intended to cover all such modifications and equivalents. For example, in the formula Pn-Ln-Tn, the n of Ln may be selected from 1-300 in one embodiment of the present invention. The entire disclosures of all references, applications, patents, and publications cited above and/or in the attachments, and of the corresponding application(s), are hereby incorporated by reference.

What is claimed is:

1. A compound of Formula III

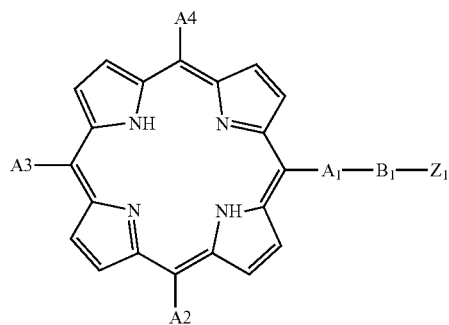

Formula III or a pharmaceutically acceptable salt thereof, wherein
an $A_1$, A2, A3 and A4 are each covalently attached to a porphyrin ring of Formula III and $A_1$, A2, A3, and A4 are independently selected from a substituted aromatic ring or a six membered heteroaromatic ring containing a single nitrogen atom at the 2, 3 or 4 position relative to the porphyrin ring;
$B_1$ is a covalent linker moiety which connects $A_1$ to a cytotoxic agent $Z_1$ and is selected from

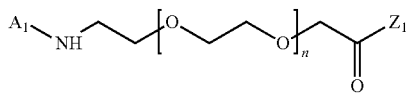 L9

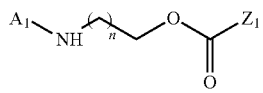 L10

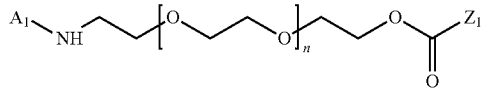 L11

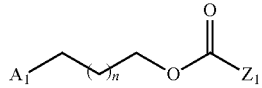 L12

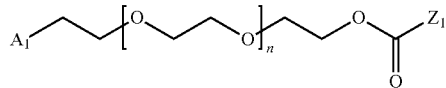 L13

L14

L15

L16 wherein n is selected from 1-12; and
the $Z_1$ is a cytotoxic agent selected from

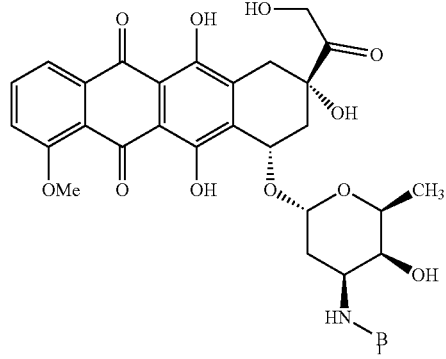 T1b

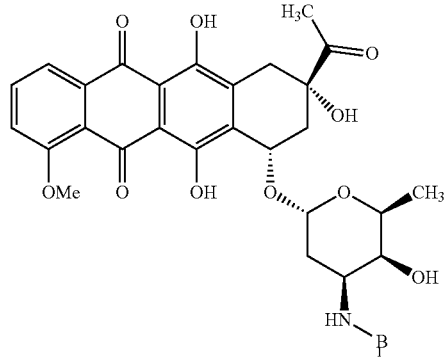 T2b

-continued
T3b
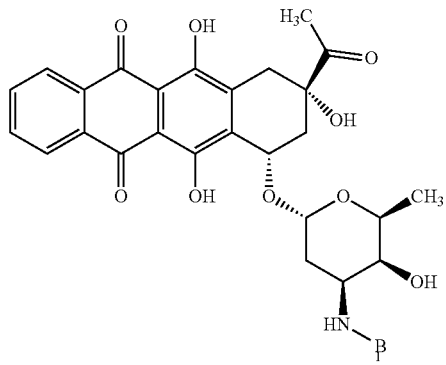
T3a
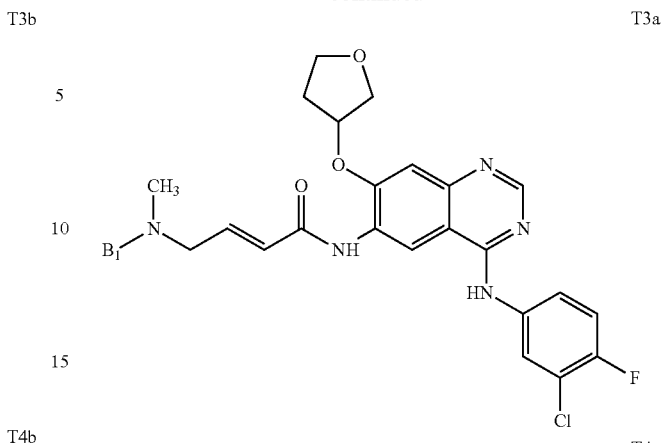
T4b
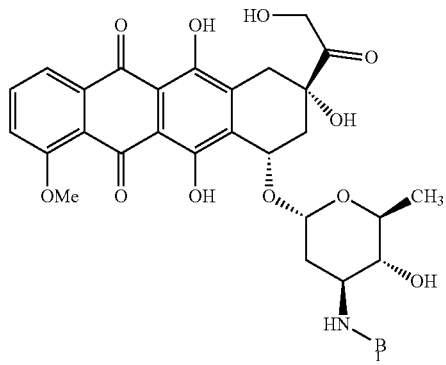
T4a
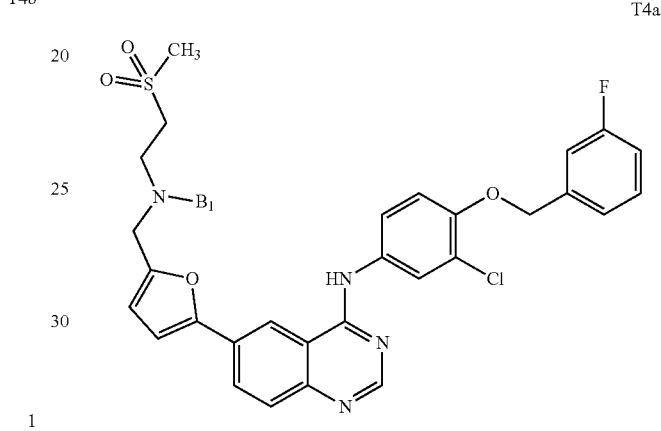
T1a
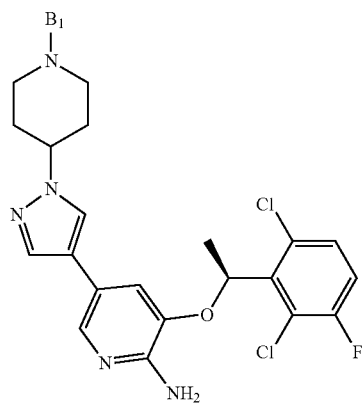
T8a
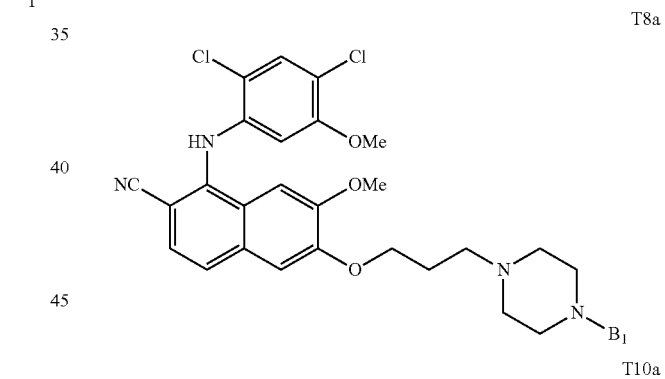
T10a
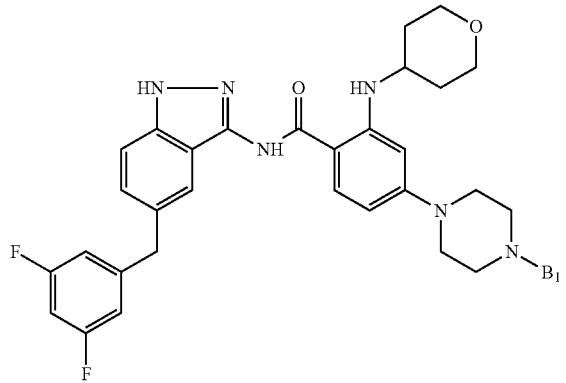
T14a
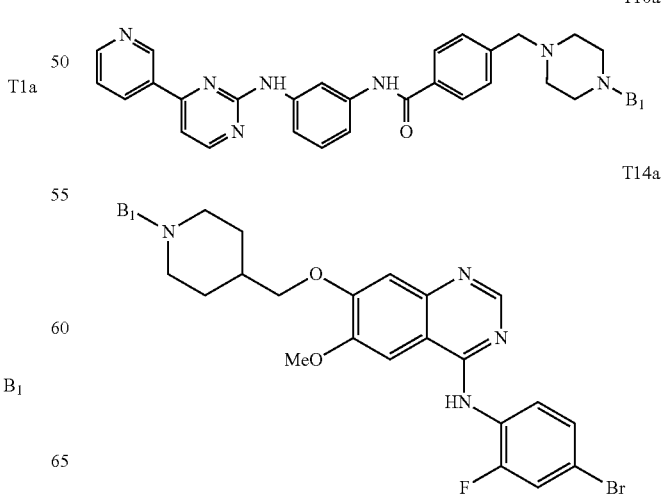

T15a
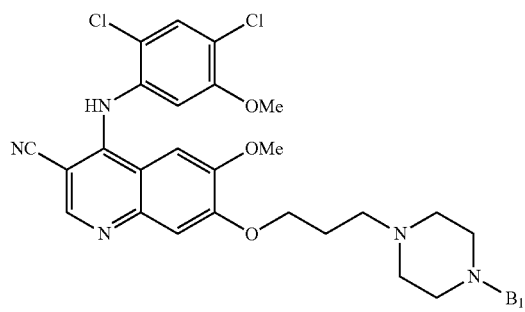
T27a
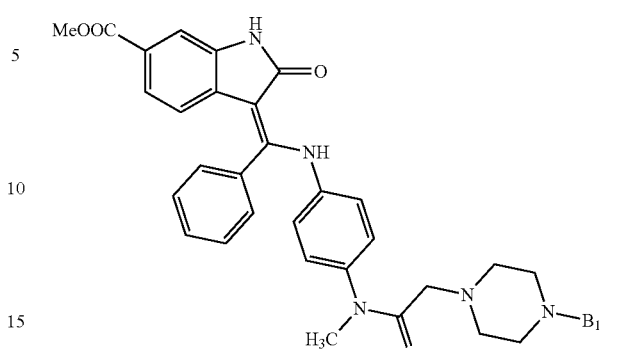
T18a
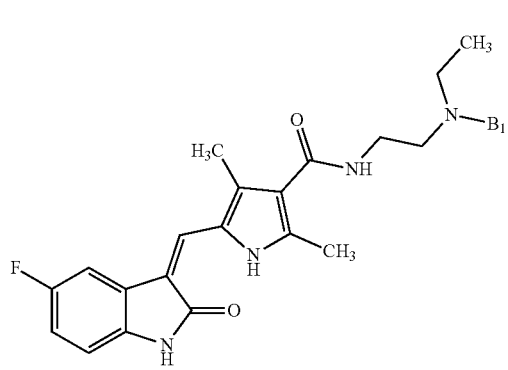
T31a
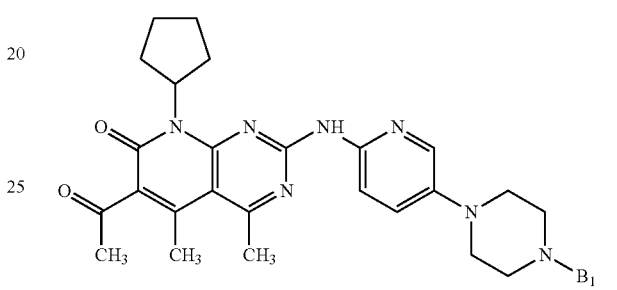
T32a
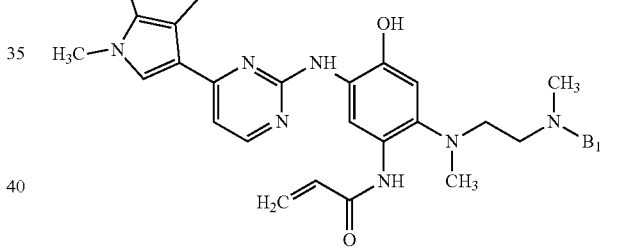
T19a
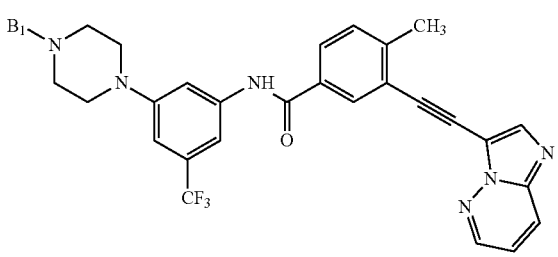
T33a
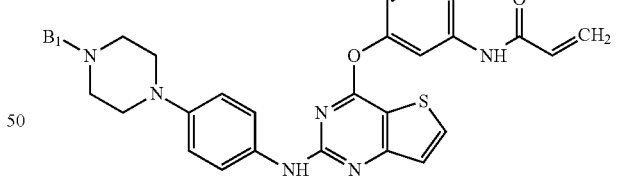
T21a
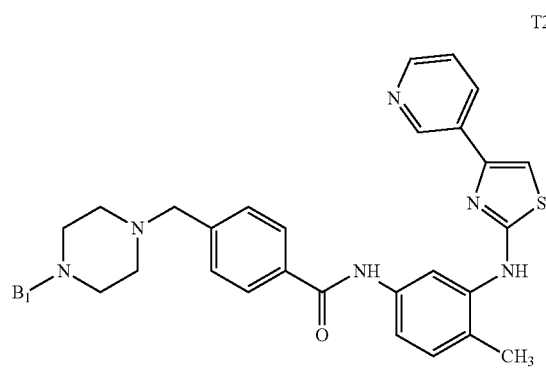
T4c
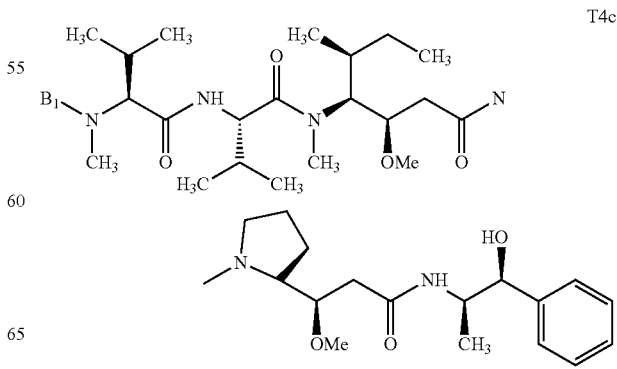

-continued

T5c
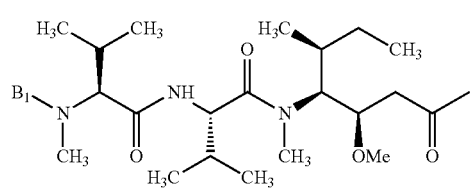

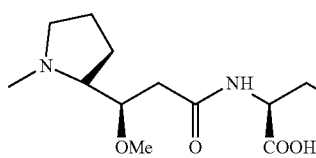

T9c
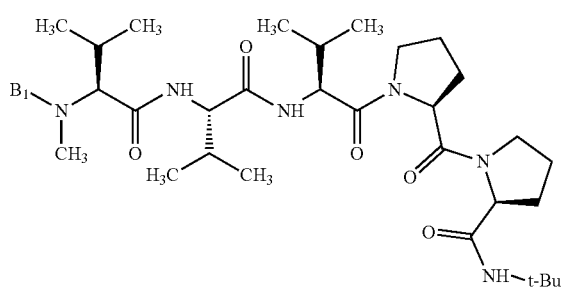

T10c
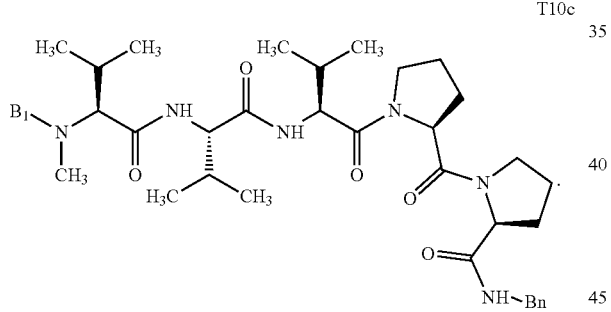

2. The compound of claim 1 or the pharmaceutically acceptable salt thereof, wherein the six membered heteroaromatic ring of $A_1$ comprises a nitrogen atom where a position of the nitrogen atom on the six membered heteroaromatic ring may occupy one of a 2, 3 or 4 position with respect to the porphyrin ring, A2, A3 and A4 are each a pyridine ring where the position of a pyridine nitrogen on each pyridine ring of A2, A3 and A4 may independently occupy one of the 2, 3 or 4 position with respect to the porphyrin ring.

3. The compound of claim 2 or the pharmaceutically acceptable salt thereof, wherein the six membered heteroaromatic ring comprising the nitrogen atom at $A_1$ is a pyridinium where the position of the nitrogen is in the 4 position with respect to the porphyrin ring, $B_1$ is L9 or L15, and $Z_1$ is selected from T1b, 1 or T4c.

4. The compound of claim 2 or the pharmaceutically acceptable salt thereof, wherein the compound is selected from OS0025
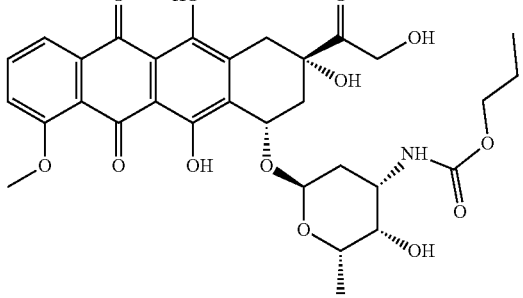

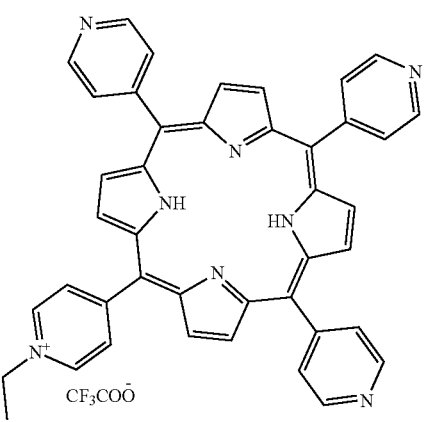

OS0026
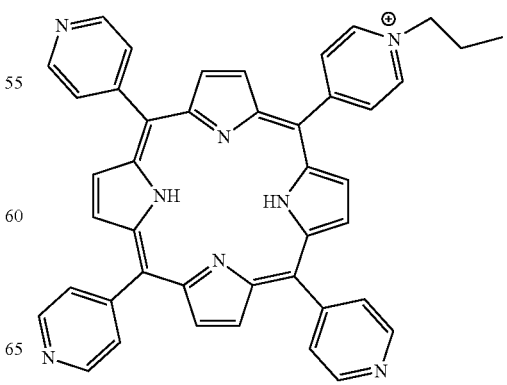

73
-continued
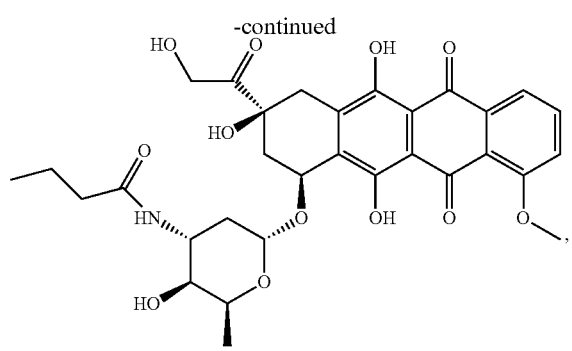
OS0027
74
-continued
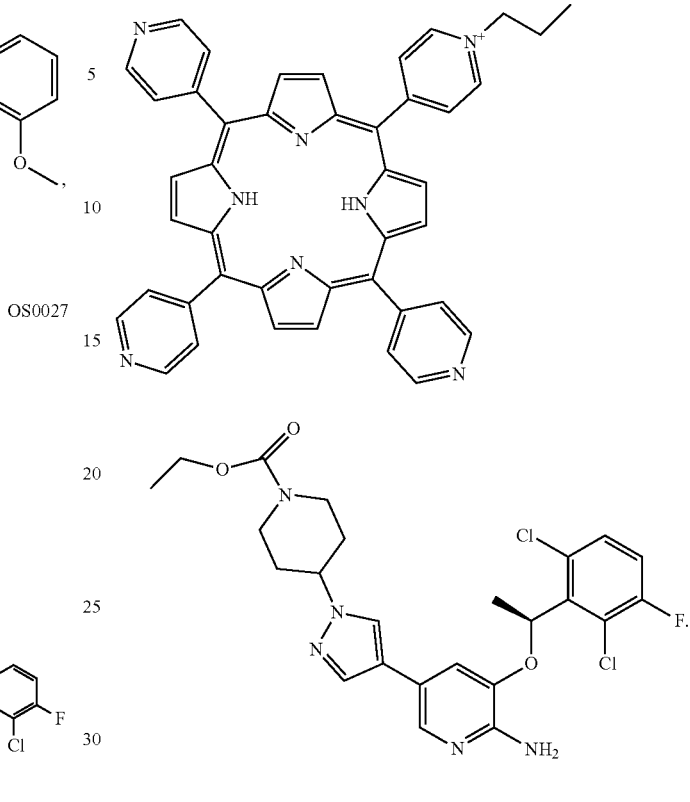
OS0029
* * * * *